United States Patent
Feinstein et al.

(10) Patent No.: US 6,998,232 B1
(45) Date of Patent: Feb. 14, 2006

(54) METHODS OF DIAGNOSING BLADDER CANCER

(75) Inventors: Elena Feinstein, Rehovot (IL); Orna Mor, Kiryat Ono (IL)

(73) Assignee: Quark Biotech, Inc., Fremont, CA (US)

( * ) Notice: Subject to any disclaimer, the term of this patent is extended or adjusted under 35 U.S.C. 154(b) by 193 days.

(21) Appl. No.: 09/825,682

(22) Filed: Apr. 4, 2001

Related U.S. Application Data

(63) Continuation-in-part of application No. PCT/US00/41005, filed on Sep. 27, 2000.
(60) Provisional application No. 60/156,153, filed on Sep. 27, 1999.

(51) Int. Cl.
| | |
|---|---|
| C12Q 1/68 | (2006.01) |
| C12P 19/34 | (2006.01) |
| C07H 21/04 | (2006.01) |
| G01N 33/53 | (2006.01) |
| C07K 14/47 | (2006.01) |

(52) U.S. Cl. .......................... 435/6; 435/7.1; 435/91.2; 435/91.51; 536/23.5; 536/24.31; 530/350

(58) Field of Classification Search .................. 435/6, 435/7.1, 91.2, 91.51; 536/23.5, 24.31; 530/350
See application file for complete search history.

(56) References Cited

U.S. PATENT DOCUMENTS

| | | | |
|---|---|---|---|
| 3,791,932 A | 2/1974 | Schuurs et al. | |
| 3,839,153 A | 10/1974 | Schuurs et al. | |
| 3,850,578 A | 11/1974 | McConnell | |
| 3,850,752 A | 11/1974 | Schuurs et al. | |
| 3,853,987 A | 12/1974 | Dreyer | |
| 3,867,517 A | 2/1975 | Ling | |
| 3,879,262 A | 4/1975 | Schuurs et al. | |
| 3,901,654 A | 8/1975 | Gross | |
| 3,935,074 A | 1/1976 | Rubenstein et al. | |
| 3,984,533 A | 10/1976 | Uzgiris | |
| 3,996,345 A | 12/1976 | Ullman et al. | |
| 4,034,074 A | 7/1977 | Miles | |
| 4,098,876 A | 7/1978 | Piasio et al. | |
| 4,439,194 A | 3/1984 | Harwood et al. | |
| 4,447,224 A | 5/1984 | DeCant et al. | |
| 4,447,233 A | 5/1984 | Mayfield | |
| 4,475,196 A | 10/1984 | La Zor | |
| 4,486,194 A | 12/1984 | Ferrara | |
| 4,487,603 A | 12/1984 | Harris | |
| 4,666,828 A | 5/1987 | Gusella | |
| 4,683,202 A | 7/1987 | Mullis | |
| 4,736,866 A | 4/1988 | Leder et al. | |
| 4,801,531 A | 1/1989 | Frossard | |
| 4,866,042 A | 9/1989 | Neuwelt | |
| 4,879,219 A | 11/1989 | Wands et al. | |
| 4,925,678 A | 5/1990 | Ranney | |
| 4,959,217 A | 9/1990 | Sanders et al. | |
| 5,011,771 A | 4/1991 | Bellet et al. | |
| 5,167,616 A | 12/1992 | Haak | |
| 5,169,383 A | 12/1992 | Gyory | |
| 5,175,383 A | 12/1992 | Leder et al. | |
| 5,175,384 A | 12/1992 | Krimpenfort et al. | |
| 5,175,385 A | 12/1992 | Wagner et al. | |
| 5,192,659 A | 3/1993 | Simons | |
| 5,221,778 A | 6/1993 | Byrnes et al. | |
| 5,225,182 A | 7/1993 | Sharma | |
| 5,225,347 A | 7/1993 | Goldberg et al. | |
| 5,272,057 A | 12/1993 | Smulson et al. | |
| 5,281,521 A | 1/1994 | Trojanowski et al. | |
| 5,288,846 A | 2/1994 | Quertermous et al. | |
| 5,298,422 A | 3/1994 | Schwartz et al. | |
| 5,347,075 A | 9/1994 | Sorge | |
| 5,360,735 A | 11/1994 | Weinshank et al. | |
| 5,387,742 A | 2/1995 | Cordell | |
| 5,422,243 A * | 6/1995 | Jalkanen et al. ................ 435/6 |
| 5,464,764 A | 11/1995 | Capecchi et al. | |
| 5,487,992 A | 1/1996 | Capecchi et al. | |
| 5,856,136 A | 1/1999 | Au-Young | |
| 6,207,380 B1 | 3/2001 | Billing-Medel et al. | |
| 6,335,170 B1 * | 1/2002 | Orntoft ......................... 435/6 |

FOREIGN PATENT DOCUMENTS

WO    WO0122864    4/2001

OTHER PUBLICATIONS

Rintala, M. et al. Association of syndecan–1 with tumor grade and histology in primary invasive cervical carcinoma. Gynecologic Oncology 75(3):372–378 (Dec. 1999).*

U.S. Appl. No. 09/670,672, filed Sep. 27, 2000, Feinstein and Mor.

Ozen, "Bladder Cancer," *Curr. Opin. Oncol.* 10(3):273–278 (1998).

Torti and Lum, "The Biology and Treatment of Superficial Bladder Cancer," *J. Clin. Oncol.* 2(5):505–531 (1984).

Grossman, "New Methods for Detection of Bladder Cancer," *Semin. Urol. Oncol.* 16(1):17–22 (1998).

(Continued)

*Primary Examiner*—Diana B. Johannsen
(74) *Attorney, Agent, or Firm*—Cooper & Dunham LLP; John P. White

(57) ABSTRACT

There is provided a method of diagnosing the presence of bladder cancer in a patient by analyzing a tissue sample from the patient for the presence of a least one expressed gene wherein the presence of the expressed gene is indicative of bladder cancer. Also provided by the present invention is a polynucleotide sequence whose expression is indicative of bladder cancer. A marker for bladder cancer is also provided. There are also provided methods of diagnosing bladder cancer by screening for the presence of at least one expressed gene wherein the presence of the expressed gene is indicative of bladder cancer. Methods of treating and regulating bladder cancer-associated pathologies by administering to a patient a therapeutically effective amount of chemical compound are also provided.

7 Claims, 7 Drawing Sheets

OTHER PUBLICATIONS

Sarver et al. "Exploring Catalytic RNAs (Roiboxymes) as Anti–HIV Agents," pp. 305–325 in *Gene Regulation and AIDS* by Papas, Portfolio Publishing Co. Woodlands, Texas (1990).

Culver, "Site–Directed recombinant for repair of mutations in the human ADA gene," (Abstract) *Antisense DNA & RNA based therapeutics*, Coronado, California (1998).

Lacombe et al., "Overexpression of p53 protein in a high–risk population of patients with superficial bladder cancer before and after bacillus Calmette–Guerin therapy; correlation to clinical outcome," *J. Urol.* 153(3) Part 1:564–572 (1995).

Herskowitz "Functional inactivation of genes by dominant negative mutations" *Nature* 329: 219–222 (1987).

Hudson and Herr, "Carcinoma in situ of the bladder," *J. Urol.* 153(3) Part 1:564–572 (1995).

Rosenthal et al., "Human bladder tumour cDNA library derived EST 15", Geneseq032802 Accession No. AAZ24403, submitted Feb. 2000.

National Institutes of Health, Mammalian Gene Collection, "Homo sapiens cDNA clone", EST Accession No. BG291376, submitted Feb. 2000.

Quark Biotech Inc., "Bladder cancer–associated sequence, TCC75E3", Geneseq032802 Accession No. AAS01308, submitted Jul. 2001.

Quark Biotech Inc., "Bladder cancer–associated sequence, TCC94G3", Geneseq032802 Accession No. AAS01297, submitted Jul. 2001.

Billing–Medel et al., "Sequence 7 from patent US 6,207,380", GeneEmbl Accession No. AR139477, submitted Jun. 2001.

Burke and Olson, "Preparation of Clone Libraries in yeast Artifical Chromosome Vectors" in *Methods in Enzymology*, vol. 194, "Guide to Yeast Genetics and Molecular Biology", Guthrie and Fink (eds.), Academic Press, Inc. Chap. 17, pp. 251–270 (1991).

Capecchi, "Altering the genome by homologous recombination," *Science* 244:1288–1292 (1989).

Cregg et al., "Recent Advanced in the Expression of Foreign Genes in *Pichia pastoris*," Bio/Technology 11:905–910 (1993).

Davies et al., "Targeted alterations in yeast artifical chromosomes for inter–species gene transfer," *Nucleic Acids Research* 20(11):2693–2698 (1992).

Diatchenko et al., "Suppression subtractive hybridization: A method for generating differentially regulated or tissue–specific cDNA probes and libraries," *Proc. Natl. Acad. Sci.* 93:6025–6030 (1996).

Dickinson et al., "High frequency gene targeting using insertional vectors," *Human Molecular Genetics* 2(8):1299–1302 (1993).

Duff and Lincoln, "Insertion of pathogenic mutation into a yeast artificial chromosome containing the human APP gene and expression in ES cells," in *Research Advances in Alzheimer's Disease and Related Disorders* (1995).

Gilboa et al., "Transfer and expression of cloned genes using retroviral vectors," *BioTechniques* 4(6):504–512 (1986).

Huston et al., "Protein engineering of single chain Fv analogs and fusion proteins," in *Methods in Enzymology*, JJ Langone, ed.; Academic Press, New York, 203:46–88 (1991).

Huxley et al. "The human HPRT gene on a yeast artificial chromosome is function when transferred to mouse cells by cell fusion," *Genomics* 9:742–750 (1991).

Jakobovits et al. "Germ–line transmission and expression of a human–derived yeast artificial chromosome," *Nature* 362:255–261 (1993).

Johnson and Bird, "Construction of single–chain Fvb derivatives of monovclonal antibodies and their production in *Escherichia coli*," in *Methods in Enzymology*, JJ Langone, ed.; Academic Press, New York, 203:88–99 (1991).

Lamb et al., "Introduction and expression of the 400 kilobase precursor amyloid gene in transgenic mice," *Nature Genetics* 5:22–29 (1993).

Mernaugh and Mernaugh "An overview of phage–displayed recombinant antibodies," in *Molecular Methods in Plant Pathology*, Singh and Singh, eds.; CRC Press, Inc., Boca Roton, Florida, pp 359–365 (1995).

Pearson and Choi, "Expression of the human β–amyloid precursor protein gene from a yeast artificial chromosome in transgenic mice," *Proc. Natl. Acad. Sci. USA* 90:10578–10582 (1990).

Rothstein, "Targeting, disruption, replacement, and allele rescue: integrative DNA transformation in yeast" in *Methods in Enzymology*, vol. 194, "Guide to Yeast Genetics and Molecular Biology," Guthrie and Fink (eds.), Academic Press, Inc. Chap. 19, pp. 281–301 (1991).

Schedl et al., "A yeast artificial chromosome covering the tyrosinase gene confers copy number–dependent expression in transgenic mice," *Nature* 362:258–261 (1993).

Strauss et al. "Germ line transmission of a yeast artificial chromosome spannin the murine $\alpha_1$ (I) collagen locus," *Science* 259:1904–1907 (1993).

American Cancer Society, "Estimating New Cancer Cases and Deaths By Sex For All Sites," *Cancer Facts and Figures*, p. 4 (1998.).

* cited by examiner

SEQUENCE LISTING

```
<160> NUMBER OF SEQ ID NOS: 63

<210> SEQ ID NO 1
<211> LENGTH: 156
<212> TYPE: DNA
<213> ORGANISM: Homo sapiens

<400> SEQUENCE: 1
tccgtctcat tgagggtcct gaggaagttg atctcatcat tcagggcatc caccttggcc      60
tccagctcca ccttgctcat gtaggcagca tccacatcct tcttcagcac cacaaactca     120
ttctcagcag ctgtgcggcg gttaatttca tcttcg                               156

<210> SEQ ID NO 2
<211> LENGTH: 219
<212> TYPE: DNA
<213> ORGANISM: Homo sapiens

<400> SEQUENCE: 2
aaggcttatt ccatccggac cgcatccgcc agtcgcagga gtgcccgcga ctgagccgcc      60
tcccaccact ccactcctcc agccaccacc cacaatcaca agaagattcc cacccctgcc     120
tcccatgcct ggtcccaaga cagtgagaca gtctggaaag tgatgtcaga atagcttcca     180
ataaagcagc ctcattctga ggcctgagtg aaaaaaaaa                            219

<210> SEQ ID NO 3
<211> LENGTH: 133
<212> TYPE: DNA
<213> ORGANISM: Homo sapiens
```

```
<220> FEATURE:
<221> NAME/KEY: misc_feature
<222> LOCATION: (3)..(132)
<223> OTHER INFORMATION: n = unknown

<400> SEQUENCE: 3
cantatataa cnaattggag ctcaatngcn cgcggncgcg tgtcttctgg gtagagggat      60
gngaaggaag ggacccttac ccccggctct tctcctgacc tgccaataaa aatttatggt    120
ccaaggnaaa ana                                                       133

<210> SEQ ID NO 4
<211> LENGTH: 417
<212> TYPE: DNA
<213> ORGANISM: Homo sapiens
<220> FEATURE:
<221> NAME/KEY: misc_feature
<222> LOCATION: (23)..(347)
<223> OTHER INFORMATION: n = unknown

<400> SEQUENCE: 4
actcattgaa cttgagctcc gantcctgat tcncatcnaa gctctnnatc tgctcatcan     60
gagancccac atccttgagc agatgggnca nctgctgntt aaccanctct nngaactcgn   120
agannntaag gctatccttc cggncctcct gccttgcaaa ggtgaagaaa gtggtgnnca   180
cngtcncaat ggantcctct agctctgtca gtggttctgc tgcnattatg gaacctgagg   240
ccaaagctga tgtcctcaag gggctagctg acctttgtca gggctgacct ctcctcagcg   300
gcagcagggc agagtgctga acccaggaac ccacagatcc tccccgntcc tgtctcccgg   360
tgacaagggt cctggaacgg ggcgtctctg actccctgct ccaggacggg tttaagt      417

<210> SEQ ID NO 5
<211> LENGTH: 124
<212> TYPE: DNA
<213> ORGANISM: Homo sapiens

<400> SEQUENCE: 5
actttgagaa ggcaggactc aaatgatgcc ctggagatgt cacagattcc tggcagagcc    60
atggtcccag gcttcccaaa agtgtttgtt ggcaattatt cccctaggct gagcctgctc   120
atgt                                                                124

<210> SEQ ID NO 6
<211> LENGTH: 146
<212> TYPE: DNA
<213> ORGANISM: Homo sapiens
<220> FEATURE:
<221> NAME/KEY: misc_feature
<222> LOCATION: (20)..(56)
<223> OTHER INFORMATION: n = unknown

<400> SEQUENCE: 6
gactagaacc cacccccttn ccttccagcc tttctgtcat catctccaca gnccanccat     60 ccctgagca cactaaccat ctcatgcagg ccccacctgc aatagtaat aaagcaatgt    120 cactttgtta aaacatgaaa aaaaaa                                        146

<210> SEQ ID NO 7
<211> LENGTH: 165
<212> TYPE: DNA
<213> ORGANISM: Homo sapiens
<220> FEATURE:
<221> NAME/KEY: misc_feature
<222> LOCATION: (15)..(48)
```

<223> OTHER INFORMATION: n = unknown

<400> SEQUENCE: 7

| ctagtataca ctccncatag natacgttgc agctcaattg cgcgcggncg cggacgacga | 60 |
| cctgcgaggg tgtcttctgg gtagagggat gggaaggaag ggaccttac ccccggctct | 120 |
| tctcctgacc tgccaataaa aatttatggt ccaaggaaaa aaaaa | 165 |

<210> SEQ ID NO 8
<211> LENGTH: 359
<212> TYPE: DNA
<213> ORGANISM: Homo sapiens
<220> FEATURE:
<221> NAME/KEY: misc_feature
<222> LOCATION: (7)..(354)
<223> OTHER INFORMATION: n = unknown

<400> SEQUENCE: 8

| tttttttnnat nttatttgg gtattggtgt tnttctttt ttcctcttnc cttcttaact | 60 |
| caagacttgt agtgttgtaa acctgcctca caaatacat ggtaataact tntctttaaa | 120 |
| aaaanaaaaa agacagnctt nacaccattt ctaatngnan nactattttt gggcaatgtt | 180 |
| atgcaccact tcaatttccc cattgtgacc cctatcactt catttgatat cccttttnga | 240 |
| cccanccatc tccttcatat atgggcatgt ccatagatta acaaagaaag tttacactt | 300 |
| ngaataaaga tgcaaagtat gcaaaaacat taatactgat gcnaaaaaa ntanaaaaa | 359 |

<210> SEQ ID NO 9
<211> LENGTH: 190
<212> TYPE: DNA
<213> ORGANISM: Homo sapiens

<400> SEQUENCE: 9

| ggtaccgacg gacctgcgga gactcctgcc ctgttgtgta tagatgcaag atatttatat | 60 |
| atatttttgg ttgcaatatt aaatacagac actaagttat agtatatctg gcaagccaac | 120 |
| ttgtaaatca ccacctcact cctgtactta cctaaacaga tataaatggc tggttttaa | 180 |
| gaaaaaaaaa | 190 |

<210> SEQ ID NO 10
<211> LENGTH: 178
<212> TYPE: DNA
<213> ORGANISM: Homo sapiens
<220> FEATURE:
<221> NAME/KEY: misc_feature
<222> LOCATION: (81)..(150)
<223> OTHER INFORMATION: n = unknown

<400> SEQUENCE: 10

| accctgggag agaagtttga agaaaccaca gctgatggca gaaaaactca gactgctgca | 60 |
| actttacaga tggtgcattg ngtcagcata ggagtgagat ggggaaggaa agcacantaa | 120 |
| caagaaaatt ganagatgnt aaattagtgn tggagtgtgt catgaacaat gcacctgt | 178 |

<210> SEQ ID NO 11
<211> LENGTH: 157
<212> TYPE: DNA
<213> ORGANISM: Homo sapiens

<400> SEQUENCE: 11

| tagtgtggaa gcatagtgaa cacactgatt aggttatggt ttaatgttac aacaactatt | 60 |
| ttttaagaaa aacatgtttt agaaatttgg tttcaagtga catgtgtgaa aacaatatcg | 120 |

-continued atactaccat agtgagccat gattttctaa aaaaaaa                                157

<210> SEQ ID NO 12
<211> LENGTH: 157
<212> TYPE: DNA
<213> ORGANISM: Homo sapiens

<400> SEQUENCE: 12
tagtgtggaa gcatagtgaa cacactgatt aggttatggt ttaatgttac aacaactatt       60
ttttaagaaa aacaagtttt agaaatttgg ttcaagtgac atgtgtgaaa acaatattgt      120
atactaccat agtgagccat gattttctaa aaaaaaa                                157

<210> SEQ ID NO 13
<211> LENGTH: 320
<212> TYPE: DNA
<213> ORGANISM: Homo sapiens

<400> SEQUENCE: 13
aaagagggcg gcaggggcct ggagatcctc ctgcagacca cgcccgtcct gcctgtggcg       60
ccgtctccag gggctgcttc ctcctggaaa ttgacgaggg gtgtcttggg cagagctggc      120
tctgagccgc cctccatcca aggccaggtt ctccgttagc tcctgtggcc ccaccctggg      180
ccctgggctg gaatcaggaa tattttccaa agagtgatag tcttttttgct ttttggcaaa    240 actctactta atccaatggg ttttttctctg tacagtagat tttccaaatg taataaactt     300
taatataaag taaaaaaaaa                                                   320

<210> SEQ ID NO 14
<211> LENGTH: 221
<212> TYPE: DNA
<213> ORGANISM: Homo sapiens

<400> SEQUENCE: 14
aaagtcatcc tccgtctacc agagcgtgca cttgtgatcc taaaataagc ttcatctccg       60
ggctgtgccc cttggggtgg aagggggcagg attctgcagc tgcttttgca tttctcttcc    120
taaatttcat tgtgttgatt tctttccttc ccaataggtg atcttaatta ctttcagaat       18
attttcaaaa tagatatatt tttaaaatcc ttaaaaaaaa a

<210> SEQ ID NO 15
<211> LENGTH: 157
<212> TYPE: DNA
<213> ORGANISM: Homo sapiens

<400> SEQUENCE: 15
ctctccagtt tgcacctgtc cccaccctcc actcagctgt cctgcagcaa acactccacc       60
ctccaccttc catttttcccc cactactgca gcacctccag gcctgttgct atagagccta    120
cctgatgtca ataaacaaca gctgaagcaa aaaaaaa                                157

<210> SEQ ID NO 16
<211> LENGTH: 112
<212> TYPE: DNA
<213> ORGANISM: Homo sapiens
<220> FEATURE:
<221> NAME/KEY: misc_feature
<222> LOCATION: (11)..(13)
<223> OTHER INFORMATION: n = unknown

<400> SEQUENCE: 16

```
aggaaaggtg ngngctggaa gcactgaacc tacctcatcc tcctggtggg tgtggctacc      60
ctcgccaccc caaattccat gtcattaaag aacagctaaa ttcaaaaaaa aa             112
```

<210> SEQ ID NO 17
<211> LENGTH: 158
<212> TYPE: DNA
<213> ORGANISM: Homo sapiens

<400> SEQUENCE: 17

```
tgtccgtctt cacccatccc caagcctact agagcaagaa accagttgta atataaaatg      60
cactgcccta ctgttggtat gactaccgtt acctactgtt gtcattgtta ttacagctat     120
ggccactatt attaaagagc tgtgtaacat caaaaaaa                             158
```

<210> SEQ ID NO 18
<211> LENGTH: 398
<212> TYPE: DNA
<213> ORGANISM: Homo sapiens

<400> SEQUENCE: 18

```
caggagacca tccgcgtcac caagccctgc accccaaga ccaaagcaaa ggccaaagcc       60
aagaaaggga agggaaagga ctagacgcca agcctggatg ccaaggagcc cctggtgtca    120
catggggcct ggcccacgcc ctccctctcc caggcccgag atgtgaccca ccagtgcctt    180
ctgtctgctc gttagctttta atcaatcatg ccctgccttg tccctctcac tccccagccc   240 caccccctaag tgcccaaagt ggggagggac aagggattct gggaagcttg agcctccccc   300
aaagcaatgt gagtcccaga gcccgctttt gttcttcccc acaattccat tactaagaaa   360
cacatcaaat aaactgactt tttcccccca aaaaaaa                             398
```

<210> SEQ ID NO 19
<211> LENGTH: 362
<212> TYPE: DNA
<213> ORGANISM: Homo sapiens
<220> FEATURE:
<221> NAME/KEY: misc_feature
<222> LOCATION: (267)..(335)
<223> OTHER INFORMATION: n = unknown

<400> SEQUENCE: 19

```
ctttgacgtg gagaggaact cctgcaataa cttcatctat ggaggctgcc ggggcaataa      60
gaacagctac cgctctgagg aggcctgcat gctccgctgc ttccgccagc aggagaatcc    120
tcccctgccc cttggctcaa aggtggtgct ctggcgggg ctgttcgtga tggtgttgat     180
cctcttcctg ggagcctcca tggtctacct gatccgggtg gcacggagga accaggagcg   240
tgccctgcgc accgtctgga gctccgnaga tgacaaggag cagctggtga agaacacata   300
tgtcctgtga ccgccctgtc gccaagagga ctggngaaag ggaggggaga ctatgtgtga   360
gc                                                                   362
```

<210> SEQ ID NO 20
<211> LENGTH: 118
<212> TYPE: DNA
<213> ORGANISM: Homo sapiens

<400> SEQUENCE: 20

```
aaaaagagta aaacactttc agtttctccc ctttagcccc taaacaaca tcttacagtc       60 tggatctgga tctacctata cagtcctaca ttagcttcta aatatttgt caggaggg       118
```

<210> SEQ ID NO 21
<211> LENGTH: 216
<212> TYPE: DNA
<213> ORGANISM: Homo sapiens

<400> SEQUENCE: 21

```
cccaaatgga atgttgcccc cttaaacacc attttccctc caggaccacc ttggtttcta      60
ggcactgtgg ttcttggcag gggctgtctt aggtaaaagg gtagttgtgg agctacagtc     120
tgaagaacat agcttgggct caagttcaaa tgagccatct ttttcctttg cgttttctt     180
gactgaaggt gagatgttat tgtggcatg tgaact                                 216
```

<210> SEQ ID NO 22
<211> LENGTH: 140
<212> TYPE: DNA
<213> ORGANISM: Homo sapiens

<400> SEQUENCE: 22

```
acaaagactg ctgataacta tctgtgattg ataggaaatt ttttttcttg atttctctgt      60
gagaaatgta atgctgactt ttataaagcc tggacttcta ctttatttaa taaatcaatg     120
tttgcaatgg taaaaaaaaa                                                  140
```

<210> SEQ ID NO 23
<211> LENGTH: 145
<212> TYPE: DNA
<213> ORGANISM: Homo sapiens
<220> FEATURE:
<221> NAME/KEY: misc_feature
<222> LOCATION: (42)..(69)
<223> OTHER INFORMATION: n = unknown

<400> SEQUENCE: 23

```
gcaataaagc tgtccattca attccaaata ctggttttaa gngtatagcc actgatattc      60
tttcatgtnt agaaattctt tctgttatta ttcaagaaaa tgttttttaat catgctaata    120
aacttttttg gagatgaaaa aaaaa                                            145
```

<210> SEQ ID NO 24
<211> LENGTH: 187
<212> TYPE: DNA
<213> ORGANISM: Homo sapiens
<220> FEATURE:
<221> NAME/KEY: misc_feature
<222> LOCATION: (3)..(184)
<223> OTHER INFORMATION: n = unknown

<400> SEQUENCE: 24

```
ggnaccacgt acctgctgaa tgtntcnncg nnatgncgnc aggccatgct gttgctgatn      60
tantactntg aaaatangga tatcatgatg ggaatgcatg tcatgaggtc cagantcgtt     120
ctactgtcna taanctgtnt actngcgttg anaanaaang atgtcaaagn ccccccgtaa     180
aaangta                                                                187
```

<210> SEQ ID NO 25
<211> LENGTH: 80
<212> TYPE: DNA
<213> ORGANISM: Homo sapiens

<400> SEQUENCE: 25

```
gtcccagtct tcaccaggtg tctctcctct tttactcagg aggactttcc caggaaaacc      60
atgccactag caaaaaaaaa                                                  80
```

<210> SEQ ID NO 26
<211> LENGTH: 155
<212> TYPE: DNA
<213> ORGANISM: Homo sapiens

<400> SEQUENCE: 26
tgagtgtctt caggccaacc tggtggaaat gttgttctct gaagattaag attttaggat    60
ggcaatcatg tcttgatgtc ctgatttgtt ctagtatcaa taaactgtat acttgctttg   120
aattcatgtt agcaataaat gatgttaaaa aaaaa                              155

<210> SEQ ID NO 27
<211> LENGTH: 184
<212> TYPE: DNA
<213> ORGANISM: Homo sapiens
<220> FEATURE:
<221> NAME/KEY: misc_feature
<222> LOCATION: (24)..(170)
<223> OTHER INFORMATION: n = unknown

<400> SEQUENCE: 27
ggatcgacga cctgcttccc agangcgnnc nngaggnccn cttgttnnng ncnngnanac    60
nnacccantt nanttnnagc ctttntgnaa taaatataca caggccaccc atgccntgag   120
cacactaacc acntgatgca ggccccacct tgccaatagt aataaagcan tgggacgttt   180
ttta                                                                184

<210> SEQ ID NO 28
<211> LENGTH: 100
<212> TYPE: DNA
<213> ORGANISM: Homo sapiens
<220> FEATURE:
<221> NAME/KEY: misc_feature
<222> LOCATION: (14)..(92)
<223> OTHER INFORMATION: n = unknown

<400> SEQUENCE: 28
gggccaaagc ccgngcatcc aancccangc aaggnacaaa ngancnngga gaggannacc    60
caagcanntn ncaaccatca aatggagggc angcccgggg                         100

<210> SEQ ID NO 29
<211> LENGTH: 114
<212> TYPE: DNA
<213> ORGANISM: Homo sapiens
<220> FEATURE:
<221> NAME/KEY: misc_feature
<222> LOCATION: (13)..(106)
<223> OTHER INFORMATION: n = unknown

<400> SEQUENCE: 29
gggccaaagc cgngcatcca ancccancgc anggnanaaa ngangangga nanggatnac    60
ccangcctnt attaaccatc aantgggang gcaagcccgg ggcatntatt gatt         114

<210> SEQ ID NO 30
<211> LENGTH: 100
<212> TYPE: DNA
<213> ORGANISM: Homo sapiens
<220> FEATURE:
<221> NAME/KEY: misc_feature
<222> LOCATION: (13)..(99)
<223> OTHER INFORMATION: n = unknown

<400> SEQUENCE: 30
aggacccctg aanacnacac agatctgtgn gaaacaaggn nacntagcgt cccnaaagtg    60
ccnggttnnn gtanncnnag ngngngaccn gngcncatnt                100

<210> SEQ ID NO 31
<211> LENGTH: 227
<212> TYPE: DNA
<213> ORGANISM: Homo sapiens

<400> SEQUENCE: 31
atccagagac catcaatcct gctagagtgc agggtggcaa gcacccaagg gtggctgacc    60
aagactgcag agtctcctcc atcttcaggt ccattcagcc tcctggcatt taactaccag   120
catccagtgg tccccaagga atcccttcct agcctcctga catgagtctg ctggaaagag   180
catccaaaca aacaagtaat aaataaataa ataaactcaa aaaaaaa                 227

<210> SEQ ID NO 32
<211> LENGTH: 183
<212> TYPE: DNA
<213> ORGANISM: Homo sapiens

<400> SEQUENCE: 32
ctgcaggagt cagcgttcaa tcttgacctt gaagatggga aggatgttct ttttacgtac    60
caattctttt gtcttttgat attaaaaaga agtacatgtt cattgtagag aatttggaaa   120
ctgtagaaga gaatcaagaa gaaaaataaa atcagctgt tgtaatcacc tagcaaaaaa    180
aaa                                                                 183

<210> SEQ ID NO 33
<211> LENGTH: 297
<212> TYPE: DNA
<213> ORGANISM: Homo sapiens

<400> SEQUENCE: 33
cacgcatatg gggccagttc cacatatttg gcaaccagac cagcatccag gacaacacaa    60
agtatgttgt tgttgttag agggcttggg acatttcact cttttgccagc ctcagcttaa   120
tccaggagac aaagattatt ttccttatta tctcttctgc ataggatctg caatcagaac   180
tattgaactt ctccattcag accgccactc acacctatgg gaaaagggta atgtatcatc   240
ggcttagcaa cagggaatac tattcgtatg atggaaaatg gggacaaaag gctttgg      297

<210> SEQ ID NO 34
<211> LENGTH: 379
<212> TYPE: DNA
<213> ORGANISM: Homo sapiens
<220> FEATURE:
<221> NAME/KEY: misc_feature
<222> LOCATION: (245)..(285)
<223> OTHER INFORMATION: n = unknown

<400> SEQUENCE: 34
ctatgaatag cttcttgctt tatgactta ggattaactt gtaaaaaaca tatcctgaac     60
taagatatgc aaaatactca ttttcaagtt atggaaatgt gtttgtggca tataggactg   120
tggggtctgt gtgtgtagtg agagtgtgta tccactatta taactggaat ttaatttaca   180
ttcataaact actatatttc ccatcttgca aatcattta tgtctcatct gttttttcctt   240
tcggntatat ctttggnttt gaataccaac atttaaaatg atggnatttt atcttttaaa   300
cttaaaaatt atttaataca gctatatgga ccttataaaa ttgatttctt atttattatt   360
agacattact actaaaagg                                                379

<210> SEQ ID NO 35
<211> LENGTH: 163
<212> TYPE: DNA
<213> ORGANISM: Homo sapiens

<400> SEQUENCE: 35

```
ctaacccacg attctgagcc ctgagtatgc ctggacattg atgctaacat gaccatgctt      60
gggatgtctc tagctggtct ggggatagct ggagcactta ctcaggtggc tggtgaaatg     120
acacctacga aggaatgagt gctatagaga ggagagagga gtg                       163
```

<210> SEQ ID NO 36
<211> LENGTH: 508
<212> TYPE: DNA
<213> ORGANISM: Homo sapiens
<220> FEATURE:
<221> NAME/KEY: misc_feature
<222> LOCATION: (319)..(507)
<223> OTHER INFORMATION: n = unknown

<400> SEQUENCE: 36

```
cagctgatgt catgtggtgc tgagaagaaa gcagatcaca cttcatcaca gaaagaatgc      60
cttgtgatta tcttctccac atctgaaatt ccttttgaca cctgcattgg gccgactgcc     120
attcccatga ctgctgcacc tgcgttttta gagaatgcct cataacccac tgattctcat     180
tcacagagaa tgggaatacg gaatgaagaa agattccagc agcttataga aggatagcaa     240
tattttggga cagggaaaat cctgtcatac ctcacctctt cctcaggagg agttctgagc     300
tggtcctgct tttcatagnt gtttctttc ttccacttaa gaactcatag attttctta      360 ctgtcctaag gaagtcctta cctctgaggt atctcctcaa tgaatactgt tttcaaggct     420
gaaatagttc attatgttaa taaccttctt tatgttctca gggaaatgct taggtggtgt     480
cacaaaaagg gccttttctt tnctttnc                                        508
```

<210> SEQ ID NO 37
<211> LENGTH: 89
<212> TYPE: DNA
<213> ORGANISM: Homo sapiens

<400> SEQUENCE: 37

```
cttcaaaaag tgtattgtca aacataccta actttcttgc aataaatgca aagaaactg       60 gaacttgaca attataaata gtaatagtg                                        89
```

<210> SEQ ID NO 38
<211> LENGTH: 146
<212> TYPE: DNA
<213> ORGANISM: Homo sapiens

<400> SEQUENCE: 38

```
caatttgtta tagtatagta tcaaatttct atatagattt tataccctcag tggggaaaaa    60 taactgattc caatgacatt cattttgttt tcatctgtga tagtcatgga tgcttttatt     120
ttccttgggg tgctgaaatt gagctg                                          146
```

<210> SEQ ID NO 39
<211> LENGTH: 149
<212> TYPE: DNA
<213> ORGANISM: Homo sapiens

<400> SEQUENCE: 39

```
cctgccaaaa tcctaccaca ggataacatt acaagcaaaa aatttacatg ttccaaagtc      60
```

```
taccacactc aagaagttac taagaactct tgcagaataa aagtcaccat tttagaaatg      120
caaacccact tccaaccttt gcacagtcc                                        149

<210> SEQ ID NO 40
<211> LENGTH: 348
<212> TYPE: DNA
<213> ORGANISM: Homo sapiens
<220> FEATURE:
<221> NAME/KEY: misc_feature
<222> LOCATION: (339)..(339)
<223> OTHER INFORMATION: n = unknown

<400> SEQUENCE: 40
catttttagt gacattttaa aagcagtcag attctataaa tggcaagtaa gcctgaagtg      60
aggatactgc aattttcgga gaaaagaaca gcagctcttt aagtgtttgc attttctatt    120 tgggggggcag ggaactgtca ttcattttgc acaattcttg aactgatgtc agcacccgag   180
tggctcctga atttaagtct gggacgacat ctttttatttt tacatgaatc tttaaacaat   240
tctgtgagca aagtttgtag ctgctggatt attgtctgtc tttatagcaa gttccagtaa   300
accacaagta tggcaaagct tatccaattt tatgcttgna gcagtcag                 348

<210> SEQ ID NO 41
<211> LENGTH: 106
<212> TYPE: DNA
<213> ORGANISM: Homo sapiens

<400> SEQUENCE: 41
ggtagacgta cctgcgtccc agacttgacc aggtggatct cctgttttac tcacgaggac     60
tttcccagga aaaccatgcc actagcaaaa taatataaac aaagga                   106

<210> SEQ ID NO 42
<211> LENGTH: 103
<212> TYPE: DNA
<213> ORGANISM: Homo sapiens

<400> SEQUENCE: 42
tttttttttt tttttggct agaggcatgg atatcctggg aaagctctcc tgagtaaaag     60
acgagagaca cctggtgaag actggaacgc atgtacgtct acc                     103

<210> SEQ ID NO 43
<211> LENGTH: 169
<212> TYPE: DNA
<213> ORGANISM: Homo sapiens

<400> SEQUENCE: 43
ggtcgacgta cctgcgcaat aaagctgtcc attcaattcc aaatactggt tttaaggtat    60
agccactgat attctttcat gtttagaaat tctttctgtt attattcaag aaaatgtttt   120
taatcatgct aataaacttt tttggagatg aaaaaaaaaa aaaaaaaa                169

<210> SEQ ID NO 44
<211> LENGTH: 368
<212> TYPE: DNA
<213> ORGANISM: Homo sapiens

<400> SEQUENCE: 44
gctggttggg ggaattggag gcttctagga ggtggcacgg tgcacgccaa gatggctgtg    60
tccacagagg agctggaggc cacggttcag gaagtcctgg ggagactgaa gagccaccag   120
```

```
ttttttccagt ccacatggga cactgttgcc ttcattgttt tcctcacctt catgggcacc      180
gtgctgctcc tgctgctgct ggtcgtcgcc cactgctgct gctgcagctc ccccgggccc      240
cgcagggaaa gccccaggaa ggaaagaccc aagggagtgg ataacttggc cctggaaccc      300
tgaccctgtg tctcctgccc ggtggcagta acaaagcctt ctgtctgccc agaaaaaaaa      360
aaaaaaaa                                                               368
```

<210> SEQ ID NO 45
<211> LENGTH: 545
<212> TYPE: DNA
<213> ORGANISM: Homo sapiens

<400> SEQUENCE: 45

```
ctaaatctag gtattctggc tgagtgtatc tgggtgggcc agctaaaaat aaacctcatt       60
gaactccagc cccaacccag agaaacatcc agaagagcct tgaattagtg atccaaaacc      120 caggggaaa ggcgacattc tcaccccag cacccccttc acctcacctc aactcctact        180
ctctcggtct ataatcactg ctctctctct ccccaacacc actattgaac aggagcccttt     240 gtcaccaggt ccaagcaatt ccctaaggta tcacaaacaa tggtggatgc aattttacct      300
tactcagtaa ccacgaggct cacatcccta atttcagact ctaccagctc tcaggtgccc      360
tcccaagggg ctgcctgcat gaagatgcct tggaagtagc ccctttcaca atcacaggaa      420
ttaaccccct ggtgttggag gggcctcact ttaagcaatc ccagtagtaa acattggata      480
aatctaaagg ctttctttaa ttttttttttt ctcttcgtaa aggattcaaa gcaggcacag      540
tggtg                                                                  545
```

<210> SEQ ID NO 46
<211> LENGTH: 178
<212> TYPE: DNA
<213> ORGANISM: Homo sapiens

<400> SEQUENCE: 46

```
ccctgggaga gaagtttgaa gaaaccacag ctgatggcag aaaaactcag actgtctgca       60
actttacaga tggtgcattg gttcagcatc aggagtggga tgggaaggaa agcacaataa      120
caagaaaatt gaaagatggg aaattagtgg tggagtgtgt catgaacaat gtcacctg        178
```

<210> SEQ ID NO 47
<211> LENGTH: 122
<212> TYPE: DNA
<213> ORGANISM: Homo sapiens

<400> SEQUENCE: 47

```
catgagcagg ctcagcctag gggaataatt gccaacaaac acttttggga agcctgggac       60
catggctctg ccaggaatct gtgacatctc cagggcatca tttgagtcct gccttctcaa      120
ag                                                                     122
```

<210> SEQ ID NO 48
<211> LENGTH: 376
<212> TYPE: DNA
<213> ORGANISM: Homo sapiens

<400> SEQUENCE: 48

```
ctcttcttat gctaatatgc tctgggctgg agaaatgaaa tcctcaagcc atcaggattt       60
gctatttaag tggcttgaca actgggccac caaagaactt gaacttcacc ttttaggatt      120
tgagctgttc tggaacacat tgctgcactt tggaaagtca aaatcaagtg ccagtggcgc      180
```

```
cctttccata gagaatttgc ccagctttgc tttaaaagat gtcttgtttt ttatatacac      240
ataatcaata ggtccaatct gctctcaagg ccttggtcct ggtgggattc cttaccaat       300 tactttaatt aaaaatggct gcaactgtaa gaaccctgtg ctgatatatt tgcaactatg      360
ctcccattta caaatg                                                     376
```

<210> SEQ ID NO 49
<211> LENGTH: 418
<212> TYPE: DNA
<213> ORGANISM: Homo sapiens

<400> SEQUENCE: 49

```
ccttccgaaa tacttcctcc aggtggcagc accaagaata tttctggaag catgtgatga      60
gttgtgtgat gaagatagag cccattgtgc tgtctctcca ggacacgttg tgtggcgttg     120
aagagcagaa agcaatgaag tccttctcca cgtgggtctt gtaaacagca tcttcctcca     180
ggttctcaga tgactgtgaa gaggccactt ccaaggatgc tggagagtct ctgacccaca     240
gttccccacg gtttgcacct ctgcaggcct ggacaatgat gaccttgggt ttgtccttca     300
gactgaggca gttgcggttg ttgaatatct ggaagatggt gtcataaagc agcacatctg     360
gttttttctc atcatgcaca gttccgcaga ttccctccag gatgccatga gacatggg       418
```

<210> SEQ ID NO 50
<211> LENGTH: 413
<212> TYPE: DNA
<213> ORGANISM: Homa sapiens

<400> SEQUENCE: 50

```
ctcattgaac ttgagctccg agtcctgatt cacatccaag ctcttcatct tctcatcaag      60
agagcccaca tccttgagca gatggggcaa ctgctgggta accagctctt gaactcgtt     120 gacgctgagg ctatccttcc ggccctcctg ccttgcaaag gtgaagaagg tggtgaccac     180
ggtctcaatg gactcctcta gctctgtcag tggttctgct gccattagga ccctgaggcc     240
aaagctgatg tcctcaaggg gctagctgac cttttgtcagg gctgacctct cctcagcggc     300
agcagggcag agtgctgaac ccaggacccc acagatcctc cccgctcctg tctcccggtg     360
acaagggtcc tggaacgggg cgtctctgac tccctgctcc aggacgggtt tag            413
```

<210> SEQ ID NO 51
<211> LENGTH: 157
<212> TYPE: DNA
<213> ORGANISM: Homo sapiens

<400> SEQUENCE: 51

```
tttttttttt ttttttggt tacggcagca cttttatttt tccttacaca atgacgtgtt       60 gctgggcct aatgttctca cataacagta gaaaaccaaa atttgttgtc atctcttcaa     120
agaatcgaga attgcgtaca aaaaaaaaaa aaaaaaa                              157
```

<210> SEQ ID NO 52
<211> LENGTH: 165
<212> TYPE: DNA
<213> ORGANISM: Homo sapiens

<400> SEQUENCE: 52

```
ctctccagtt tgcacctgtc cccaccctcc actcagctgt cctgcagcaa acactccacc      60
ctccaccttc catttccccc cactactgca gcacctccag gcctgttgct atagagccta     120
```

```
cctgtatgtc aataaacaac agctgaagca aaaaaaaaaa aaaaa                    165
```

<210> SEQ ID NO 53
<211> LENGTH: 201
<212> TYPE: DNA
<213> ORGANISM: Homo sapiens

<400> SEQUENCE: 53

```
ggtacgacgg acctgcggag actcctgccc tgttgtgtat agatgcaaga tatttatata    60
tatttttggt tgtcaatatt aaatacagac actaagttat agtatatctg acaagccaa    120
cttgtaaata caccacctca ctcctgttac ttacctaaac agatataaat ggctggtttt    180
tagaaaaaaa aaaaaaaaaa a                                             201
```

<210> SEQ ID NO 54
<211> LENGTH: 342
<212> TYPE: DNA
<213> ORGANISM: Homo sapiens

<400> SEQUENCE: 54

```
ggctggagca ggagattgcc acctaccgcc gcctgctgga gggagaggat gcccacctga    60
ctcagtacaa gaaagaaccg gtgaccaccc gtcaggtgcg taccattgtg aagaggtcc    120
aggatggcaa ggtcatctcc tcccgcgagc aggtccacca gacccaccgc tgaggactca    180
gctaccccgg ccggccaccc aggaggcagg gaggcagccg ccccatctgc cccacagtct    240
ccggcctctc cagcctcagc cccctgcttc agtcccttcc ccatgcttcc ttgcctgatg    300
acaataaagc ttgttgactc agctaaaaaa aaaaaaaaaa aa                      342
```

<210> SEQ ID NO 55
<211> LENGTH: 103
<212> TYPE: DNA
<213> ORGANISM: Homo sapiens

<400> SEQUENCE: 55

```
ttttttttt tttttttgct agtggcatgg ttttcctggg aaagtcctcc tgagtaaaag    60
aggagagaca cctggtgaag actgggacgc aggtacgtct acc                     103
```

<210> SEQ ID NO 56
<211> LENGTH: 873
<212> TYPE: DNA
<213> ORGANISM: Homo sapiens

<400> SEQUENCE: 56

```
ctccagcgat atgttcaact atgaagaata ctgcaccgcc aacgcagtca ctgggccttg    60
ccgtgcatcc ttcccacgct ggtactttga cgtggagagg aactcctgca ataacttcat    120
ctatggaggc tgccgggggca ataagaacag ctaccgctct gaggaggcct gcatgctccg    180
ctgcttccgc cagcaggaga atcctcccct gccccttggc tcaaaggtgg tggttctggc    240
ggggctgttc gtgatggtgt tgatcctctt cctgggagcc tccatggtct acctgatccg    300
ggtggcacgg aggaaccagg agcgtgccct gcgcaccgtc tggagctccg agatgacaa    360
ggagcagctg gtgaagaaca catatgtcct gtgaccgccc tgtcgccaag aggactggga    420
agggagggga gactatgtgt gagcttttt taaatagagg gattgactcg gatttgagtg    480
atcattaggg ctgaggtctg tttctctggg aggtaggacg gctgcttcct ggtctggcag    540
ggatgggttt gctttggaaa tcctctagga ggctcctcct cgcatggcct gcagtctggc    600
agcagcccg agttgtttcc tcgctgatcg atttctttcc tccaggtaga gttttctttg    660
```

```
cttatgttga attccattgc ctctttctc atcacagaag tgatgttgga atcgtttctt    720
ttgtttgtct gatttatggt tttttaagt ataaacaaaa gttttttatt agcattctga    780
aagaaggaaa gtaaaatgta caagtttaat aaaaagggc cttcccttt agaataaatt     840 tcagcatgtg ctttcaaaaa aaaaaaaaaa aaa                                873

<210> SEQ ID NO 57
<211> LENGTH: 325
<212> TYPE: DNA
<213> ORGANISM: Homo sapiens

<400> SEQUENCE: 57
aaagagggcg gcaggggcct ggagatcctc ctgcagacca cgcccgtcct gcctgtggcg    60
ccgtctccag gggctgcttc ctcctggaaa ttgacgaggg gtgtcttggg cagagctggc   120
tctgagcgcc tccatccaag gccaggttct ccgttagctc ctgtggcccc accctgggcc   180
ctgggctgga atcaggaata ttttccaaag agtgatagtc ttttgctttt ggcaaaactc   240
tacttaatcc aatgggtttt tctctgtaca gtagattttc caaatgtaat aaactttaat   300
ataaagtaaa aaaaaaaaa aaaaa                                         325

<210> SEQ ID NO 58
<211> LENGTH: 207
<212> TYPE: DNA
<213> ORGANISM: Homo sapiens

<400> SEQUENCE: 58
ggaccggaac aaggaccagg aggtgaactt ccaggagtat gtcaccttcc tgggggcctt    60
ggctttgatc tacaatgaag ccctcaaggg ctgaaaataa atagggaaga tggagacacc   120 ctctggggt cctctctgag tcaaatccag tggtgggtaa ttgtacaata aatttttttt   180
ggtcaaattt aaaaaaaaaa aaaaaaa                                      207

<210> SEQ ID NO 59
<211> LENGTH: 405
<212> TYPE: DNA
<213> ORGANISM: Homo sapiens

<400> SEQUENCE: 59
caggagacca tccgcgtcac caagccctgc accccaaga ccaaagcaaa ggccaaagcc     60
aagaagggga agggaaagga ctagacgcca agcctggatg ccaaggagcc cctggtgtca   120 catgggcct ggcccacgcc ctccctctcc caggcccgag atgtgaccca ccagtgcctt    180
ctgtctgctc gttagcttta atcaatcatg ccctgccttg tccctctcac tccccagccc   240 caccctaag tgcccaaagt ggggagggac aagggattct gggaagcttg agcctccccc   300
aaagcaatgt gagtcccaga gcccgctttt gttcttcccc acaattccat tactaagaaa   360
cacatcaaat aaactgactt ttccccccca aaaaaaaaa aaaaa                    405

<210> SEQ ID NO 60
<211> LENGTH: 119
<212> TYPE: DNA
<213> ORGANISM: Homo sapiens

<400> SEQUENCE: 60
```

-continued

```
tttttttttt tttttgaaga caacttttag aaactgatgt ttattttcca tcaaccattt      60
ttccatgctg cttaagagcc tatgcaagaa cagcttaaga ccagtcagtg gttgaagtc      119

<210> SEQ ID NO 61
<211> LENGTH: 317
<212> TYPE: DNA
<213> ORGANISM: Homo sapiens

<400> SEQUENCE: 61
gactaccaga ccaacaaagc caagcatgat gagctgacct atttctgatc ctgactttgg      60
acaaggccct tcagccagaa gactgacaaa gtcatcctcc gtctaccaga gcgtgcactt     120
gtgatcctaa aataagcttc atctccgggc tgtgccoctt ggggtggaag gggcaggatt     180
ctgcagctgc ttttgcattt ctcttcctaa atttcattgt gttgatttct ttccttccca     240
ataggtgatc ttaattactt tcagaatatt ttcaaaatag atatattttt aaaatcctta     300
caaaaaaaaa aaaaaaa                                                    317

<210> SEQ ID NO 62
<211> LENGTH: 229
<212> TYPE: DNA
<213> ORGANISM: Homo sapiens

<400> SEQUENCE: 62
aaggcttatt ccatccggac cgcatccgcc agtcgcagga gtgcccgcga ctgagccgcc      60
tcccaccact ccactcctcc agccaccacc cacaatcaca agaagattcc caccoctgcc     120 tcccatgcct ggtcccaaga cagtgagaca gtctggaaag tgatgtcaga atagcttcca     180
ataaagcagc ctcattctga ggcctgagtg aaaaaaaaaa aaaaaaaa                   229

<210> SEQ ID NO 63
<211> LENGTH: 465
<212> TYPE: DNA
<213> ORGANISM: Homo sapiens

<400> SEQUENCE: 63
agcggctatg caggtggtct gagctcggcc tatgggggcc tcacaagccc cggcctcagc      60
tacagcctgg gctccagctt tggctctggc gcgggctcca gctccttcag ccgcaccagc     120
tcctccaggg ccgtggttgt gaagaagatc gagacacgtg atgggaagct ggtgtctgag     180
tcctctgacg tcctgcccaa gtgaacagct gcggcagccc ctcccagcct acccctcctg     240
cgctgcccca gagcctggga aggaggccgc tatgcagggt agcactggga acaggagacc     300
cacctgaggc tcagccctag ccctcagccc acctggggag tttactacct ggggaccccc     360
cttgcccatg cctccagcta caaaacaatt caattgcttt ttttttttg gtccaaaata     420 aaacctcagc tagctctgcc aatgtcaaaa aaaaaaaaa aaaaa                      465
```

METHODS OF DIAGNOSING BLADDER CANCER

CROSS-REFERENCE RELATED TO PATENT APPLICATIONS

The present application claims the benefit of and is a continuation-in-part of PCT application PCT/US00/41005, filed Sep. 27, 2000, which in turn claims the benefit of priority under U.S.C. §119(e) of U.S. Provisional Patent Application No. 60/156,153, filed Sep. 27, 1999, both of which are hereby incorporated herein by reference.

BACKGROUND OF THE INVENTION

1. Field of the Invention

The present invention relates to the identification of polynucleotide sequences that are differentially expressed in bladder cancer. More specifically, the present invention relates to the use of the sequences and gene products for diagnosis and as probes.

2. Description of Related Art

Bladder cancer is the second most-common genitourinary cancer in the United States, with only prostate cancer being more frequently diagnosed. Bladder cancer accounts for approximately two percent of all malignant tumors and approximately seven percent of all urinary tract malignancies in U.S. men. Over 54,000 new cases were estimated to be diagnosed in the United States in 1998, with approximately 12,500 deaths predicted [American Cancer Society, 19981]. The prevalence of bladder cancer is higher in industrialized nations, perhaps reflecting increased exposure to environmental carcinogens. Men are three times more frequently affected than women. The disease usually occurs between 60–70 years of age and the age-adjusted bladder cancer rate in white men is almost twice that of black men. Most bladder cancers (over 90%) are carcinomas of the transitional epithelium of the bladders mucosal lining (transitional cell carcinoma (TCC)). Although 90 percent of the cases are localized at diagnosis, up to 80 percent recur.

A number of etiological factors are associated with the development of bladder cancer, but in industrialized countries, cigarette smoking is the most significant. Specific chemicals have also been identified as causing bladder cancer, as have a number of occupational exposures to less well-defined specific agents. Treatment with cytostatic drugs, especially cyclophosphamide, is associated with increased risk of bladder cancer, as is treatment with radiotherapy for uterine cancer.

Bladder cancer is a potentially preventable disease, with a significant morbidity and mortality in many parts of the world.

Tumors are graded according to the degree of cellular abnormality, with the most atypical cells being designated as high-grade (i.e., G3 grade) tumors. The major prognostic factors in carcinoma of the bladder are the depth of invasion into the bladder wall and the degree of differentiation of the tumor. The higher the grade of the tumor at the diagnosis, the higher the incidence of death from the disease within two years.

The stage of development of the tumor is significant in estimating disease prognosis. Most superficial, non-invasive tumors are papillary tumors which do not invade the *lamina propria*, and are classified as non-invasive TCC, i.e., "Ta" tumors, and they can recur, but nearly 70% will not progress further. A tumor which does not invade the muscle but does enter the *lamina propria* presents in many cases a worse prognosis. Such tumors are also classified as non-invasive TCC but are termed T1 tumors. Most superficial tumors are well differentiated and classified as G1 grade tumors. Patients in whom superficial tumors are less differentiated, large, multiple, or associated with carcinoma in situ in other areas of the bladder mucosa, (classified as G2–G3 tumors) are at greatest risk for recurrence and the development of invasive cancer. Invasive bladder tumors tend to spread rapidly to the regional lymph nodes and then into adjacent structures. Overall, the five-year survival rate of TCC is 76 percent for whites and 55 percent for blacks.

One of the management problems is the fact that carcinoma of the bladder is frequently multifocal. The entire bladder epithelium and the lining of the entire urothelial cell tract can undergo malignant change. After apparently successful treatment of a bladder lesion, new tumors can occur at the same site (recurrence) or in other urothelial cells in the bladder. Approximately 30 percent of bladder carcinomas present as multiple lesions at the time of initial diagnosis. The early diagnosis of bladder cancer is central to the effective treatment of TCC. Presently, the detection of bladder tumors relies on intravenous pyelogram or other contrast studies to rule out urothelial involvement in the kidneys or ureters, and invariably cystoscopy which remains the accepted standard for diagnosis of mucosal abnormalities. There are no presently reliable methods available to easily and specifically identify the presence of bladder cancer cells. A variety of new technologies and potential tumor markers are being studied in bladder cancer and some are being translated into clinical use.

It is important to realize that all available results of the diagnostic value of tumor markers do not allow firm clinical recommendations, but tests based on biomarkers undoubtedly influence the management of bladder cancer in the near future. Several new markers have been already identified and even approved for use (e.g. bladder tumor antigen (BTA) markers, NMP22, FDP). However, their clinical use is limited [Grossman, 1983], due to sensitivity and specificity problems in conjunction with cystoscopic examination.

Furthermore, due to the high rate of disease recurrence, follow-up of TCC patients is obligatory. There is a need to eliminate the invasive cytoscopy method of diagnosis and of follow-up and replace it with a reliable and noninvasive method of diagnosis.

Approximately 70–80 percent of patients with ne diagnosed bladder cancer present with superficial, non-invasive bladder tumors. Those who do are often curable. Tumor patients with deeply invasive disease can sometimes be cured by complete surgical removal of the bladder, irradiation, or a combination of modalities that include chemotherapy, however the five-year survival rate is less likely for such tumors. It is therefore of major importance to detect new tools that aid in both the initial early diagnosis and in follow-up of non-invasive TCC tumors.

Adverse prognostic features associated with a greater risk of disease progression include the presence of multiple aneuploid cell lines, nuclear p53 overexpression, and expression of the Lewis-x blood group antigen [Hudson and Herr, 1995; Lacombe et al., 1996]. It has been postulated that p53 can be useful for predicting the level of aggression of the tumor and to identify patients who will not benefit from chemotherapy. However, only a very small, select group of patients with invasive disease can benefit from this approach [Ozen, 1981].

Several treatment methods (i.e., transurethral surgery, intravesical medications, and cystectomy) have been used in the management of patients with superficial tumors, and each method can be associated with five-year survival in 55–80 percent of patients treated [Hudson and Herr, 1995; Torti and Lum, 1984]. Invasive tumors that are confined to the bladder muscle on pathologic staging after radical cystectomy are associated with an approximately 75 percent, five-year progression-free rate of survival. Patients with more deeply invasive tumors (which are also usually less well differentiated) experience five-year survival rates of 2040 percent following radical cystectomy. When the patient presents with a locally extensive tumor that invades pelvic viscera or with metastases to lymph nodes or distant sites, a five-year survival rate: is uncommon, but considerable symptomatic palliation can still be achieved.

Surgery is the main treatment method. The extent of surgery is dependent on the pathological stage of the disease. Early disease is generally treated by intravesical chemotherapy and transurethral resection. Locally invasive disease can usually be managed only by radical cystectomy and urinary diversion. Definitive (curative) radiotherapy is generally reserved for bladder cancer patients who are not candidates for surgery. For superficial, low-grade disease, chemotherapy is applied intravesically (directly into the bladder) to concentrate the drug at the tumor site and eliminate any residual tumor mass after resection. Systemic chemotherapy can also be used to manage advanced bladder cancer; compete response rates of 30–50 percent have been reported. Single agent chemotherapy has demonstrated limited success However, even following surgery and resection of non-invasive TCC tumors, frequent follow-up is required (every 3 months) in both non-invasive and invasive cases.

It would therefore be useful to be able to identify early stage TCC in bladder cancer which has a significantly higher cure rate and generally does not require surgery. In addition, it would be useful to identify markers that can be employed for early diagnosis and follow-up of both non-invasive and invasive TCC, as an efficient and non-invasive alternative to cytoscopy.

SUMMARY OF THE INVENTION

According to the present invention, there is provided a method of diagnosing the presence of bladder cancer in a patient by analyzing a patient derived sample for the presence of a least one expressed gen rein the high level of expression of the gene is indicative of bladder cancer. Also provided by the present invention is a polynucleotide sequence whose expression is indicative of bladder cancer. A marker for bladder cancer is also provided. There are also provided methods of diagnosing bladder cancer by screening for the presence of at least one expressed gene wherein the presence of the expressed gene is indicative of bladder cancer. Methods of treating and regulating bladder cancer-associated pathology by administering to a patient a therapeutically effective amount of a chemical compound which inhibits a gene comprising the nucleic acids sequences of the present invention are also provided.

DESCRIPTION OF THE INVENTION

Figure 1:
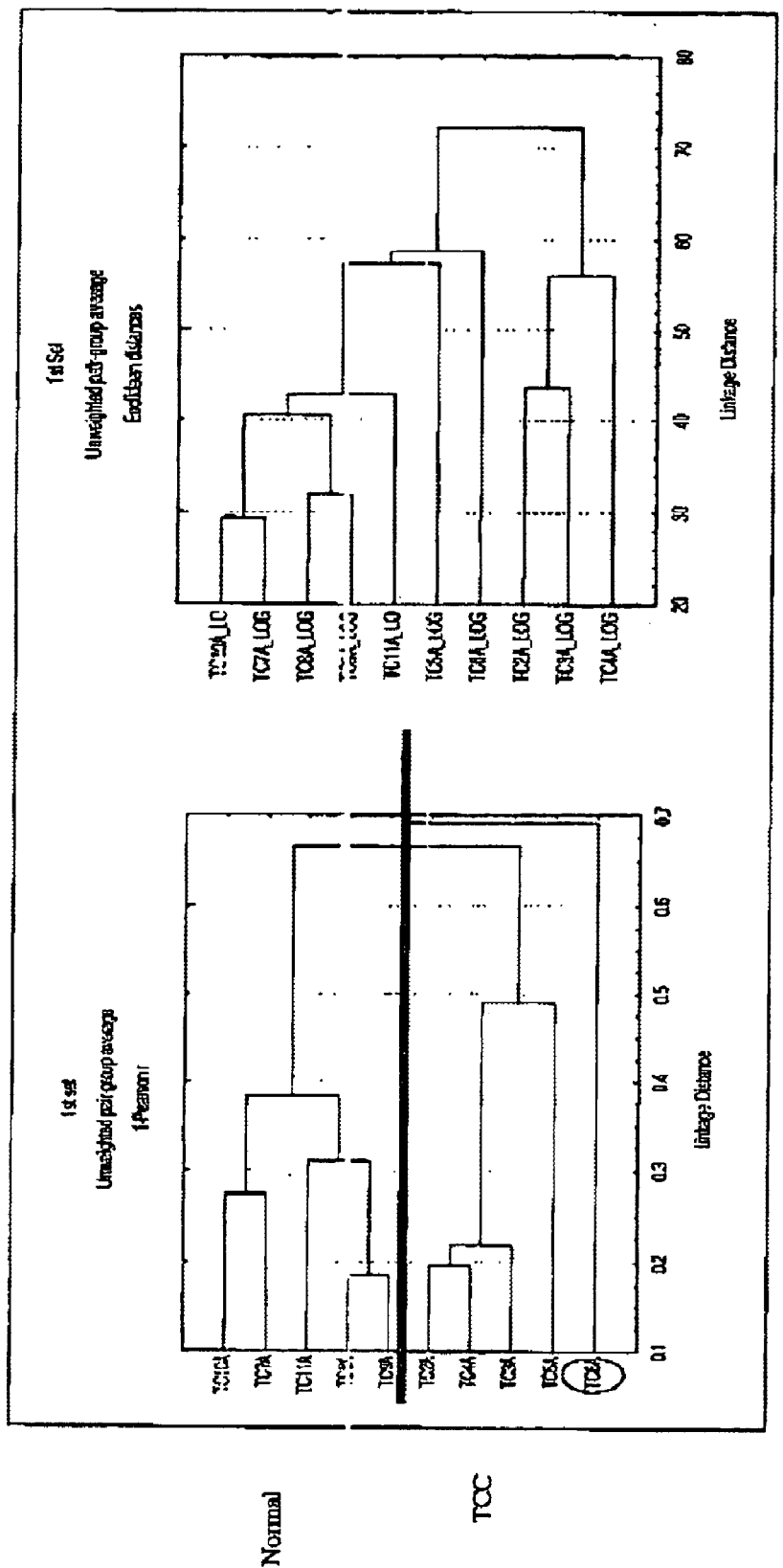
FIG. 1: This figure shows relationships between hybridizations' hierarchical clustering of Set #1 hybridizations. Either the Pearson correlation coefficient or a standard Euclidean distance was used as the distance measure between differential hybridization vectors. Hybridizations were clustered according to these distances by average linkage hierarchical clustering. Missing values were deleted on a case-wise basis. Clusters of Missing values hybridizations can be identified and evaluated in light of existing knowledge.
Figure 2:
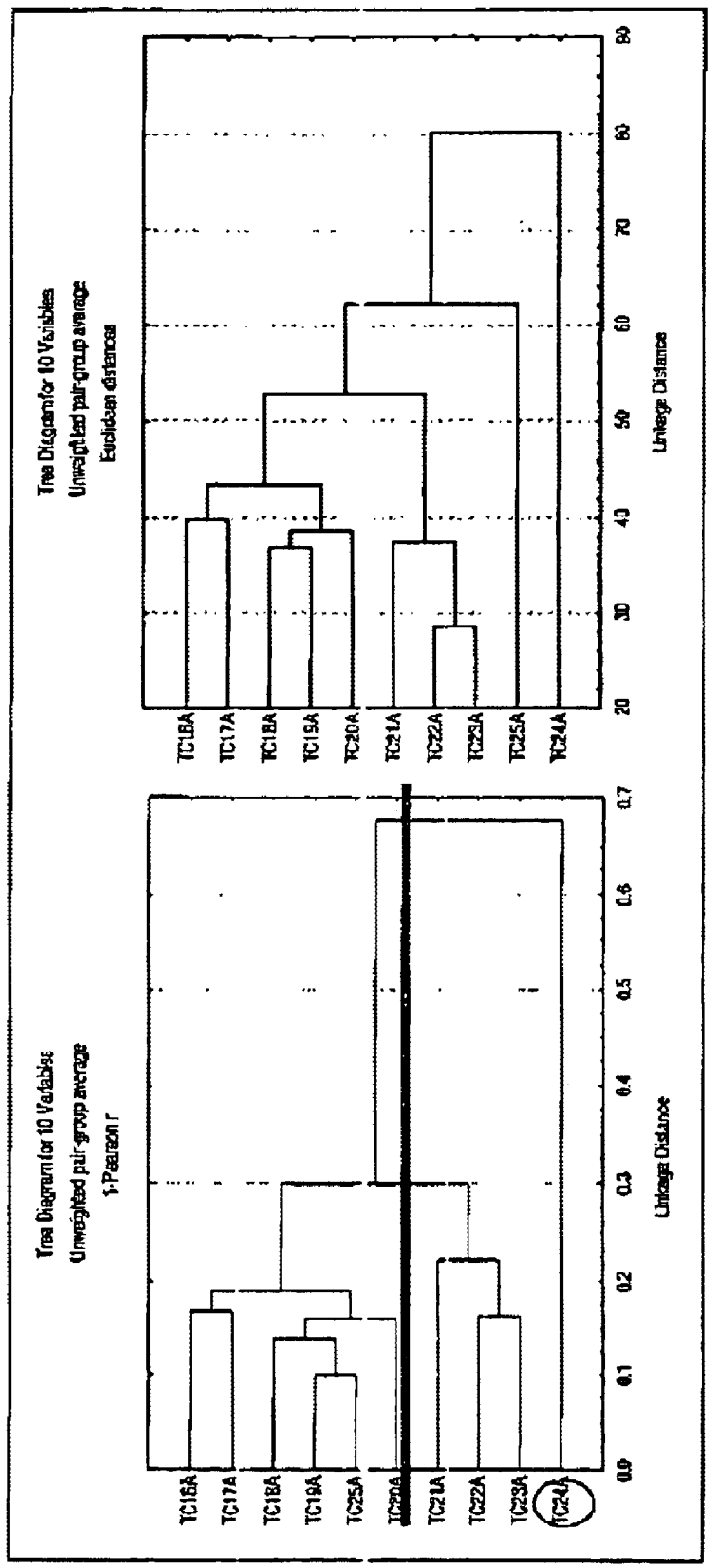
FIG. 2: This figure shows relationships between hybridizations' hierarchical clustering of Set #2 hybridizations. Either the Pearson correlation coefficient or a standard Euclidean distance was used as the distance measure between differential hybridization vectors. Hybridizations were clustered according to these distances by average linkage hierarchical clustering. Missing values were deleted on a case-wise basis. Clusters of Missing values hybridizations can be identified and evaluated in light of existing knowledge.
Figure 3:
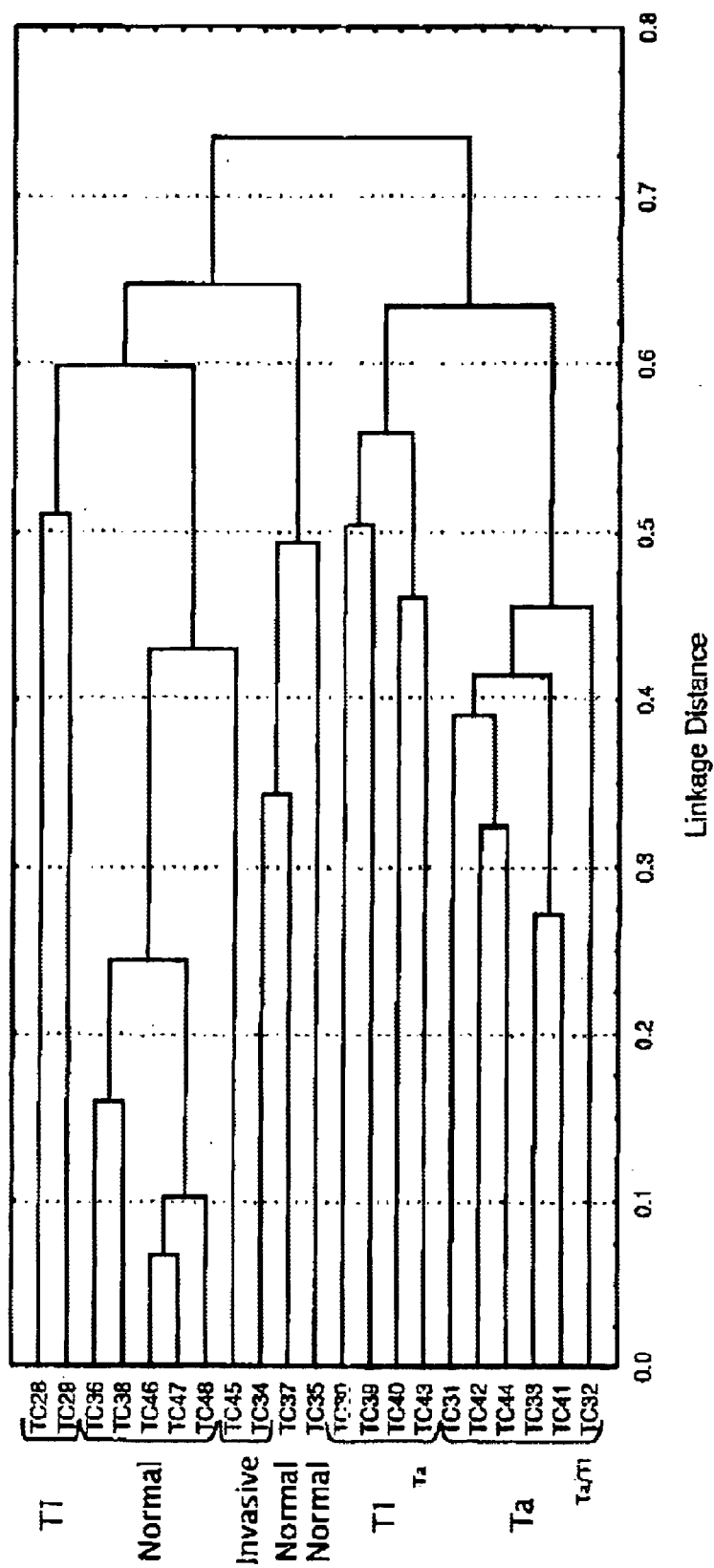
FIG. 3: This figure shows relationships between hybridizations' hierarchical clustering of Set #3 hybridizations. The figure is a tree diagram for 21 variables with unweighted pair-group average. The Pearson correlation coefficient was used as the distance measure between differential hybridization vectors. Hybridizations were clustered according to these distances by average linkage hierarchical clustering. Missing values were deleted on a case-wire basis. Clusters of Missing values hybridizations can be identified and evaluated in light of existing knowledge.
Figure 4:
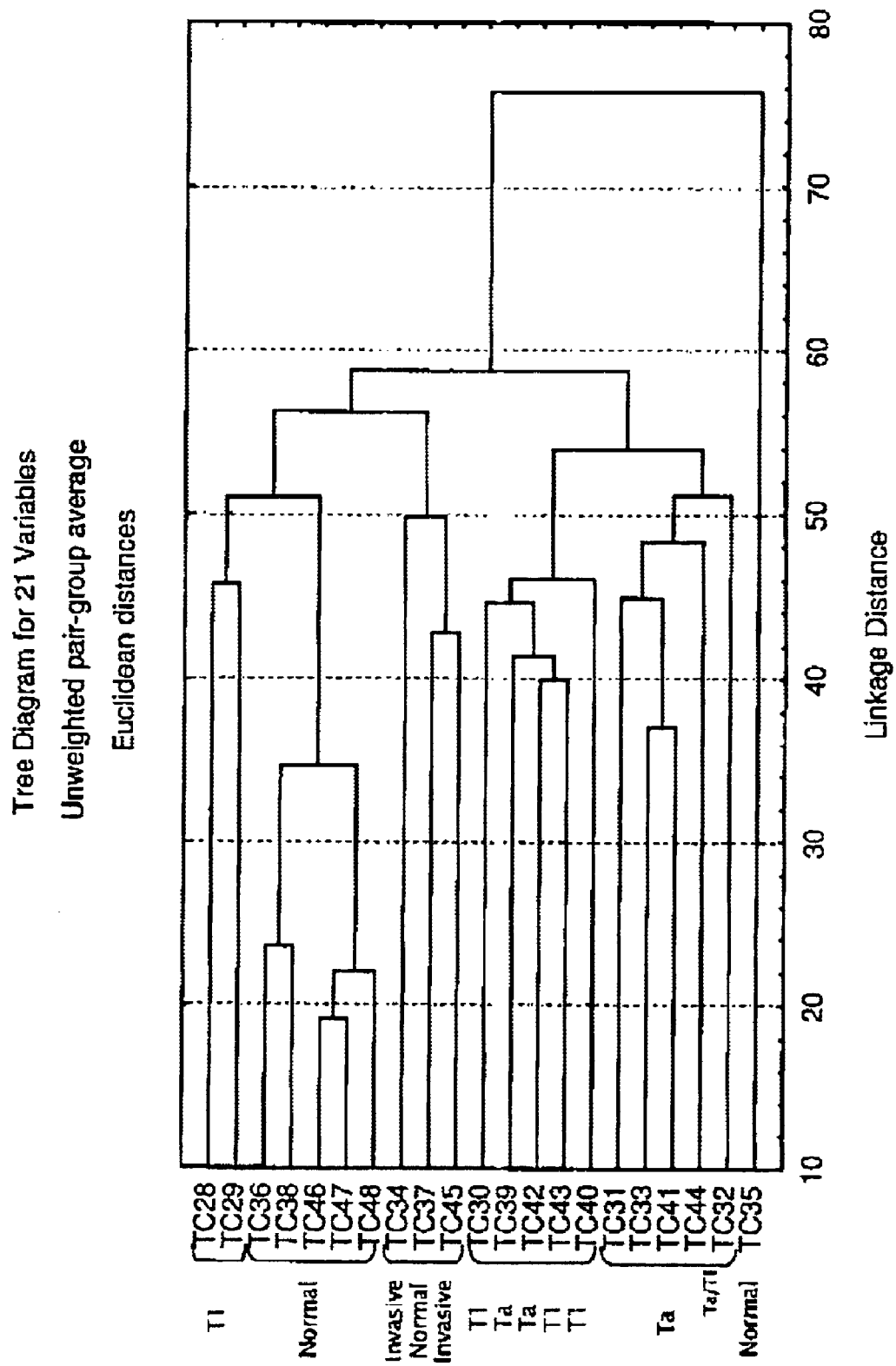
FIG. 4: This figure shows relationships between hybridizations' hierarchical clustering of Set #3 hybridizations. The figure is a tree diagram for 21 variables with unweighted pair-group average. The standard Euclidean distance was used as the distance measure between differential hybridization vectors. Hybridizations were clustered according to these distances by average linkage hierarchical clustering. Missing values were deleted on a case-wise basis. Clusters of Missing values hybridizations can be identified and evaluated in light of existing knowledge.
Figure 5:
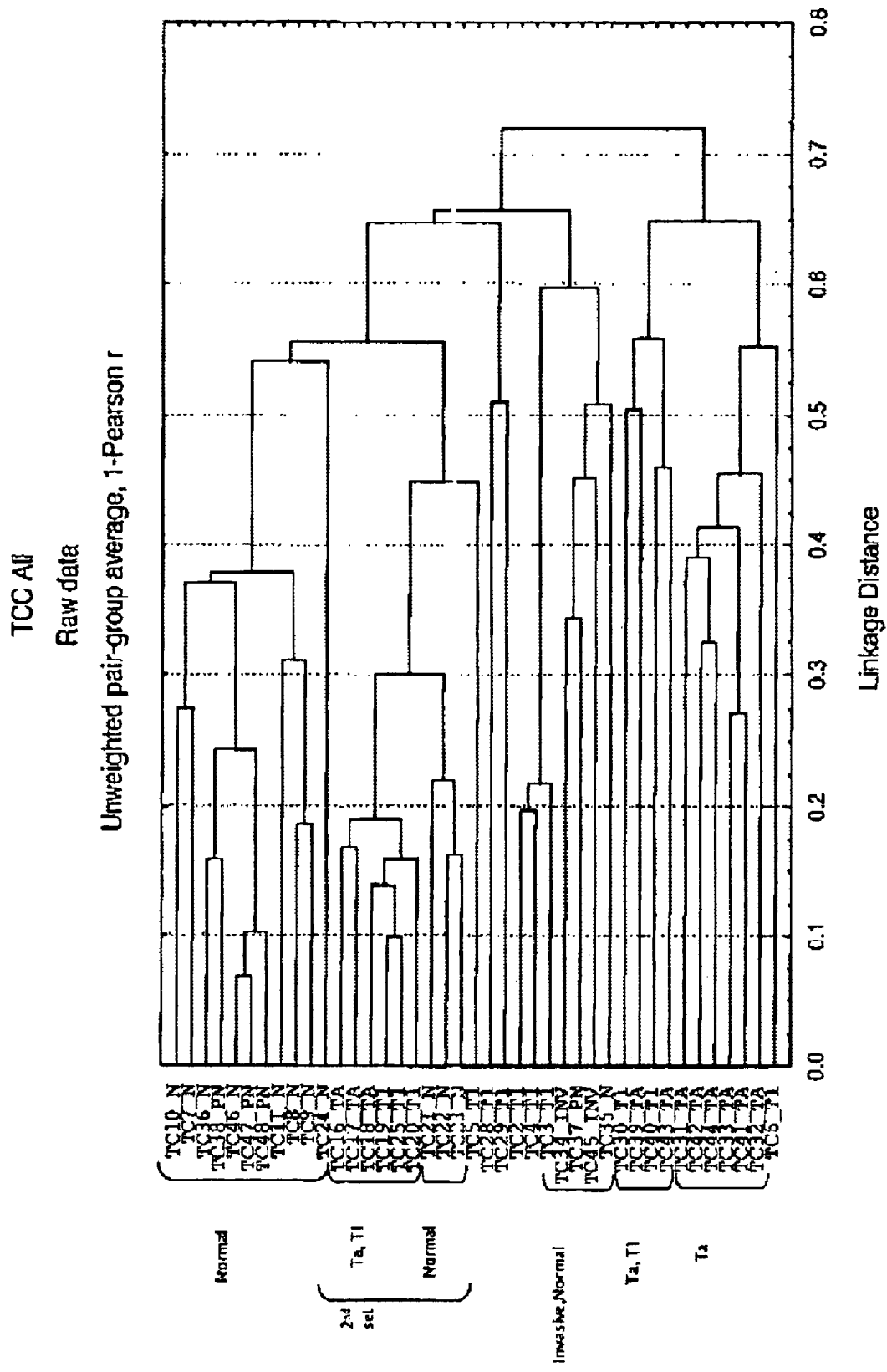
FIG. 5: This figure shows relationships between hybridizations' hierarchical clustering for all TCC sample hybridizations. The figure includes raw data with unweighted pair-group average. The Pearson correlation coefficient was used as the distance measure between differential hybridization vectors. Hybridizations were clustered according to these distances by average linkage hierarchical clustering. Missing values were deleted on a case-wise basis. Clusters of Missing values hybridizations can be identified and evaluated in light of existing knowledge.
Figure 6:
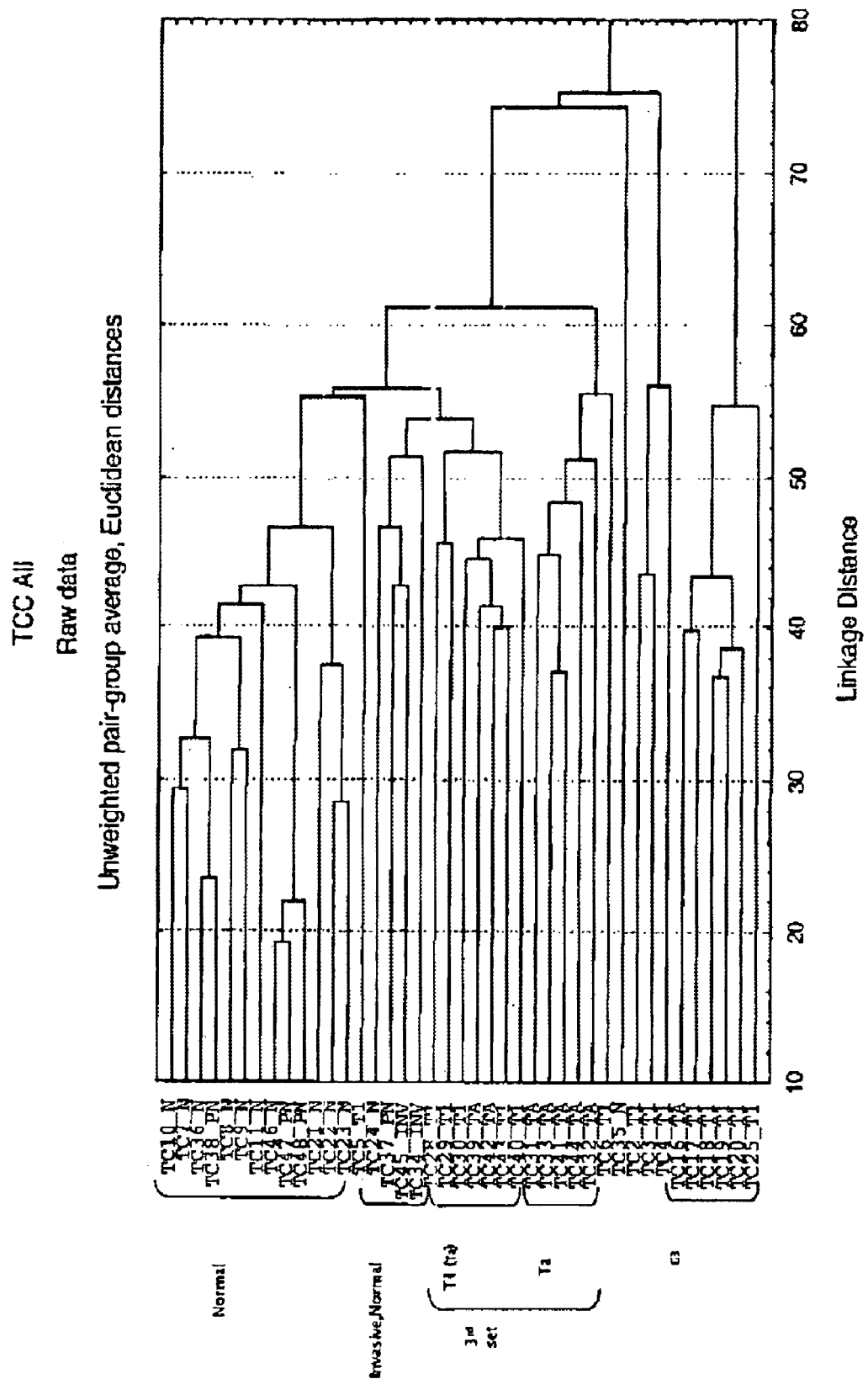
FIG. 6: This figure shows relationships between hybridizations' hierarchical clustering for all TCC sample hybridizations. The figure includes raw data with unweighted pair-group average. The standard Euclidean distance was used as the distance measure between differential hybridization vectors. Hybridizations were clustered according to these distances by average linkage hierarchical clustering. Missing values were deleted on a case-wise basis. Clusters of Missing values hybridizations can be identified and evaluated in light of existing knowledge.

According to the present invention, purified, isolated and cloned nucleic acid sequences associated with bladder cancer are provided. More specifically, the polynucleotides of the present invention are described in Tables 1, 2, and 5 and the corresponding sequences are set forth in Tables 3, 4 and 6 respectively.

When referring to bladder cancer, both invasive and noninvasive forms are included. Bladder cancers can also be referred to as transitional cell carcinomas or "TCC".

The present invention further provides a method of diagnosing the presence of bladder cancer in a patient, including the steps of analyzing a tissue sample from the patient for the presence of at least one expressed gene (up-regulated) wherein the mRNA from the expressed gene hybridizes to at least one of the sequences in Tables 1 or 2, with hybridization occurring under conditions sufficiently stringent to require at least 95% base pairing.

Further the present invention provides antibodies directed against the gene products of the sequences of the present invention. The antibodies can be either monoclonal, polyclonal or recombinant and be used in immunoassays as described in the Methods herein below.

By regulate or modulate or control is meant that the process is either induced or inhibited to the degree necessary to effect a change in the process and the associated disease state in the patient. Whether induction or inhibition is being contemplated is apparent from the process and disease being treated and is known to those skilled in the medical arts. The resent invention identifies genes for gene therapy, diagnostics and therapeutics that have direct causal relationships between a disease and its related pathologies and up- or down-regulator (responder) genes. That is, the present invention is initiated by a physiological relationship between cause and effect.

The present invention identifies polynucleotides named in Tables 1 and 2, and set forth in Tables 3 and 4 respectively; that can be utilized diagnostically in bladder cancer. Polynucleotides named in Table 1 were found to match sequences in data banks and were newly found in the present application to be upregulated in TCC. The polynucleotides named in Table 2 are either genes with unknown protein product or of unknown genes. All the polynucleotides named in both Tables 1 and 2 were found to be associated with TCC relative to normal bladder samples. The polynucleotides named in Table 5 have their corresponding sequences set forth in Table 6, some of which are novel.

Where the sequences are partial sequences, they are markers or probes for genes that are regulated in bladder carcinoma. By "regulated" it is meant that the genes can be either upregulated or downregulated, depending upon the specific gene. In general these partial sequences are designated "Expressed Sequence Tags" (ESTs) and are markers for the genes actually expressed in vivo and are ascertained as described herein. Generally, ESTs comprise DNA sequences corresponding to a portion of nuclear encoded mRNA. The EST has a length that allows for PCR (polymerase chain reaction), use as a hybridization probe and is a unique designation for the gene with which it hybridizes (generally under conditions sufficiently stringent to require at least 95% base pairing).

For a detailed description and review of ESTs and their functional utility see WO 93/00353 which is incorporated in its entirety by reference. WO 93/00353 further describes how the EST sequences can be used to identify the transcribed genes. The Example herein also describes a method of identification. The present invention also provides a method of diagnosing the presence of bladder cancer in a patient, by the expression of at least one expressed gene (up-regulated) identified by the polynucleotides of the present invention set forth in Tables 1–6. Methods of identification of hybridization results can include, but are not limited to, immunohistochemical staining of the tissue samples. Further for identification of the gene, in situ hybridization, Southern blotting, single strand conformational polymorphism (SSCP), restriction endonuclease fingerprinting (REF), PCR amplification and DNA-chip analysis using nucleic acid sequence of the present invention as probes/primers can be used.

The present invention further provides proteins encoded by the identified genes. The present invention further provides antibodies directed against these proteins. The present invention further provides transgenic animals and cell lines carrying at least one expressible gene identified by the present invention. The present invention further provides knock-out eukaryotic organisms in which at least one nucleic acid sequences as identified by the probes of the present invention and prepared as described in the Methods.

The present invention provides a method of diagnosing bladder cancer, in particular TCC, in a subject which comprises determining in a sample from the subject the level of expression of at least one polypeptide-encoding polynucleotide, wherein a higher level of expression of the polynucleotide compared to the level of expression of the polynucleotide in a subject free of bladder cancer is indicative of bladder cancer, and wherein the polypeptide-encoding polynucleotide comprises a polynucleotide selected from the group consisting of
  (a) the polynucleotides listed in Tables 3, 4 and 6;
  (b) polynucleotides having sequences that differ from the polynucleotides in (a), without changing the polypeptide encoded thereby; and (c) polynucleotides which are at least 70% homologous to the polynucleotides of (a).

In a preferred method of the invention, the analyzing step comprises using mRNA from the expressed gene to hybridize to at least one of the sequences in Tables 3, 4 and 6. In other preferred methods of the invention, the analyzing step comprises using RT-PCR technology or using a specific antibody to detect the presence of a polypeptide encoded by said polynucleotide. The present invention also provides a method of diagnosing of diagnosing stage Ta or stage T1 in TCC, which comprises determining in a sample from the patient the level of expression of at least one polypeptide-encoding polynucleotide, wherein a higher level of expression of the polynucleotide compared to the level of expression of the polynucleotide in a patient free of bladder cancer is indicative of stage Ta or stage T1, and wherein the polypeptide-encoding polynucleotide comprises a polynucleotide selected from the group consisting of
  (a) the polynucleotides listed in Tables 3, 4 and 6;
  (b) polynucleotides having sequences that differ from the polynucleotides in (a), without changing the polypeptide encoded thereby; and (c) polynucleotides which are at least 70% homologous to the polynucleotides of (a).

The present invention also provides isolated polynucleotides which comprise a polynucleotide selected from the group consisting of:
  (a) the novel polynucleotides listed in Tables 4 and 6;
  (b) polynucleotides having sequences that differ from the polynucleotides in (a), without changing the polypeptide encoded thereby; and
  (c) polynucleotides which are at least 70% homologous to the polynucleotides of (a).

The present invention also provides such polynucleotides wherein the polynucleotide comprises a polynucleotide having at least 30, preferably at least 40, nucleotides from the polynucleotides described above.

The present invention also provides compositions comprising the isolated polynucleotides of the invention.

The present invention also provides an isolated polypeptide encoded by a polynucleotide, wherein the polynucleotide comprises a polynucleotide selected from the group consisting of:

(a) the polynucleotides listed in Tables 3, 4 and 6;

(b) polynucleotides having sequences that differ from the polynucleotides in (a), without changing the polypeptide encoded thereby; and (c) polynucleotides which are at least 70% homologous to the polynucleotides of (a).

The present invention also provides such a polypeptide, wherein the polypeptide is a portion which retains the biological activity thereof or a polypeptide which is at least substantially homologous or identical thereto.

The present invention also provides a peptide, wherein the peptide is dominant negative peptide which competes with the biological activity of the polypeptide.

The present invention also provides an antibody which binds to a unique epitope of the polypeptide of the invention. The present invention also provides a method of diagnosing bladder cancer in a patient which comprises determining in a sample from the patient the level of expression of at least one polypeptide, wherein a higher level of polypeptide compared to the level of the polypeptide in a patient free of bladder cancer is indicative of bladder cancer. The method includes using an antibody, preferably wherein the presence of more than one polypeptide is detected by using more than one such antibody. The present invention also provides a method of treating bladder cancer-associated pathology in a subject by administering to the subject a therapeutically effective amount of a chemical compound which inhibits a gene, or polypeptide encoded thereby, which comprises a polynucleotide selected from the group consisting of:

(a) the polynucleotides listed in Tables 3, 4 and 6;

(b) polynucleotides having sequences that differ from the polynucleotides in (a), without changing the polypeptide encoded thereby; and (c) polynucleotides which are at least 70% homologous to the polynucleotides of (a).

The present invention also provides a gene therapy vehicle for delivering a polynucleotide of the invention to a subject, whereby the polynucleotide is expressed-in the target cells of the subject. The present invention also provides isolated antisense oligonucleotides complementary to the polynucleotides of the invention.

The samples from the subjects which are used for diagnosis comprise samples of urine, blood, saliva, tissues and cells of all types; urine samples are preferred. A control sample includes a normal equivalent sample derived from a healthy subject.

The term "antibody" includes polyclonal antibody, single chain antibody, Fab fragment, monoclonal (MAB), polyclonal and recombinant antibodies. A molecule which comprises the antigen-binding portion (CDR) of an antibody specific for a polypeptide, variant or fragment is also included in the term "antibody".

Negative dominant peptide refers to a partial cDNA sequence that encodes for a part of a protein, i.e. a peptide (see Herskowitz, 1187). This peptide can have a different function from the protein from whit it was derived. It can interact with the full protein and inhibit its activity or it can interact with other proteins and inhibit their activity in response to the full protein. Negative dominant means that the peptide is able to overcome the natural proteins and fully inhibit their activity to give the cell a different characteristic, like resistance or sensitization to killing. For therapeutic intervention either the peptide itself is delivered as the active ingredient of a pharmaceutical composition or the cDNA can be delivered to the cell utilizing the same methods as for antisense delivery.

The antagonist or regulating agent or active ingredient is dosed and delivered in a pharmaceutically acceptable carrier as described herein below. The term antagonist or antagonizing is used in its broadest sense. Antagonism can include any mechanism or treatment which results in inhibition, inactivation, blocking or reduction in gene activity or gene product and for example preventing progression from non-invasive to invasive. The antagonizing step can include blocking cellular receptors for the gene products and can include antisense treatment as discussed herein.

Many reviews have covered the main aspects of antisense (AS) technology and its enormous therapeutic potential (Wright and Anazodo, 1995). There are reviews on the chemical (Crooke, 1995; Uhlmann et al, 1990), cellular (Wagner, 1994) and therapeutic (Hanania, et al, 1995; Scanlon, et al, 1995; Gewirtz, 1993) aspects of this rapidly developing technology. Antisense intervention in the expression of specific genes can be achieved by the use of synthetic AS oligonucleotide sequences (for recent reports see Lefebvred-Hellencourt et al, 1995; Agrawal, 1996; Lev-Lehman et al, 1997). AS oligonucleotide sequences can be short sequences of DNA, typically 15–30 mer but can be as small as 7 mer (Wagner et al, 1996), designed to complement a target mRNA of interest and form an RNA:AS duplex. (See also Calabretta et al., 1996). Phosphorothioate antisense oligonucleotides do not normally show significant toxicity at concentrations that are effective, exhibit sufficient pharmacodynamic half-lives in animals (Agarwal et al., 1996) and are nuclease resistant. Instead of an antisense sequences as discussed herein above, ribozymes can be utilized. This is particularly necessary in cases where antisense-therapy is limited by stoichiometric considerations (Sarver et al., 1990, Gene Regulation and Aids, pp. 305–325). (See also Hampel and Tritz, 1989; Uhlenbeck, 1987).

Ribozymes catalyze the phosphodiester bond cleavage of RNA. Several ribozyme structural families have been identified including Group I introns, RNase P, the hepatitis delta virus ribozyme, hammerhead ribozymes and the hairpin ribozyme (Sullivan, 1994; U.S. Pat. No. 5,225,347, columns 4–5). Modifications or analogues of nucleotides can be introduced to improve the therapeutic properties of the nucleotides. Improved properties include increased nuclease resistance and/or increased ability to permeate cell membranes: Nuclease resistance, where needed, is provided by any method known in the art that does not interfere with biological activity of the antisense oligodeoxynucleotides, cDNA and/or ribozymes as needed for the method of use and delivery (Iyer et al., 1990; Eckstein, 1985; Spitzer and Eckstein, 1988; Woolf et al., 1990; Shaw et al., 1991). Modifications that can be made to oligonucleotides in order to enhance nuclease resistance include, but are not limited to, modifying the phophorous or oxygen heteroatom in the phosphate backbone. These modifications also include preparing methyl phosphonates, phosphorothioates, phosphorodithioates and morpholino oligomers.

The present invention also includes all analogues of, or modifications to, an oligonucleotide or polynucleotide of the invention that does not substantially affect the function of the oligonucleotide. The nucleotides can be selected from naturally occurring or synthetic modified bases. Naturally occurring bases include adenine, guanine, cytosine, thymine and uracil. Modified bases of the oligonucleotides include xanthine, hypoxanthine, 2-aminoadenine, 6-methyl, 2-propyl and other alkyl adenines, 5-halo uracil, 5-halo cytosine, 6-aza cytosine and 6-aza thymine, psuedo uracil, 4-thiuracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine.

In addition, analogues of nucleotides and/or polynucleotides can be prepared wherein the structure of the nucleotide and/or polynucleotide is fundamentally altered and that are better suited as therapeutic or experimental reagents. An example of a nucleotide analogue is a peptide nucleic acid (PNA) wherein the deoxyribose (or ribose) phosphate backbone in DNA (or RNA) is replaced with a polyamide backbone which is similar to that found in peptides. PNA analogues have been shown to be resistant to degradation by enzymes and to have extended lives in vivo and in vitro. Further, PNAs have been shown to bind stronger to a complementary DNA sequence than a DNA molecule. This observation is attributed to the lack of charge repulsion between the PNA strand and the DNA strand. Other modifications that can be made to oligonucleotides include polymer backbones, cyclic backbones, or acyclic backbones.

The active ingredients of pharmaceutical compositions can include oligonucleotides that are nuclease resistant as are needed for the practice of the, invention or a fragment thereof shown to have the same effect when targeted against the appropriate sequencers) and/or ribozymes. Combinations of active ingredients as disclosed in the present invention can be used, including combinations of antisense sequences.

The antisense oligonucleotides (and/or ribozymes) and cDNA of the present invention can be synthesized by any method known in the art for ribonucleic or deoxyribonucleic nucleotides. For example, an Applied Biosystems 380B DNA synthesizer can be used. When fragments are used, two or more such sequences can be synthesized and linked together for use in the present invention.

The nucleotide sequences of the present invention can be delivered either directly or with viral or non-viral vectors. When delivered directly the sequences are generally rendered nuclease resistant. Alternatively the sequences can be incorporated into expression cassettes or constructs such that the sequence is expressed in the cell as discussed herein below. Generally the construct contains the proper regulatory sequence or promotor to allow the sequence to be expressed in the targeted cell.

The proteins of the present invention can be produced recombinantly (see generally Marshak et al, 1996 "Strategies for Protein Purification and Characterization. A laboratory course manual.", CSHL Press) and analogues can be due to post-translational processing. More in particular, with respect to polynucleotides disclosed herein, and corresponding polypeptides expressed from them, the invention further comprehends isolated and/or purified polynucleotides (nucleic acid molecules) and isolated and/or purified polypeptides having at least about 70%, preferably at least about 75% homology, more preferably at least about 80%, even more preferably at least about 90%, most preferably at least about 95% homology to the polynucleotides and polypeptides disclosed herein.

Nucleotide sequence homology can be determined using the "Align" program of Myers and Miller, ((1988) *CABIAS* 4:11–17) and available at NCBI. Alternatively or additionally, the term "homology", "for instance, with respect to a nucleotide or amino acid sequence, can indicate a quantitative measure of homology between two sequences. The percent sequence homology can be calculated as (Nref−Ndif*100/Nref, wherein Ndif is the total number of non-identical residues in the two sequences when aligned and wherein Nref is the number of residues in one of the sequences Hence, the DNA sequence AGTCAGTC has a sequence similarity of 75% to AATCAATC (Nref=8; Ndif=2).

Alternatively or additionally, "homology" with respect to sequences can refer to the number of positions with identical nucleotides or amino acid residues divided by the number of nucleotides or amino acid residues in the shorter of the two sequences wherein alignment of the two sequences can be determined in accordance with the Wilbur and Lipman algorithm ((1983) Proc. Natl. Acad. Sci. USA 80:726), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc., CA). When RNA sequences are said to be similar, or to have a degree of sequence identity or homology with DNA sequences, thymidine M in the DNA sequence is considered equal to uracil (U) in the RNA sequence. RNA sequences within the scope of the invention can be derived from DNA sequences or their complements, by substituting thymidine (T) in the DNA sequence with uracil (U).

Additionally or alternatively, amino acid sequence similarity or identity or homology can be determined, for instance, using the BlastP program (Altschul et al. Nucl. Acids Res. 25:3389–3402) and available at NCBI. The following references provide algorithms for comparing the relative percentage homology of amino acid residues of two proteins, and additionally, or alternatively, with respect to the foregoing, the teachings in these references can be used for determining percent homology: Smith et al. (1981) Adv. Appl. Math. 2:482489; Smith et al. (1983) Nucl. Acids Res. 11:2205–2220; Devereux et al. (1984) Nucl. Acids Res. 12:387–395; Feng et al. (1987) J. Molec. Evol. 25:351–360; Higgins et al. (1989) *CABIOS* 5:151–153; and Thompson et al. (1994) Nucl. Acids Res. 22:4673–480.

Polynucleotide sequences that are complementary to any of the sequences or fragments encompassed by the present invention discussed above are also considered to be part of the present invention. Whenever any of the sequences discussed above are produced in a cell, the complementary sequence is concomitantly produced and, thus, the complementary sequence can also be used as a probe for the same diagnostic purposes. "Functionally relevant" refers to the biological property of the molecule and in this context means an in vivo effector or antigenic function or activity that is directly or indirectly performed by a naturally occurring protein or nucleic acid molecule. Effector functions include, but are not limited to include, receptor binding, any enzymatic activity or enzyme modulatory activity, any carrier binding activity, any hormonal activity, any activity in promoting or inhibiting adhesion of cells to extracellular matrix or cell surface molecules, or any structural role as well as having the nucleic acid sequence encode functional protein and can be expressible. The antigenic functions essentially mean the possession of an epitope or antigenic site that is capable of cross-reacting with antibodies raised against a naturally occurring protein. Biologically active analogues share an effector function of the native which can, but do not necessarily, additionally possess an antigenic function.

The above discussion provides a factual basis for the use of the sequences of the present invention to identify bladder cancer-associated genes and provide diagnostic probes and markers to identify bladder cancer, particularly in the early stages of TCC.

EXAMPLES

Example 1

Methods of the Invention

A detailed description of the methods employed in the present invention is set forth in co-assigned U.S. patent application U.S. Ser. No. 09/534,661 filed on Mar. 24, 2000 now U.S. Pat. No. 6,403,316, corresponding to PCT patent publication number WO 00/56935 and incorporated herein by reference in its entirety. The method includes preparing cell fractionations; extracting intact total RNA from membrane bound polysomes and free polysomes; preparing cDNA probes from template RNA derived from the extracted polysomes; performing microarray-based comparison of the relative abundance of the different RNA species; analyzing the results; thereby identifying genes or clones encoding specifically membranal or secreted proteins.

Identification of cDNAs and genes encoding secreted or membranal encoding mRNAs is of major importance in TCC. More specifically, novel genes which mark the early stages of TCC and code for secreted proteins are the ultimate markers for diagnosis and follow-up of TCC. By deriving probes from template RNA extracted from membrane-bound polysomes and free polysomes and performing microarray-based comparison of the relative abundance of different RNA species, such potentially secreted proteins can be identified. Analysis of the results of such comparison and identification of the clones encoding for membranal or secreted proteins provides a valuable tool which can be used together with other gene discovery tools, and which in itself enables identification of likely targets for drug development.

Since membranal and secreted proteins are both accessible and critical for transduction of numerous intra- and intercellular signals, they are generally viewed as preferred targets for pharmacological use and intervention. Therefore, the a priori classification of arrayed unknown gene sequences into those that potentially code for secreted and membranal proteins is of great value for the optimization of a high-throughput process of identifying potential drug targets. Furthermore, the identification of genes which express membranal or secreted proteins that are differentially expressed in different cellular situations is of the utmost importance in designing therapeutic or diagnostic tools for TCC. A method of identifying clones which encode membranal and secreted proteins was employed by preparing bladder cancer cell fractionations, preparing cDNA probes from template RNA derived from membrane-bound polysomes and free-polysomes, performing a microarray-based comparison of the relative abundance of different RNA species, analyzing the results and thereby identifying genes encoding for membranal and secreted proteins. Since membranal and secreted proteins are generally viewed as preferred targets for pharmacological intervention, the present invention thus provides a method of identifying likely targets for TCC diagnosis and therapy.

Hybridization and Probes:

TCC and Normal Bladder Hybridization:

The probes were prepared from normal healthy bladder samples and from TCC tumors. Only intact RNA with a proper histological report indicating the existence of TCC was used. All normal and tumor material was collected from two separate clinical centers. Such approach minimizes the influence of local specific surgical bias or subjectivity of the pathological report. Forty-one hybridizations were performed. In each hybridization, two probes were used simultaneously, each labeled with either Cy3 or Cy5.

These probes were as follows: Probe 1. Probe 1 was common to all hybridizations (common control probe). RNA from TCC samples was mixed with RNA from normal bladder samples. An equal amount of the RNA mixture was labeled with Cy3 and used in all hybridizations; and Probe 2. In each of the hybridizations, a different RNA sample from a single donor was used (test probe).

A common control for all the hybridizations enables comparison of the results between the different hybridizations. If the common control (probe 1) hybridization results are similar in pattern in different hybridizations, comparison can be made between the results of probe 2 hybridizations and all hybridizations. Seventeen hybridizations included 16 RNA samples extracted from different control healthy bladder mucosa labeled with Cy5. Twenty-three hybridizations were performed with RNA samples derived from tumor tissues, either from non-invasive Ta or from T1 stages of development. Two hybridizations were performed with RNA extracted from 2 invasive TCC samples.

The hybridizations were carried out in three separate sets, but the same common control was used in all sets. Set 1 includes hybridizations 2–11 (TC2–TC11), set 2 includes hybridizations 16–25 (TC16–TC25), and set 3 includes hybridizations 28–41 (TC28–TC41.). By using three different sets of hybridizations, the possibility of technical effects related to specific hybridizations is reduced. See Tables below and related description.

Probe from Annotation of Potentially Secreted Proteins:

TCC cell line—T24—(from ATCC) was used for cellular fractionation. Membrane-bound polysomes were separated from free polysomes using a sucrose step gradient. RNA coding for potentially secreted proteins was isolated from this microsomal-membranal fraction and separated from RNA coding for intracellular proteins. Hybridization was performed as described hereunder. The probes used were as follows: Probe 1. Free polysomal RNA fraction labeled with Cy3; and Probe 2. Membrane-bound RNA fraction with Cy5.

TCC Chip Preparation

All hybridizations were performed on TCC designated microarray. The microarray was made up of cDNA clones derived from 3 different libraries: SDGI library: (Described in co-assigned U.S. Patent Application U.S. Ser. No. 09/538, 709, filed 30 March, 2, 2000 now U.S. Pat. No. 6,468,749, corresponding to PCT application filed March, 2001 and incorporated herein by reference in its entirety): A pool of non-invasive TCC, invasive TCC and normal bladder was used for library preparation. 4550 clones from the SDGI library were included in the TCC chip. Antisense library: (Described in co-assigned U.S. Provisional Patent Application Ser. No. 60/157,843, filed 6 October, 1999, corresponding to PCT application PCT/US00/27557, filed 6 Oct., 2000, and incorporated herein by reference in its entirety): The same cDNA pool used for the SDGI library was used for the preparation of a library enriched for antisense sequences. 450 clones from this library were included in the TCC chip.

SSH library: (Diatchenko et al., 1996). A subtraction library was made as follows. A normal bladder RNA pool was used for subtraction from non-invasive TCC RNA pool. The subtracted cDNA was used for the microarray printing. 5000 clones from the SSH library were used for printing.

General Methods in Molecular Biology:

Standard molecular biology techniques known in the art and not specifically described were generally followed as in Sambrook et al., *Molecular Cloning: A Laboratory Manual*, Cold Spring Harbor Laboratory Press, New York (1989), and in Ausubel et al., *Current Protocols in Molecular Biology*, John Wiley and Sons, Baltimore, Md. (1989) and in Perbal, *A Practical Guide to Molecular Cloning*, John Wiley & Sons, New York (1988), and in Watson et al., *Recombinant DNA, Scientific American Books*, New York and in Birren et al (eds) *Genome Analysis: A Laboratory Manual Series*, Vols. 1–4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in *PCR Protocols: A Guide To Methods And Applications*, Academic Press, San Diego, Calif. (1990). In-situ (In-cell) PCR in combination with Flow Cytometry can be used for detection of cells containing specific DNA and mRNA sequences (Testoni et al, 1996, Blood 87:3822.) General methods in immunology: Standard methods in immunology known in the art and not specifically described are generally followed as in Stites et al.(eds), Basic and Clinical Immunology (8th Edition), Appleton & Lange, Norwalk, Conn. (1994) and Mishell and Shiigi (eds), Selected Methods in Cellular Immunology, W. H. Freeman and Co., New York (1980).

Immunoassays

In general, ELISAs where appropriate are one of the immunoassays employed to assess a specimen. ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, *Molecular Cloning: A Laboratory Manual*, Cold Springs Harbor, N.Y., 1989.

Antibody Production

Antibodies can be either monoclonal, polyclonal or recombinant. Conveniently, the antibodies can be prepared against the immunogen or portion thereof for example a synthetic peptide based on the sequence, or prepared recombinantly by cloning techniques or the natural gene product and/or portions thereof can be isolated and used as the immunogen. Immunogens can be used to produce antibodies by standard antibody production technology well known to those skilled in the art as described generally in Harlow and Lane, *Antibodies: A Laboratory Manual*, Cold Spring Harbor Laboratory, Cold Spring Harbor, N.Y., 1988 and Borrebaeck, *Antibody Engineering-A Practical Guide*, W. H. Freeman and Co., 1992. Antibody fragments can also be prepared from the antibodies and include Fab, F(ab')$_2$, and Fv by methods known to those skilled in the art. For producing polyclonal antibodies a host, such as a rabbit or goat, is immunized with the immunogen or immunogen fragment, generally with an adjuvant and, if necessary, coupled to a carrier; antibodies to the immunogen are collected from the sera. Further, the polyclonal antibody can be absorbed such that it is monospecific. That is, the sera can be absorbed against related immunogens so that no cross-reactive antibodies remain in the sera rendering it monospecific.

For producing monoclonal antibodies the technique involves hyperimmunization of an appropriate donor with the immunogen, generally a mouse, and isolation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

For producing recombinant antibody (see generally Huston et al, 1991; Johnson and Bird, 1991; Mernaugh and Mernaugh, 1995), messenger RNAs from antibody producing B-lymphocytes of animals, or hybridoma are reverse-transcribed to obtain complementary DNAs (cDNAs). Antibody cDNA, which can be full or partial length, is amplified and cloned into a phage or a plasmid. The cDNA can be a partial length of heavy and light chain cDNA, separated or connected by a linker, e.g., encoding a single chain antibody. The antibody, or antibody fragment, is expressed using a suitable expression system to obtain recombinant antibody. Antibody cDNA can also be obtained by screening pertinent expression libraries.

The antibody can be bound to a solid support substrate or conjugated with a detectable moiety or be both bound and conjugated as is well known in the art. (For a general discussion of conjugation of fluorescent or enzymatic moieties see Johnstone & Thorpe, *Immunochemistry in Practice*, Blackwell Scientific Publications, Oxford, 1982.) The binding of antibodies to a solid support substrate is also well known in the art. (see for a general discussion Harlow & Lane *Antibodies: A Laboratory Manual*, Cold Spring Harbor Laboratory Publications, New York, 1988 and Borrebaeck, *Antibody Engineering-A Practical Guide*, W. H. Freeman and Co., 1992) The detectable moieties contemplated with the present invention can include, but are not limited to, fluorescent, metallic, enzymatic and radioactive markers such as biotin, gold, ferritin, alkaline phosphatase, β-galactosidase, peroxidase, urease, fluorescein, rhodamine, tritium, $^{14}$C and iodination.

Recombinant Protein Purification

Marshak et al, "Strategies for Protein Purification and Characterization. A laboratory course manual." CSHL Press, 1996.

Gene Therapy:

The genes described in this patent can also be used as targets for gene therapy, since these genes can be of importance for the development of TCC. Therefore, targeted gene therapy against one or more of these genes, or against one or more of the corresponding polypeptides encoded by these genes, is applied to cure TCC and/or to retard the spread of TCC. BGene therapy as used herein refers to the transfer of genetic material (e.g. DNA or RNA) of interest into a host to treat or prevent a genetic or acquired disease or condition phenotype. The genetic material of interest encodes a product (e.g. a protein, polypeptide, peptide, functional RNA, antisense) whose production in vivo is desired. For example, the genetic material of interest can encode a hormone, receptor, enzyme, polypeptide or peptide of therapeutic value. Alternatively, the genetic material of interest encodes a suicide gene. For a review see, in general, the text "Gene Therapy" (Advances in Pharmacology 40, Academic Press, 1997).

Vectors can be introduced into cells or tissues by any one of a variety of known methods within the art. Such methods can be found generally described in Sambrook et al., *Molecular Cloning: A Laboratory Manual*, Cold Springs Harbor Laboratory, New York (1989, 1992), in Ausubel et al., *Current Protocols in Molecular Biology*, John Wiley and Sons, Baltimore, Md. (1989), Chang et al., *Somatic Gene Therapy*, CRC Press, Ann Arbor, Mich. (1995), Vega et al., Gene Targeting, CRC Press, Ann Arbor, Mich. (1995), *Vectors: A Survey of Molecular Cloning Vectors and Their Uses*, Butterworths, Boston Mass. (1988) and Gilboa et al (1986) and include, for example, stable or transient transfection, lipofection, electroporation and infection with recombinant viral vectors. In addition, see U.S. Pat. No. 4,866,042 for vectors involving the central nervous system and also U.S. Pat. Nos. 5,464,764 and 5,487,992 for positive-negative selection methods.

Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

A specific example of DNA viral vector for introducing and expressing recombinant sequences is the adenovirus derived vector Adenop53TK. This vector expresses a herpes virus thymidine kinase (TK) gene for either positive or negative selection and an expression cassette for desired recombinant sequences. This vector can be used to infect cells that have an adenovirus receptor which includes most cancers of epithelial origin as well as others. This vector as well as others that exhibit similar desired functions can be used to treat a mixed population of cells and can include, for example, an in vitro or ex vivo culture of cells, a tissue or a human subject.

Additional features can be added to the vector to ensure its safety and/or enhance its therapeutic efficacy. Such features include for example, markers that can be used to negatively select against cells infected with the recombinant virus. An example of such a negative selection marker is the TK gene described above that confers sensitivity to the antibiotic gancyclovir. Negative selection is therefore a means by which infection can be controlled because it provides inducible suicide through the addition of antibiotic. Such protection ensures that if, for example, mutations arise that produce altered forms of the viral vector or recombinant sequence, cellular transformation can not occur.

Features that limit expression to particular cell types can also be included. Such features include, for example, promoter and regulatory elements that are specific for the desired cell type.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods of the invention depends on desired cell type to be targeted and is known to those skilled in the art. Thus, if bladder cancer is to be treated then a vector specific for such epithelial cells are used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed do not contain a genome and therefore cannot proceed through subsequent rounds of infection. The specific type of vector depends upon the intended application. The actual vectors are also known and readily available within the art or can be constructed by one skilled in the art using well-known methodology.

The recombinant vector can be administered in several ways. If viral vectors are used, for example, the procedure can take advantage of their target specificity and consequently, do not have to be administered locally at the diseased site. However, local administration can provide a quicker and more effective treatment, administration can also be performed by, for example, intravenous or subcutaneous injection into the subject. Following injection, the viral vectors circulate until they recognize host cells with the appropriate target specificity for infection.

An alternate mode of administration can be by direct inoculation into the bladder i.e., locally to the site of the disease or pathological condition or by inoculation into the vascular system supplying the site with nutrients. Local administration is advantageous because there is no dilution effect and, therefore, a smaller dose is required to achieve expression in a majority of the targeted cells. Additionally, local inoculation can alleviate the targeting requirement required with other forms of administration since a vector can be used that infects all cells in the inoculated area. If expression is desired in only a specific subset of cells within the inoculated area, then promoter and regulatory elements that are specific for the desired subset can be used to accomplish this goal. Such non-targeting vectors can be, for example, viral vectors, viral genome, plasmids, phagemids and the like. Transfection vehicles such as liposomes can also be used to introduce the non-viral vectors described above into recipient cells within the inoculated area. Such transfection vehicles are known by one skilled within the art.

Chemical Compounds

The chemical compounds to be administered comprise inter alia small chemical molecules; antibodies of all types or fragments thereof including single chain antibodies; antisense oligonucleotides, antisense oligonucleotides, polynucleotides., DNA or RNA molecules; proteins, polypeptides and peptides including peptido-mimetics and dominant negative peptides; ribozymes; and expression vectors Delivery of Chemical Compound The compound of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound or as pharmaceutically acceptable salt and can be administered alone or as an active ingredient in combination with pharmaceutically acceptable carriers, diluents, adjuvants and vehicles. The compounds can be administered intravesically (directly into the bladder),orally, subcutaneously or parenterally including intravenous, intraarterial, intramuscular, intraperitoneally, and intranasal administration as well as intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, nontoxic solid or liquid fillers, diluents or encapsulating material not reacting with the active ingredients of the invention.

It is noted that humans are treated generally longer than the mice or other experimental animals exemplified herein which treatment has a length proportional to the length of the disease process and drug effectiveness. The doses can be single doses or multiple doses over a period of several days, but single doses are preferred.

The doses can be single doses or multiple doses over a period of several days. The treatment generally has a length proportional to the length of the disease process and drug effectiveness and the patient species being treated.

When administering the compound of the present invention parenterally, it is generally formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, can also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it is desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used have to be compatible with the compounds.

Sterile injectable solutions can be prepared by incorporating the compounds utilized in practicing the present invention in the required amount of the appropriate solvent with various of the other ingredients, as desired. A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,1.94; 4,447,233; 4,447,224; 4,439,196; and 4,475,196. Many other such implants, delivery systems, and modules are well known to those skilled in the art.

A pharmacological formulation of the compound utilized in the present invention can be administered orally to the patient. Conventional methods such as administering the compounds in tablets, suspensions, solutions, emulsions, capsules, powders, syrups and the like are usable. Known techniques which deliver it orally or intravenously or directly to the bladder (intravesically) and retain the biological activity are preferred. In one embodiment, the compound of the present invention can be administered initially by intravenous injection to bring blood levels to a suitable level. The patient's levels are then maintained by an oral dosage form, although other forms of administration, dependent upon the patient's condition and as indicated above, can be used. The quantity to be administered vary for the patient being treated and vary from about 100 ng/kg of body weight to 100 mg/kg of body weight per day and preferably are from 10 μg/kg to 10 μg/kg per day.

Example 2

Polynucleotides and Diagnostic Applications

Utilizing the methods set forth above, the polynucleotides set forth in Tables 1 and 2 were identified and cloned as being differentially expressed in bladder cancer 41 hybridizations were compared.

The polynucleotides described in Table 1 are identified by clone number and accession number. This list includes sequences of known genes whose function in bladder cancer was heretofore unknown and which were now found to upregulated in bladder cancer. Corresponding nucleic acid sequences are provided in Table 3.

The polynucleotides described in Table 2 are identified by clone number. This list includes sequences of novel genes which have no identity to known proteins or genes in the gene databases. Corresponding nucleic acid sequences are provided in Table 4.

In both Tables 1 and 2, the differential expression pattern of the different hybridization probes is provided. In both Table 1 and 2, the genes listed were found to be upregulated in at least 60% of TCC samples and unchanged in at least 75% of the normal samples.

Tables 1 and 2 show the genes as described in biological NCBI databases, with the Genebank number of each gene (where applicable) as presented in the NCBI database. The location of the clone in the TCC microarray of the present invention is set forth in the tables, with their clone ID in the TCC chip.

The expression differentials described in Tables 1 and 2 were calculated as follows: Since a common control probe was used for all hybridizations and the hybridizations were carried out in three separate sets, the expression differentials in each respective set were calculated as compared to one of the normal bladder samples, as a reference probe.

Thus, hybridization set 1 which includes hybridizations TC2–TC11, all the results are shown as compared to the TC7 (normal) hybridization result. In hybridization set 2 which includes hybridizations TC16TC25, all the results were calculated in comparison to the TC22 (normal) hybridization result. In set 3, which includes hybridizations TC28–TC41, all the results were calculated compared to the reference normal probe from TC47.

Example 3

Key Genes

In the present invention, the results of the 41 hybridizations were analyzed on the TCC microarray, in order to provide a statistically meaningful set of genes (which each include one of the polynucleotides identified) that can identify TCC samples and be used as a TCC marker set. As a result, a sub-set of twenty-two (22) potential molecular markers for non-invasive TCC was identified and validated using supervised statistical analysis methods. The 22 genes identified as potential markers (listed in Table 5) code for secreted factors, cytoskeletal and membranal proteins, all potentially suitable for the development of non-invasive diagnostic tests. This marker set of genes is described below, in Example 4, Section 5, entitled "Expression patterns, scores and significance values for 22 short-listed genes", and related Tables C1 and C2. Thirteen (13) of these 22 polynucleotides are described in Example 2 (see Tables 1–4), and nine (9) are newly described in this Example (see Tables 5–6). In Table 5, the polynucleotides already described in Tables 1 and 2 are designated with an "x".

The 22 gene marker set was identified following reanalysis of the 41 hybridizations. All the experiments were constructed so that such an analysis can be performed. The hybridization scheme (described in Section 1 hereunder) was based on both individual sample hybridizations and a common control approach. All the hybridizations passed quality control examination and pre-processing steps (described in Sections 2 and 3 hereunder) which are critical to establish input material suitable for any statistical analysis. Following these pre-processing steps, the hybridization data was scored according to its "similarity" to the desired discrimination—non-invasive TCC versus normal urothelium (see Example 5).

Two independent (though related) standard scoring methods were used and individual genes were selected that discriminate between non-invasive TCC and normal urothelium (see Example 5, Section 4).

Full bioinformatic annotation analysis of the 22 listed genes (see Example 5, Section 6) and detailed description of their potential biological relevance to cancer in general and to TCC in particular is presented herein (see Example 5, Sections 6 and 7).

Based on the sequence annotation, 17 of the selected 22 markers were found to be known, characterized genes and 5 code for genes with an unknown protein product. At least four of the known genes and 1 of the genes with yet unknown protein products code for membranal or secreted proteins, based on the Applicants' proprietary "secreted" probe (described in co-assigned U.S. Ser. No. 09/534,661, now U.S. Pat. No. 6,438,749, corresponding to PCT patent publication number WO 00/56935 which is incorporated herein by reference in its entirety) and on domain analysis. (See Example 5, Sections 4 and 6). Being secreted, some of these proteins can be identified in body fluids (in particular urine), thus alleviating the need for invasive tests. All other non-secreted proteins can also be detected in urine, which always contains shedded urothelial cells.

For a diagnostic assay, urine samples of TCC patients and of non-TCC patients should be analyzed. Urine can be collected, preserved in −70° C. and used either for protein assays (Western analysis) with the relevant antibody and/or for ELISA tests with the same relevant antibody. Similarly, blood samples from the same donors can be collected, and the separated serum samples can be used for detection of the candidate proteins in the serum using similar protein analysis approach. After establishing the particular assay for a single protein, assays for a combination of 2 or more different proteins can be set to increase the validity of the obtained results for each sample and to obtain robustness.

According to biomedical literature, the 17 known genes were classified into three functional groups: tumorigenesis, keratinocyte differentiation, and cell motility and proliferation. Thus, these markers can also fulfill a functional role in TCC. Being functionally relevant these genes can be used as possible targets for genes therapy for TCC. This can be achieved by antagonizing their affects in the tumor using antisense delivery approach (for all such proteins), blocking their enzymatic activity (for enzymes), or specific drug delivery, as relevant. Since different keratins were detected as being differentially expressed in TCC, specific typing of the different keratins in urine of TCC patients, using a single multi-gene assay, can facilitate and improve robust TCC diagnostics.

The specificity of markers for TCC over other cancers is an important consideration. In particular, the expression level of the selected gene set is analyzed in other urogenital cancers, such as renal carcinoma and prostate cancer. Importantly, samples obtained from clinically relevant controls, such as inflammation or benign prostate hyperplasia (BPH) must be included. Retrospective studies of patients is also be carried out, as well as comparison of samples obtained during follow-up procedures (to monitor tumor progression in TCC patients).

All the genes described in the present invention are tested for their level of expression of exfoliated cells in urine, according to the following protocol. Urine samples (e.g. 100 ml of urine) are collected from 3 different populations: healthy donors, TCC patients and a relevant control group (e.g., prostate cancer, bladder inflammation). The exfoliated cells are separated from urine (it is possible to keep the separated cells in −70° C. pending further work) and used for preparation of RNA. Such an approach enables tracking cancer-related changes at the level of gene expression. Following RNA extraction, RT-PCR is performed for selected genes. Primers specific for each of these genes are constructed and used for the amplification of the cDNA products, being constructed so that each of the tested genes are be amplified to a fragment of a different size. RT-PCR reaction is carried out in semi-quantitative approach. Fractionation for the resultant products on gels indicates the relative abundance of each of the tested genes in the tested RNA sample. Alternatively, TAQMAN ® (Applied Biosystems) enables a fully quantitative time-course demonstration of the level of expression of these genes. Results for each of the tested genes are defined and documented and used for statistical analysis. Finally, a value is calculated for the expression of the predictor gene set in TCC and in non-TCC samples. Comparison of the expression level results for a given unknown sample to this known calculated value predicts if the tested sample contains TCC (under certain confidence level, p value). All information from the tested samples is gathered during the establishment of the described diagnostic protocol and the statistical analysis is expanded so that all samples participating in the study are included.

According to the present invention, gene sequences are included which are uniformly expressed in normal and TCC tissues (see Example 5, Section 8). These genes can be used as an internal control in each multiplex RT-PCR. To this end primers for amplification of such genes are constructed and applied within the RT-PCR reaction of the marker gene set.

In further analysis, the results obtained from a single donor are compared between different tissues obtained from the same donor, e.g., matched urine exfoliated cells and tumor tissue (for RT-PCR approach) or urine and blood for the protein analysis approach. This enables a deeper understanding of the molecular changes associated with TCC and their general presentation in different organs.

The genes provided in the present patent application can also be used for printing a small diagnostic TCC mini-microarray. This chip includes also clones with a uniform high expression in both normal urothelium and TCC (see Example 5, Section 8). Such TCC mini-microarray can be used for both disease detection and validation and for molecular staging and grading of the TCC tumors. Samples for hybridization on such chip include material derived from TCC tumors and from normal urothelium from different donors.

In addition, urine exfoliated cells from the same donors can be used for RNA extraction and RNA amplification. The RNA can be used for generating cDNA probes for the TCC mini cDNA microarray. This enables characterization of gene expression patterns of all the printed genes and comparison between the expression pattern obtained using tissue-type material to that obtained by cells shedded in urine. Since shedded cells are also collected from non-TCC donors such as patients with BPH and inflammation, these also comprise part of the hybridization probes.

The present invention further presents the use of a small subset of genes (2 or more genes) together for providing an accurate diagnostic test for TCC. With one exception (the cytokeratin 8 and 18 assay), all commercially existing molecular diagnostics for TCC are based on tests for single proteins. These can be insufficient to account for the inherent complexity of cancer, as well as for the variability of both healthy and affected populations. To this end, the present invention describes the use of a combination of several genes and/or proteins either as a marker set for detection of these proteins in urine or in other body fluids, and/or by using the cells or cell debris present in the urine of TCC patients for multiple-gene RT-PCR diagnostic testing.

In-situ hybridization analysis using the same gene set can be performed as an auxiliary qualitative validation step, using paraffin blocks from normal urothelium and TCC tumors.

The genes of the present invention also characterize different stages of TCC. Correct "staging" of TCC is fundamental for the management of this disease. Upon detection of a new TCC patient, the developmental stage of the tumors determines relevant treatment. For example, if a non-invasive tumor is identified, "TURT" is the surgical approach recommended. If, however, the tumor is-defined as invasive TCC, cystectomy is usually the treatment of choice. Identification of those non-invasive TCC patients that might progress is of great clinical value.

Keratin 13 is identified herein as a marker that can differentiate Ta from T1 and invasive tumors (see Section 10). The analysis described in the present invention indicates a clear discrimination between Ta and T1 tumors, where this gene is upregulated in Ta tumors and downregulated in T1 tumors when compared to normal urothelium. This gene in include part of the diagnostic tests described.

According to the present invention, 22 polynucleotides included in 22 genes were identified; these genes serve as potential markers for TCC, especially for non-invasive TCC. These genes, and all the genes included in Tables 1–6, can be used for diagnosis of TCC.

Full-length genes or gene fragments are suggested as markers for non-invasive assays. PCR products, antisense products, protein products and antibodies raised against these genes can be applied both for diagnostics for TCC and for targeted gene therapy. The tests for the levels of these genes and/or proteins can be performed in body fluids, in the original tumor or in other relevant body organs, and in cells found in the urine of patients.

Example 4

Hybridizations and Statistical Analysis

Section 1. Hybridization Scheme

The hybridization scheme according to the present invention is based on three principles 1. Individual hybridization of each sample (normal or TCC) whenever possible: This provides a comprehensive overview of the entire sample set, with minimal a-priori assumptions, and with maximal measurement of the variability between the samples. Such individual hybridization procedure is crucial for successful analysis of the results. In a small number of cases, due to insufficient amounts of normal urothelium material, pools of several normal samples were used as a single probe (See Table A, $3^{rd}$ set).

2. Utilization of an identical common normalizing probe ("Common Control" or "CC") in each set of hybridizations: By maintaining one of the probes as a constant, common probe, hybridization results can be compared across experiments. The common normalizing probe used in the present invention was prepared from a pool of RNA from different TCC and normal samples. This material should be similar in composition to the one used for construction of the TCC microarray. Thus, it has a high probability to hybridize and detect a maximal number of elements on the TCC array, and to provide an appropriate normalization of signals between hybridizations.

3. Secreted and membranal proteins have an obvious advantage as molecular markers. The "secreted" probe allows sequence-independent identification of genes potentially coding for secreted and membranal proteins. If such genes are highly expressed in tumors it is plausible to try to find their protein products highly expressed in urine, too.

Hybridizations of TCC and of normal urothelium samples were performed in 3 sets which were separated in time as well as in the methods of RNA preparation (polyA and total), as shown in Table A. Although these differences increase the variability of the results, they also suggest that the identified phenomena are robust to experimental intricacies. Comparison of gene expression results between the sets increases the validity of the results obtained. Differences in RNA preparation can also affect the common normalizing probe. For example, in the first two sets an identical total RNA pool was used (Table A common normalizing probe1), while in the $3^{rd}$ set polyA RNA was extracted from the same pool of total RNA and used as a common control (Table A, common normalizing probe2).

TABLE A

Detailed hybridization scheme

| Set number | Probe type | Probe 1 (Cy3) | Probe 2(Cy5): "Experiment" probe | | | |
|---|---|---|---|---|---|---|
| | | | Type (# samples) | Code | Stage | Grade |
| 1 | Total RNA | Common normalising probe1 (total RNA) | TCC (5) | TC2 | Ti | |
| | | | | TC3 | Tl | G2/G3 |
| | | | | TC4 | Tl | G2/G3 |
| | | | | TC5 | Tl | |
| | | | | TC6 | Tl | |
| | | | Normal (5) | TC7 | normal | |
| | | | | TC8 | normal | |
| | | | | TC9 | normal | |
| | | | | TC10 | normal | |
| | | | | TC11 | normal | |
| 2 | Total RNA | Common normalising probe1 (total RNA) | TCC (6) | TC16 | Ta | G2 |
| | | | | TC17 | Ta | G2 |
| | | | | TC18 | Ta | High |
| | | | | TC19 | Tl | Low |
| | | | | TC20 | Tl | G3 |
| | | | | TC25 | Tl | G1 |
| | | | Normal (4) | TC22 | normal | |
| | | | | TC22 | Normal | |
| | | | | TC23 | Normal | |
| | | | | TC24 | Normal | |
| 3 | Poly A RNA | Common normalising probe2 (poly A) | TCC (14) | TC28 | Tl + TIS | G3 |
| | | | | TC29 | Tl | High |
| | | | | TC30 | Tl | G3 |
| | | | | TC31 | Ta | G1/2 |
| | | | | TC32 | Ta/Tl | G2 |
| | | | | TC33 | Ta | G2 |
| | | | | TC34 | invasive | G3 |
| | | | | TC39 | Ta | low |
| | | | | TC40 | Tl | G1/2 |
| | | | | TC41 | Ta | G2 |
| | | | | TC42 | Ta | G2 |
| | | | | TC43 | Tl | G2 |
| | | | | TC44 | Ta | G2 |
| | | | | TC45 | invasive | G3 |
| | | | Normal (19) | TC35 | Normal | |
| | | | | TC36 | Normal | |
| | | | | TC37 | Normal pool | |
| | | | | TC38 | Normal pool | |
| | | | | TC46 | Normal | |
| | | | | TC47 | normal pool | |
| | | | | TC48 | normal pool | |

| Set number | Probe type | TCC invasive cell line | Code | Probe 1(Cy3) | Probe 2(Cy5) |
|---|---|---|---|---|---|
| 4 | Secreted | SW780 | TC49 | Free polysomal RNA | Membrane bound polysomal RNA |
| | | T24 | TC50 | | |

In order to identify secreted and membranal proteins, two "secreted" probes were prepared from human invasive TCC cell lines, T24 and SW780. Briefly, membrane-bound polysomes were separated from free polysomes using sucrose step gradient. RNA coding for potentially secreted proteins was isolated from the microsomal-membranal fraction and RNA coding for intracellular proteins from the free polysomal pellet. Each RNA ("Secreted" and "Intracellular") was labelled with a different dye and hybridized to the TCC array (Table A, set 4). Significant differential expression in one of the probes is an indication of potential cellular compartments (intracellular or secreted/membranal). As a convention, a negative differential represents secreted proteins.

Section 2. Quality Control (QC)$_1$ Preliminary Evaluation

In order to ensure the quality of the results shows in the present invention and to minimize experimental artefacts, all hybridization results underwent several standard QC steps. Since the hybridizations were performed in three separate sets, QC procedures were done within sets, consistent with inventors' past experience.

1. Reproducibility of the common control probe. Relative expression levels are compared across hybridizations due to the use of a common normalizing probe. However, this can be faithfully performed only if the common control probe behaves consistently across each set of hybridization. This consistency is first measured by the pair-wise correlations between the common control signal vectors. The pair-wise correlation coefficient between common control probes in each set are almost invariably very high (>0.97, Table B1). These results indicate the suitability of common control-based normalization for this data set

TABLE B1

Common control correlations (by hybridization set) for 41 TCC hybridizations

Set #1

| | TC10 | TC11 | TC2 | TC3 | TC4 | TC5 | TC6 | TC7 | TC8 | TC9 |
|---|---|---|---|---|---|---|---|---|---|---|
| TC10 | 1.00 | .96 | .97 | .97 | .97 | .98 | .98 | .97 | .87 | .98 |
| TC11 | .96 | 1.00 | .97 | .98 | .97 | .97 | .97 | .97 | .88 | .98 |
| TC2 | .97 | .97 | 1.00 | .98 | .98 | .98 | .98 | .98 | .88 | .98 |
| TC3 | .97 | .98 | .98 | 1.00 | .99 | .98 | .99 | .98 | .89 | .98 |
| TC4 | .97 | .97 | .98 | .99 | 1.00 | .99 | .98 | .97 | .88 | .98 |
| TC5 | .98 | .97 | .98 | .98 | .99 | 1.00 | .98 | .97 | .88 | .98 |
| TC6 | .98 | .97 | .98 | .99 | .98 | .98 | 1.00 | .98 | .89 | .99 |
| TC7 | .97 | .97 | .98 | .98 | .97 | .97 | .98 | 1.00 | .89 | .98 |

TABLE B1-continued

Common control correlations (by hybridization set)
for 41 TCC hybridizations

| | | | | | | | | | | |
|---|---|---|---|---|---|---|---|---|---|---|
| TC8 | .87 | .88 | .88 | .89 | .88 | .88 | .89 | .89 | 1.00 | .89 |
| TC9 | .98 | .98 | .98 | .98 | .98 | .98 | .99 | .98 | .89 | 1.00 |

Set #2

| | TC16 | TC17 | TC18 | TC19 | TC20 | TC21 | TC22 | TC23 | TC24 | TC25 |
|---|---|---|---|---|---|---|---|---|---|---|
| TC16 | 1.00 | .98 | .97 | .98 | .98 | .97 | .98 | .97 | .97 | .97 |
| TC17 | .98 | 1.00 | .98 | .99 | .98 | .98 | .98 | .98 | .97 | .98 |
| TC18 | .97 | .98 | 1.00 | .98 | .97 | .97 | .97 | .97 | .96 | .97 |
| TC19 | .98 | .99 | .98 | 1.00 | .98 | .98 | .98 | .97 | .97 | .97 |
| TC20 | .98 | .98 | .97 | .98 | 1.00 | .98 | .98 | .97 | .97 | .97 |
| TC21 | .97 | .98 | .97 | .98 | .98 | 1.00 | .98 | .97 | .97 | .97 |
| TC22 | .98 | .98 | .97 | .98 | .98 | .98 | 1.00 | .98 | .97 | .98 |
| TC23 | .97 | .98 | .97 | .97 | .97 | .97 | .98 | 1.00 | .97 | .97 |
| TC24 | .97 | .97 | .96 | .97 | .97 | .97 | .97 | .97 | 1.00 | .96 |
| TC25 | .97 | .98 | .97 | .97 | .97 | .97 | .98 | .97 | .96 | 1.00 |

Set #3

| | TC28 | TC29 | TC30 | TC31 | TC32 | TC33 | TC34 | TC35 | TC36 | TC37 | TC38 |
|---|---|---|---|---|---|---|---|---|---|---|---|
| TC28 | 1.00 | .99 | .97 | .98 | .98 | .98 | .98 | .98 | .99 | .99 | .99 |
| TC29 | .99 | 1.00 | .97 | .97 | .98 | .98 | .98 | .97 | .98 | .98 | .98 |
| TC30 | .97 | .97 | 1.00 | .98 | .98 | .98 | .98 | .98 | .99 | .98 | .98 |
| TC31 | .98 | .97 | .98 | 1.00 | .99 | .98 | .98 | .98 | .99 | .99 | .99 |
| TC32 | .98 | .98 | .98 | .99 | 1.00 | .99 | .99 | .98 | .99 | .99 | .99 |
| TC33 | .98 | .98 | .98 | .98 | .99 | 1.00 | .99 | .98 | .99 | .99 | .99 |
| TC34 | .98 | .98 | .98 | .98 | .99 | .99 | 1.00 | .98 | .99 | .99 | .99 |
| TC35 | .98 | .97 | .98 | .98 | .98 | .98 | .98 | 1.00 | .98 | .98 | .98 |
| TC36 | .99 | .98 | .99 | .99 | .99 | .99 | .99 | .98 | 1.00 | .99 | .98 |
| TC37 | .99 | .98 | .98 | .99 | .99 | .99 | .99 | .98 | .99 | 1.00 | .99 |
| TC38 | .99 | .98 | .98 | .99 | .99 | .99 | .99 | .98 | .99 | .99 | 1.00 |
| TC39 | .98 | .97 | .98 | .98 | .98 | .98 | .98 | .97 | .98 | .99 | .98 |
| TC40 | .98 | .98 | .98 | .98 | .99 | .98 | .98 | .97 | .99 | .99 | .99 |
| TC41 | .97 | .97 | .97 | .98 | .98 | .98 | .97 | .97 | .98 | .98 | .98 |
| TC42 | .97 | .97 | .97 | .98 | .97 | .97 | .97 | .96 | .97 | .98 | .98 |
| TC43 | .98 | .98 | .98 | .98 | .99 | .98 | .98 | .98 | .99 | .99 | .99 |
| TC44 | .97 | .97 | .97 | .97 | .98 | .97 | .97 | .96 | .97 | .97 | .97 |
| TC45 | .97 | .96 | .97 | .97 | .97 | .96 | .98 | .96 | .97 | .97 | .97 |
| TC46 | .97 | .97 | .96 | .97 | .97 | .96 | .96 | .95 | .96 | .97 | .97 |
| TC47 | .98 | .97 | .97 | .97 | .98 | .97 | .97 | .96 | .96 | .98 | .98 |
| TC48 | .96 | .96 | .96 | .97 | .97 | .95 | .95 | .95 | .96 | .97 | .97 |

Set #3

| | TC39 | TC40 | TC41 | TC42 | TC43 | TC44 | TC45 | TC46 | TC47 | TC48 |
|---|---|---|---|---|---|---|---|---|---|---|
| TC28 | .98 | .98 | .97 | .97 | .98 | .97 | .97 | .97 | .98 | .96 |
| TC29 | .97 | .98 | .97 | .97 | .98 | .97 | .96 | .97 | .97 | .96 |
| TC30 | .98 | .98 | .97 | .97 | .98 | .97 | .97 | .96 | .97 | .96 |
| TC31 | .98 | .98 | .98 | .98 | .98 | .97 | .97 | .97 | .97 | .97 |
| TC32 | .98 | .99 | .98 | .97 | .99 | .98 | .97 | .97 | .98 | .97 |
| TC33 | .98 | .98 | .98 | .97 | .98 | .97 | .96 | .96 | .97 | .95 |
| TC34 | .98 | .98 | .97 | .97 | .98 | .97 | .96 | .96 | .97 | .95 |
| TC35 | .97 | .97 | .97 | .96 | .98 | .96 | .96 | .95 | .96 | .95 |
| TC36 | .98 | .99 | .98 | .97 | .99 | .97 | .97 | .96 | .98 | .96 |
| TC37 | .99 | .99 | .98 | .98 | .99 | .97 | .97 | .97 | .98 | .97 |
| TC38 | .98 | .99 | .98 | .98 | .99 | .97 | .97 | .97 | .98 | .97 |
| TC39 | 1.00 | .99 | .98 | .98 | .98 | .98 | .98 | .97 | .96 | .97 |
| TC40 | .99 | 1.00 | .98 | .98 | .99 | .98 | .98 | .97 | .98 | .97 |
| TC41 | .98 | .98 | 1.00 | .98 | .98 | .97 | .97 | .97 | .97 | .97 |
| TC42 | .98 | .98 | .98 | 1.00 | .98 | .97 | .98 | .97 | .97 | .97 |
| TC43 | .98 | .99 | .98 | .98 | 1.00 | .97 | .97 | .97 | .97 | .97 |
| TC44 | .98 | .98 | .97 | .97 | .97 | 1.00 | .98 | .97 | .98 | .98 |
| TC45 | .98 | .98 | .97 | .98 | .97 | .98 | 1.00 | .98 | .98 | .99 |
| TC46 | .97 | .97 | .97 | .97 | .97 | .97 | .98 | 1.00 | .99 | .99 |
| TC47 | .98 | .98 | .97 | .97 | .97 | .98 | .98 | .99 | 1.00 | .99 |
| TC48 | .97 | .97 | .97 | .97 | .97 | .98 | .99 | .99 | .99 | 1.00 |

2. Signal quality. A second measure of hybridization quality is the number of elements which yielded a significant signal and a reliable signal to background (S2B) ratio with each probe. Since a custom cDNA array was used, both experiment and control probes are expected to yield a similar number of significant signals (A set of n hybridizations of an m-gene array is typically treated as a matrix A of size m×n. Thus the expression level of each gene in all n hybridizations is a vector of size m ("gene vector"). A single hybridization experiment is represented by a vector of m expression measurements ("hybridization vector"). In differential profiling the vector can represent a single probe (in which case it is a vector of signals) or both (a vector of differentials)). Thus, when comparing the hybridization quality of the common control probes, pair-wise correlation was calculated between the common control signal vector in one hybridization to that of another. Missing values were deleted on a case-wise basis. Traditional threshold (200 units) for signals, for both common control and tested sample probes, and. S2B (value of 2.5 for at least 40% coverage of element) were used (Table B2).

The first and third sets of hybridizations yielded signals of high quality in both common control and experiment probes. The quality of the second set was significantly lower (Table B2).

TABLE B2

Signal qua

| Code | Significant P1 | Significant P2 |
|---|---|---|
| Set #1 | | |
| TC10A | 6679 | 6450 |
| TC11A | 5280 | 4546 |
| TC2A | 5834 | 5097 |
| TC3A | 6603 | 5691 |
| TC4A | 6319 | 4706 |
| TC5A | 6528 | 5589 |
| TC6A | 6773 | 6099 |
| TC7A | 6456 | 6016 |
| TC8A | 5762 | 5376 |
| TC9A | 6715 | 5929 |
| Set #2 | | |
| TC16A | 1762 | 1964 |
| TC17A | 1758 | 2063 |
| TC18A | 1543 | 1822 |
| TC19A | 1766 | 1987 |
| TC20A | 1578 | 1708 |
| TC21A | 1604 | 1540 |
| TC22A | 1700 | 1812 |
| TC23A | 1656 | 1832 |
| TC24A | 1417 | 1408 |
| TC25A | 1255 | 1555 |
| Set #3 | | |
| TC28A | 8084 | 7690 |
| TC29A | 7519 | 6887 |
| TC30A | 7449 | 7404 |
| TC31A | 7294 | 6697 |
| TC32A | 7284 | 6529 |
| TC33A | 7724 | 6919 |
| TC34A | 7236 | 7282 |
| TC35A | 7758 | 7258 |
| TC36A | 7410 | 7089 |
| TC37A | 7291 | 7583 |
| TC38A | 7353 | 6760 |
| TC39A | 6370 | 6321 |
| TC40A | 6754 | 6722 |
| TC41A | 6183 | 5502 |
| TC42A | 5758 | 5501 |
| TC43A | 7137 | 7013 |
| TC44A | 5576 | 5335 |
| TC45A | 4920 | 4917 |
| TC46A | 6261 | 5030 |
| TC47A | 6057 | 5206 |
| TC48A | 5051 | 4109 |

3. Relationships between hybridizations. Hierarchical clustering of the hybridizations in each set provides an additional, albeit preliminary, estimate of quality. Either the Pearson correlation coefficient or a standard Euclidean distance was used as the distance measure between differential hybridization vectors. Hybridizations were clustered according to these distances by average linkage hierarchical clustering. Missing values were deleted on a case-wise basis. Clusters of hybridizations can be identified and evaluated in light of existing knowledge.

Many of the unexpected phenomena can indicate the limitation of previous understanding, and serve as a starting point for class definition. However, "outlying" hybridizations can also indicate quality problems. Overall, in each set (FIGS. 1–4) most of the separation between hybridizations is consistent with the expected TCC and normal urothelium separation. Even in hybridizations of lower quality, such as those of the second set, a clear separation between TCC and normal samples is observed.

One of the TCC samples in the first set (TC6) is such an "outlyer" (FIG. 1), as well as one of the normal samples in the second set, and another normal sample (TC35) in the third. (The "outlyers" do not appear to be misclassifications). For example, TC35 (a normal sample which is an "outlyer" in the third set) does not behave like a TCC sample. Rather those genes that are up-regulated in TCC samples are down-regulated in TC35).

None of the "outlyers" was eliminated from subsequent analysis steps. Rather, they were included to facilitate the selection of a more robust marker set (FIGS. 1–4). Here, more complex relations are observed between global expression profiles. First, the two invasive hybridizations (TC34 and TC45), are distinct from other TCC samples (FIGS. 1–6). Second, the relationship between global Ta and T1 profiles is not straightforward. Most of the Ta samples form a unique cluster in the 3rd set, while the T1 samples are more dispersed.

Section 3. Pro-Processing of the Hybridization Data.

All hybridization data, even of good global quality, was filtered and processed prior to additional large scale analysis. This included global balancing of signals, identification and treatment of problematic signals, normalization of the hybridization data and filtering.

1. Signal Balancing. Differences in labeling and hybridization can bias the signals obtained with a Cy3 probe relative to the Cy5 probes. For each hybridization, linear balancing is used to overcome this bias. The balancing coeffient is calculated as (sum P1)/(Sum P2).

2. Problematic signals. Two types of problematic signals are identified: very low signals and exceptionally variable signals. The first are signals below a pre-set threshold. The second are common control signals which significantly (>2 SDs) deviate from the average common control signal for a given element. All problematic common control signals were replaced with the average signals for the common control in the given element.

3. Normalization. In order to obtain meaningful differential expression values (TCC vs. normal) and to reduce differences between sets (inter-block variance), a second step of normalization is performed. In this step, each of the balanced differential expression levels (relative to the common control) is normalized by the average differential expression of the given element in the normal samples of the same set. The resulting normalized differential values give a measure of the difference between the expression of the element in a given sample (normal or TCC) and the average expression levels in normal tissues. Note that due to the use of averages in replacement of problematic signals, the variability in the normal samples is reduced by this procedure.

4. Filtering. In order to reduce the data set and limit it to higher-quality elements there was restricted from further analysis any overall weak elements (no signal above 200) and any non-differential elements (for which no normalized differential values exceeds 11.71). The remaining number of elements following these filters is 6693. Low-quality elements (where more than 20% of signals are problematic) were filtered only in later stages.

Section 4. Class Prediction: Normal Urothelium vs. Non-Invasive TCC and Selection of Marker set of Genes To discriminate between normal urothelium and non-invasive TCC, each of the gene with hybridization value is scored according to its "similarity" to the desired discrimination— N vs Non invasive TCC. Two independent (though related) standard scoring methods from the three described below were used.

Statistical Methods for Class Prediction

Scoring Methods a. Students unpaired t-test: The t-test is a statistic for measuring the significance of a difference of the means between two distributions (m1, and m2) considering the variance (s21 and s22) within each group. The two populations are expected to be drawn from a normal distribution. In the case, these are the mean expression levels of a gene in normal urothelium and in TCC tumors, which are supposed to have a log-normal distribution (thus, log values are used). Statistical significance estimates (p-values) available for the t statistic. Since a large number of measurements is available for a small number of samples, a much more stringent threshold of significance is used (p<1–6), which, according to the Benferroni adjustment corresponds to p<0.001.

a. estimation of prediction error: This method scores genes according to probability of error or misclassification. As part of this procedure a discrimination threshold is determined. The threshold $T(g_j)$ is taken such that the two types of misclassification error become equal, as:

$$(D.1) T(g_j) = [m1(g_j)*s2(g_j) + m2(g_j)*s1(g_j)]/[s1(g_j) + s2(g_j)]$$

and the significance of the misclassification error is given by $$(D.4) P = 1 - F[(T(g_j) - m2(g_j))/s2(g_j)]$$

where F is a distribution function N(0,1).

b. Receiver Operating Characteristics (ROC) curves. ROC curves are used to evaluate the power of a classification method for different asymmetric weights of false negative vs. false positive errors (or sensitivity vs. specificity). In diagnostic applications false negative errors can be detrimental while false positives can be tolerated. A ROC curve plots the tradeoff between the two types of errors as the classification threshold varies. For each potential threshold, the rate of true positives is plotted against the rate of false positives. Accuracy (A) is indexed by the area under the curve. A straight line (i.e. 50:50 chance of correct diagnosis, no better than chance), has A=0.5. Perfect accuracy (A=i) means that for a given threshold all predictions are correct.

The first score used is the "student's unpaired t-test", as above-described, i.e., one-way ANOVA with two classes, which reflects the difference between the classes relative to the variance within classes. The distribution of this statistic is resolved and significance levels of each score (its p-value) can be derived. The second method used scored genes according to an "estimation of prediction error", as described above, which again provides significance estimates (p-values) in a straightforward way.

Both scoring methods yielded similar numbers of elements with statistically significant scores: 77 elements according to the t-test scores (p<10), and 63 elements with low misclassification errors.

This list was further narrowed according to several additional considerations:

1. Exclusivity of up-regulated genes. Non-invasive tests, such as a urine test, require the identification of tumor cells or proteins on a considerable background of normal tissue. Since the inventors assume that only significantly up-regulated TCC genes have a chance to be detected on such background, while genes down-regulated in TCC are not be faithfully detected in non-invasive tests, they specifically selected such genes according to their normalized differentials. Furthermore, genes having a particularly low expression in normal tissues were prioritized, to minimize detection problems in further assays.

2. Consistent scores. Elements with high scores in both methods were prioritized in the final list. The error-based method was given preference over the t-test scores due to the prediction thershold it provides.

3. Redundancy. Approximately half of the clones on the array were derived by a subtraction procedure (SSH) enriching for TCC up-regulated clones. Inevitably, this significantly increases array redundancy, especially for up-regulated genes. In order to address this problem, a large portion of the significantly scored clones and up-regulated genes has been sequenced (~900 clones). Only a single representative of each redundancy group was retained in the list.

4. Element quality. A stricter threshold of element quality was added, and only elements with less than 8 problematic signals were included (in most genes a much smaller number of problematic signals was encountered).

5. Gene identity. The functional role fulfilled by different genes as well as previous knowledge can change their priority. For example, one low-scoring gene (FABP) was selected due to its involvement in psoriasis and squamous cell carcinoma of the bladder.

Section 5. Expression Patterns, Scores and Significance Values for the 22 Short-Listed Genes of the Invention The final subset of informative genes comprises the top 22 up-regulated genes after application of consistency, redundancy, and quality filters. These genes obtained high scores as discriminators by both scoring methods.

The differential expression patterns, statistical scores and significance values for the 22 selected genes are shown in Table C1. The expression levels are shown in the Table in the following order:

Normal urothelium (16 first hybridizations);

T1 samples (13 hybridizations);

Ta samples (10 hybridizations).

The levels of differential expression and the signal values of the 2 "Secreted" probes are also shown (Table C1, four columns headed "Secreted . . . "). Strong negative differentials indicate a gene potentially encoding a secreted or membranal protein.

The statistical scores are given in the following order:

1. Estimation of mis-classification error is given under column "Error1_2", 2. P value-Fisher criteria (similar to T-test) is shown as P-values, (column "PvalueFisher"), and 3. ROC value in the column headed with the same name.

Figure 7:
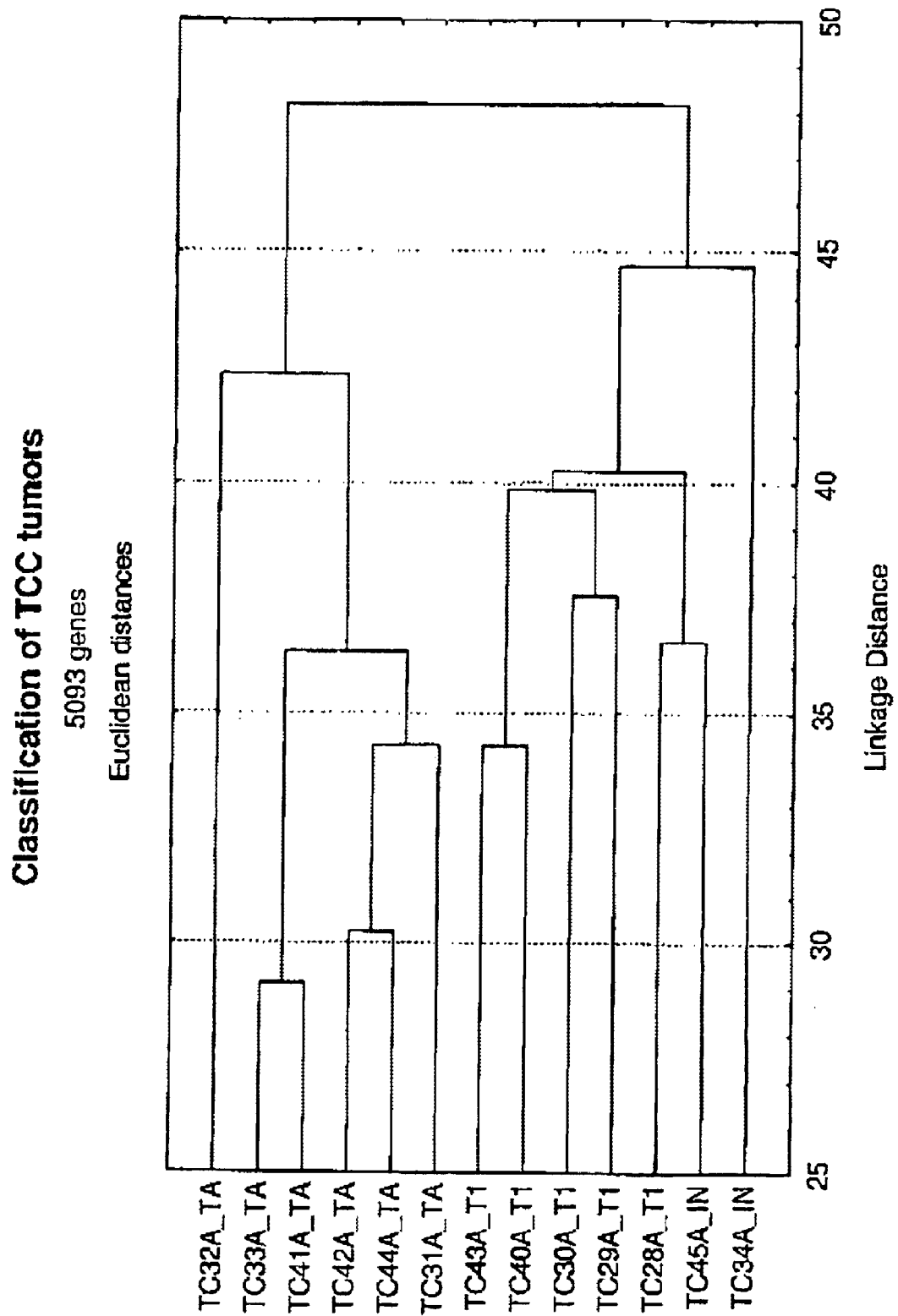
FIG. 7: This figure shows relationships between hierarchical clustering of tumor samples ($3^{rd}$ Set). The standard Euclidean distance was used as the distance measure between tumor samples.

Table C2 includes the raw measured signals for each gene in 39 hybridizations. P1 are the common control signals. P2 signals represent the measured tissue samples, and are thus more interesting. The genes are sorted by statistical significance with the top gene having the highest score. This is also the order in which they have been incorporated into the predictor (FIG. 7).

Section 6. Sequence Annotation and Bioinformatic Analysis of the Genes with Unknown Protein Product As shown in Table A, set 4, based on sequence annotation, 17 of the selected 22 markers are known, characterized genes; 3 additional genes code for hypothetical proteins. (One of these hypothetical proteins was identified through an EST contig of the original clone). The remaining 2 clones code for novel sequences. For one of them an EST contig was assembled, but homologous genes were not found. Only limited information is available for the 5 novel or uncharacterized genes. According to the "Secreted" probe, as described herein, one of them, the CGI-81 hypothetical protein, is a potentially secreted or membranal protein. Domain analysis also indicated the presence of a transmembranal domain in this protein. The other four genes cannot be classified with confidence, although the unknown gene in clone 70E8, can be marginally classified as "potentially secreted". No additional significant domains were identified.

Section 7. Bioinformatic Analysis of Known Genes

According to the biomedical literature, the 17 known genes were classified into three functional groups: tumorigenesis, keratinocyte differentiation, and cell motility and proliferation. Thus, these markers fulfil a functional role in TCC. It was noted that in a previous analysis, performed with sample pools on a general-purpose human microarray, similar functional groups (and in some cases the same genes) were identified, further validating the results of this study (see co-assigned patent application U.S. Ser. No. 09/534,661 corresponding to PCT patent publication number WO 00/56935).

Only a few of these 17 markers were previously considered related to or implicated in bladder cancer. These are the keratin family of proteins, some of which are known TCC markers, midkine, for which a single report (PMID: 8653688) implies its connection to invasiveness in TCC; and FABP-5 which is related to squamous cell carcinoma of the bladder. A number of the other markers have been found to be related to other cancers, to varying extents. The specificity of markers for TCC over other cancers is an important consideration.

Four of the known up-regulated genes which are related to tumorigenesis are either membranal or secreted. Three of them were not previously reported in TCC, and the fourth (midkine) has been related to TCC invasiveness. Clearly, secreted and membranal proteins have a unique advantage for the development of a diagnostic test.

Intriguing amongst the functional group are markers related to keratinocyte differentiation. The keratins, which are cytoskeletal proteins, are known markers for keratinocyte differentiation. Five different keratins were detected in the top-scoring genes. Two of them are known to be TCC markers. The remaining three (KRT 7, 8, 17) were included in the 22 marker set. Expression of some of these and other keratins has been tested in the past by several research groups using different experimental approaches. Non-consistent findings as to their regulation in TCC were reported. Thus, specific typing of the different keratins in urine of TCC patients, using a single multi-gene assay, can facilitate and improve robust TCC diagnostics.

A second major group of markers associated with keratinocyte differentiation are the S100 proteins. These are low-molecular-weight calcium-binding proteins which are probably involved in the regulation of a number of cellular processes including cell cycle progression and cell differentiation. Four different S100 proteins (S100A11, A6, A13, P) are included in the marker set. None has been previously associated with TCC. S100 proteins were implicated in other cancers (AML, colorectal). The S100P was found to be down-regulated upon androgen depletion in the androgen-dependent prostate cancer cell line LnCap. Another S100 protein, psoriasin (S100A7, not included in the set), is involved in both invasive breast cancer, squamous cell carcinoma of the bladder and psoriasis, another disease involving keratinocytes. Note, that another psoriasis-related gene, PA-FABP is also included in this proposed marker set. PA-FABP has also been implicated in squamous cell carcinoma of the bladder. Interactions between another FAPB (E-FABP) and psoriasin are well-documented in psoriatic keratinocytes. The identified S100 proteins and PA-FABP are important novel markers for TCC.

Section 8. Sequence Annotation of Genes with Identical Expression Pattern in all Tested Samples The diagnostic assay is based on the genes which are up-regulated in TCC. In all suggested tests, and mainly in the RT-PCR based assay, internal controls for each tested sample are beneficial. Such controls can be genes which are normally not upregulated in TCC. To this end the hybridization data was analyzed to identify genes which are:

1. Expressed at a high, easily detectable level in all the control and TCC samples. This is important to enable detection even in small amounts of RNA.

2. Genes which are not differential in TCC compared to normal urothelium. Such genes were specifically selected according to their normalized differentials 14 genes were detected as suitable according to these criteria (Section 9 hereunder). These genes are included in the diagnostic assays, and used as internal references for a normally, uniformly expressed gene in TCC and in non-TCC cases.

Section 9: Expression Patterns, Signals and Annotation Report for Control Genes

The differential expression patterns and basic annotation for the 14 non-differential genes suggested as internal controls is provided in Table E (at end of specification, just before Table 1). Table E displays differential expression results, and shows signals of all genes in all hybridizations.

The expression levels are shown in the following order:

Normal urothelium (16 first hybridizations)

T1 samples (13 hybridizations)

Ta samples (10 hybridizations).

All 14 clones were fully sequenced from both sides. Full (contigized) sequences passed via the standard sequence annotation platform including sequence QC, chimer detection, and homology searches within Genbank's non-redundant genomic and non-genomic nucleotide databases, the non-redundant protein database and the EST database. EST contigs were assembled for several novel genes for which ESTs were available, and further annotated.

The results supported the choice of any one, or a combination of two or more, of these 14 genes as internal controls.

Section 10. Class Definition and Characterization

Staging and grading of TCC is not straightforward. In fact, subjective decisions must often be made in order to classify tumors, and pathological experts can differ on the correct diagnosis. Unsupervised analysis methods as well as supervised methods of class prediction were used, in order to reduce the dependence on expert opinion.

During the quality control process (section 2), some separation between T1 and Ta samples was noted in the third set of experiments, as well as in global clustering of all 41 profiles (39 normal or non-invasive, plus 2 invasive TCC samples). Therefore clustering of the tumor samples within the third set only (FIG. 7) was pursued. This set contains the largest and most variable collection of TCC samples. A clear differentiation exists between Ta and T1 tumors. One tumor classified as T1/Ta resides within the Ta cluster, but is separated from other Ta tumors. The two invasive tumor samples are in the T1 cluster (one clearly inside, the other outlying). Thus at the level of hierarchical clustering Ta tumors are separated from T1 high-grade tumors.

Standard scoring method (example 5, section 4) was employed for class prediction in order to identify specific molecular markers that underlie the Ta/T1 separation.

The Keratin 13 gene was found to be the highest scoring gene. It is down-regulated in T1 samples and up-regulated in Ta (relative to normal samples). Keratin 13 is known to be expressed in urothelium. Its expression in urothelial tumors depends on their degree of differentiation. It is expressed only in well-differentiated tumors and absent from poorly differentiated ones (PMID: 1706547). Since most of the Ta tumors in this set were classified as low grade while the T1 tumors were mostly high grade, over-expression of the KRT13 gene can be attributed to the degree of the differentiation as well as to the staging of the tumors.

The expression pattern of KRT13 in all TCC hybridizations was then studied. The results are not straightforward. Approximately half of the tumors show up-regulation of KRT13, while down-regulation is observed in others, with no clear correlation to either stage or grade of the tumor. KRT13 is highly relevant to the sub-classification of TCC tumors. However, the exact correlation to the classical clinical classifications remains to be elucidated in a larger set of tumors involving different stages and grades and in follow-up studies.

Example 5

Bioinformatics Analysis of 22 Shortlisted Genes

1. Sequence—All clones were fully sequenced from both sides. Sequence passed the standard sequence criteria, except where otherwise noted (see Table 6)

2. Annotation—Full (contigized) sequences were passed through the standard sequence annotation platform including sequence QC, chimer detection, and homology searches to Genbank's non-redundant genomic and non-genomic nucleotide databases, the non-redundant protein database and the EST database. EST contigs were assembled for several novel genes for which ESTs were available, and further annotated. Complete annotation and sequence information is available in Table 5.

3. Literature—an extensive search of the literature was performed for each of the known genes. Detailed information is given below. Known genes are classified according to their function in tumorigenesis, keratinocyte differentiation, and cell motility and proliferation. References are given as PMIDs.

3.1 Genes Associated with Tumorigensis

Genes Coding for Secreted and Membranal Proteins 3.1.1. Syndecan 1 (Accession: gi|45068581|ref|NM_002997.1|)

An integral membrane protein, 310 amino acid-long, with a signal peptide at its $NH_2$-terminus. Contains a matrix-interacting ectodomain with putative glycosaminoglycan attachment sites, a hydrophobic membrane-spanning domain and a cytoplasmic domain. Is connected to cell aggregation in malignant mesotheliomas with epithelial and/or sarcomatous morphology and is required for wnt-1-induced mammary tumorigenesis in mice. On the other hand, its expression is inversely correlated to the aggressiveness of basal cell carcinoma. PMID: 2324102, 10912783, 10888884, 10770430.

3.1.2. Hepatocyte Growth Factor Activator Inhibitor Type 2 (HAI-2) (Accession: gi|2924619|dbj|AB00534.1|AB006534)

HAI-2 is a Kunitz-type serine protease inhibitor which was recently identified as a potent inhibitor of hepatocyte growth factor activator. It was also independently reported as placental bikunin (PB) and as a protein over-expressed in pancreatic cancer. However, its expression was conserved in the neoplastic colorectal mucosa, and no relationship was found between HAI-2/PB mRNA levels and colorectal tumor stages. HAI-2 is produced in a membrane-associated form and secreted in a proteolytically truncated form. PMID: 10695988, 10762618.

3.1.3. Midkine (Neurite Growth Promoting Factor) (Accession: gi|4505134|ref|NM_002391.1|)

Midkine is a heparin-binding growth factor, implicated in various biological phenomena such as neuronal survival and differentiation, tissue remodeling and carcinogenesis. In the G401 cell line, midkine initiates a cascade of intracellular protein tyrosine phosphorylation mediated by the JAK/STAT pathway after binding to its high affinity p200(+)/MKR cell surface receptor. The most intriguing feature of midkine in cancer is its augmented expression in advanced tumors at a very high frequency in a non-tissue specific manner. In addition, its high expression is also detected in precancerous lesions. Midkine exerts carcinogenesis-related activities, including transforming, anti-apoptotic, angiogenic and fibrinolytic ones. These data provide a possibility of clinical application of midkine. Serum midkine level can be a useful tumor marker. Gene therapy using its promoter region and therapeutic strategy choosing midkine as a molecular target were also suggested. MK was suggested as a marker for early and latent bladder cancer disease (specificity of 0.86). Recent publication demonstrated good correlation of MK over-expression with poor outcome in patients with invasive cancers. PMID: 10879061, 8714367, 10902971, 10626184, 10545795, 10408712.

3.1.4. Solute Carrier Family 2 SLC2A1 (GLUT1) (Accession: gi|5730050|ref|NM_006516.1|)

Increased expression of glucose transporters (GLUT1) has been reported in many human cancers. Suppression of GLUT1 mRNA has been shown to suppress tumor growth. Some studies have reported associations between its expression and proliferative indices, whilst others suggest that GLUT1 can be of prognostic significance, especially in lung cancer. No connection between GLUT1 up-regulation and TCC has yet been reported. PMID: 10983690, 10806305, 10795374.

Genes Coding for Intracellular Proteins 3.1.5. Cystatin B (Accession: gi|7263011|gb|AF208234.1|AF208234)

Cystatins are endogenous inhibitors of lysosomal cysteine proteinases, the cathepsins (Cats). Imbalance between cathepsins and cystatins, associated with metastatic tumor cell phenotype, can facilitate tumor cell invasion and metastasis. Cystatins were found to be up-regulated in relation to inflamation and cancer (breast, lung, brain and head and neck tumors, and in body fluids of ovarian, uterine, melanoma and colorectal carcinoma). In contrast, reduced expression of cystatin B was found in esophageal-carcinoma tissue and was associated with lymph-node metastasis. The application of cystatins for prognosis, diagnosis, follow-up and anticancer therapy has been proposed (but not for TCC). In the preliminary experiments in TCC, using general microarray containing 10,000 human ESTs, Cystatin A was found to be up-regulated in TCC pool compared to pool of normals. PMID: 10566975, 9769367, 9583733, 10514828.

3.1.5 Opa-Interacting Protein OIP3 (Accession:gi|2815605|gb|AF025439.1|AF025439)

Opa proteins are a family of outer membrane proteins involved in gonococcal adherence to and invasion of human cells. Pyruvate kinase M2 is OIP3 which binds to OPA proteins. Modulation of type M2 pyruvate kinase activity by the human papillomavirus type 16 E7 oncoprotein has been demonstrated. PMID: 9990017, 9692838.

3.2 Genes Associated with Abnormal Differentiation of Keratinocytes

Aid 3.2.1. Keratins: keratin 19, keratin 7, keratin 8, keratin 18, keratin 17

Keratins, or cytokeratins, represent a family of more than 20 different polypeptides which are important markers of epithelial cell differentiation. Both gene expression and protein levels are elevated (and even used as a marker) in several pathological conditions including breast cancer, kidney tumors, small cell lung cancer (SCLC), and pre-eclampsia. Measurements of cytokeratins 19 and 20 levels in serum and urine are in use as tumor marker for bladder cancers.

Keratin 18 is a type-1 keratin that is found in a variety of simple epithelial tissues. Pancreatic exocrine acinar cells and endocrine islet cells are well-differentiated cells which express the keratin combination 8 and 18, whereas the less-differentiated cells of the ductal tree are characterized by the additional expression of keratin 7, keratin 19, and, in the rat, keratin 20. Levels of keratin 7 and 20 are increased in rectal adenocarcinoma and Paget's disease. PMID: 10755601, 10707834, 10782894, 10775728, 10762743, 9614373, 8911513, 9445193, 2434380.

3.2.2. S100 Proteins: S100A11, S100P, S100 Calcium Binding Protein A13, S100A6

S100 proteins are low-molecular-weight calcium-binding proteins of the EF-hand superfamily and appear to be involved in the regulation of a number of cellular processes such as cell cycle progression and differentiation. More than 10 members of the S100 protein family have been described from human sources so far. Induced expression in tumors of some of these genes has been reported.

S10A11 (or S100C/Calgizzarin)

Calgizzarin is a nuclear protein which inhibits the actin-activated myosin Mg(2+)-ATPase activity of smooth muscle in a dose-dependent manner. Other Ca(2+)-binding proteins such as S100A1, S100A2, S100B, and calmodulin do not inhibit actin-activated myosin Mg(2+)-ATPase activity. Calgizzarin can be involved in the regulation of actin-activated myosin Mg(2+)-A Pase activity through its Ca(2+)-dependent interaction with actin filaments. It is expressed in most tissues and cell lines, and co-localized with the psoriasin gene S100A7 and other S100 genes to human chromosome 1q21q22.

Calgizzarin was found to be remarkably elevated in colorectal cancers compared with that in normal colorectal mucosa. No similar alteration in expression was detected in breast cancer. PMID: 10486266, 10623577, 7591220, 7889529.

S100P (Accession: gi|5174662|ref|NM_005980.1|)

S100P overexpression is an early event that might play an important role in the immortalization of human breast epithelial cells in vitro and tumor progression in vivo. S100P expression was downregulated after removal of androgen from LnCAP prostate cancer cell line. PMID: 10639564, 8977631.

S100 Calcium Binding Protein A13 (Accession: gi|5174658|ref|NM_005979.1|)

S100A13 was found to be widely expressed in various types of tissues including skeletal muscle, heart, kidney, ovary, small intestine and pancreas. It was shown to bind anti-allergic drugs and thus to be involved in the inhibition of degranulation of mast cells. Also, it was shown to be involved in the regulation of FGF1 activity. PMID: 10722710, 8878558, 9712836, 10051426.

Growth Factor Inducible 2a9/calcyclin/S100A6 (Accession: M14300)

2A9 was isolated from stimulated quiescent fibroblasts. It is induced by growth factors and over-expressed in AML. S100A6 was also suggested to be involved in the progression and invasive process of human colorectal adenocarcinomas. PMID: 10656447, 1952954.

3.2.3 PA-FABP-Fatty Acid Binding Protein 5 (Psoriasis-Associated)

(Accession: gi|4557580|ref|NM_001444.1|)

The fatty acid-binding protein (FABP) family consists of small, cytosolic proteins believed to be involved in the uptake, transport, and solubilization of their hydrophobic ligands. PA-FBP can be involved in keratinocyte differentiation. In normal skin, PA-FABP is expressed in basal and prickle cell layers, and more strongly in the granular cell layer. In psoriatic skin, PA-FABP is expressed in suprabasal layers and more strongly in more differentiated keratinocytes. In squamous cell carcinoma, PA-FABP shows very strong expression in squamous nests. Serum levels of intestinal fatty acid-binding protein (1-FABP) serve as diagnostic marker for mesenteric infarction (acute ischemic diseases of the bowel). Expression of PA-FABP has been linked to squamous cell carcinoma of the bladder. PMID: 9521644, 9438903, 8566578, 8092987, 9307301.

3.3 Genes involved in Cell Motility and Proliferation 3.3.1 Actin Gamma 1 (Accession: gi|4501886|ref|NM_001614.1|gi|4501886|ref|NM_001614.1|)

Ubiquitously expressed in all eukaryotic cells. Beta and gamma actins co-exist in most cell types as components of the cytoskeleton and as mediators of internal cell motility.

3.3.2 37 kD Laminin Receptor Precursorp40 Ribosome Associated Protein (Accession: HSU43901)

The 37 kD precursor of the 67 kD laminin receptor (37LRP) is a polypeptide whose expression is consistently up-regulated in aggressive carcinoma. Interestingly, the 37LRP appears to be a multifunctional protein involved in the translational machinery and has also been identified as p40 ribosome-associated protein. It is distributed on the cell surface as laminin binding protein p67 (LBP/p67), in the nucleus, and on 40S ribosomes. PMID: 8760291, 10079194.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the described invention, the invention can be practiced otherwise than as specifically described.

TABLE E

| Index | GeneDescription 1 | AccI |
|---|---|---|
| 1 | Human 54 kDa protein mRNA, complete cds; nt_non_genomic(identity) REPEAT: config_TCC_29E6_RF.fa | gi|407307|gb|U02493.1|HSU02493 |
| 2 | none:11_TCC_74D3_1_M13F.fa none:25_TCC_74D3_1_M13R.fa | |
| 3 | (AL121586) dJ47704.1 (novel protein similar to oroferlin and dysferlin) (*Homo sapiens*); nr(identity):10_TCC_70E2_1_M13F.fa *Homo sapiens* serine protease inhibitor, Kunitz type, 2 (SPINT2), mRNA; nt_non_genomic(identity):24_TCC_70E2_1_M13R.fa | gi|7671662|emb|CAB89410.1| gi|10863908|ref|NM_021102.1| |
| 4 | *Homo sapiens* full length insert cDNA clone ZC48G12; nt_non_genomic(identity): config_TCC_75B7_RF.fa | gi|3483555|gb|AF086210.1|HUMZC48G12 |
| 5 | *Homo sapiens* GPI-anchored metastasis-associated protein homolog (C4.4A), mRNA; nt_non_genomic(identity):config_TCC_89H5_RF.fa | gi|7656943|ref|NM_014400.1| |
| 6 | *Homo sapiens* cDNA: FLJ22720 fis, clone HSI1432D; nt_non_genomic(identity): 16_TCC_101D4_1_M13F.fa ANKHZN protein {*Homo sapiens*}300.1 | (AB037360) ANKHZN (*Homo sapiens*); nr(identity):30_TCC_101D4_1_M13R.fa | gi|10439219|dbj|AK026373.1|AK026373 gi|7705278|ref|NP_057460.1| |
| 7 | low molecular mass ubiquinone-binding protein (*Homo sapiens*) | UCRQ_HUMAN UBIQUINOL-CYTOCHROME C REDUC; nr(identity):config_TCC_67C11_RF.fa | gi|7657486|ref|NP_055217.1| |
| 8 | none:14_TCC_79B1_1_M13F.fa *Homo sapiens* quiescin Q6 (QSCN6), mRNA; nt_non_genomic(identity):28_TCC_79B1_1_M13R.fa | gi|4506360|ref|NM_002826.1| |
| 9 | *Homo sapiens* mRNA; cDNA DKFZp564C2282 (from clone DKFZp564C2282); nt_non_genomic(identity):config_TCC_74H12_RF.fa | gi|7328021|emb|AL161965.1|HSM802543 |
| 10 | *Homo sapiens* full length insert cDNA clone ZC48G12; nt_non_genomic(identity): config_TCC_56G1_RF.fa | gi|3483555|gb|AF086210.1|HUMZC48G12 |
| 11 | — | |
| 12 | NADH dehydrogenase (ubiquinone) 1, subcomplex unknown, 2 (14.5kD, B14.5b) (*Homo sapiens*) | N4BM_HUMAN; nr(identity):config_TCC_60B2_RF.fa | gi|4758784|ref|NP_004540.1| |
| 13 | — | |
| 14 | — | |

| Index | GeneID | TC7A_BDE_DIFF | TC8A_BDE_DIFF | TC9A_BDE_DIFF | TC10A_BDE_DIFF | TC11A_BDE_DIFF | TC22A_BDE_DIFF | TC21A_BDE_DIFF | TC23A_BDE_DIFF |
|---|---|---|---|---|---|---|---|---|---|
| 1 | TCC-29E_6 | −1 | −1.2 | 1.1 | 1 | 1.2 | −1.1 | 1.3 | −1.2 |
| 2 | TCC-74D_3 | −1.1 | −1 | 1.2 | −1.1 | −1 | 1.1 | 1 | 1 |
| 3 | TCC-70E_2 | −1.2 | 1.1 | 1.2 | −1.1 | −1.1 | 1.2 | 1.1 | 1 |
| 4 | TCC-75B_7 | −1.1 | 1 | 1.2 | −1.2 | −1 | 1.1 | −1 | 1 |
| 5 | TCC-89H_5 | −1.1 | −1 | 1.1 | 1 | −1 | 1.2 | −1 | 1.1 |
| 6 | TCC-101D_4 | −1.1 | −1.1 | 1.1 | −1.1 | 1.2 | 1.1 | 1.1 | 1.1 |
| 7 | TCC-67C_11 | 1 | −1.1 | −1 | 1 | 1.1 | 1.1 | 1.1 | −1 |
| 8 | TCC-79B_1 | −1.1 | 1 | 1.2 | −1.1 | −1 | 1.1 | −1 | 1.1 |
| 9 | TCC-74H_12 | −1.1 | −1.1 | 1.3 | −1.1 | 1 | 1.2 | 1.2 | −1 |
| 10 | TCC-56G_1 | −1 | −1 | 1.3 | −1.1 | −1.1 | 1.2 | 1 | 1 |
| 11 | TCC-47D_9 | 1.1 | 1+ | −1 | −1.1 | −1 | −1.3 | 1.4 | −1.1 |
| 12 | TCC-60B_2 | −1 | 1* | −1.1 | −1.1 | 1.3 | −1 | 1.2 | −1.1 |
| 13 | TCC-23D_4 | 1.1 | −1.4 | −1.2 | 1.2 | 1.3 | −1.2 | 1.1 | 1.1 |
| 14 | TCC-20F_5 | −1.2 | 1.1 | 1.2 | −1.2 | 1.1 | 1.1 | 1 | 1.1 |

| Index | TC24A_BDE_DIFF | TC47A_BDE_DIFF | TC36A_BDE_DIFF | TC38A_BDE_DIFF | TC46A_BDE_DIFF | TC48A_BDE_DIFF | TC37A_BDE_DIFF | TC35A_BDE_DIFF | TC2A_BDE_DIFF | TC3A_BDE_DIFF |
|---|---|---|---|---|---|---|---|---|---|---|
| 1 | 1+ | −1 | 1.1 | −1.1 | 1.1 | 1.4 | −1 | −1.5 | 1.1 | −1.2 |
| 2 | −1.2 | 1 | 1 | 1.3 | 1.3 | 1.1 | −1 | −1.8 | −1.5 | −1.1 |
| 3 | −1.4 | 1.2 | −1 | 1.3 | 1.3 | 1.2 | −1.1 | −2.1 | −1.3 | −1.5 |
| 4 | −1.2 | 1.1 | −1 | 1.3 | 1.3 | 1.1 | −1 | −1.9 | −1.2 | 1 |
| 5 | −1.2 | 1.1 | 1 | 1.3 | 1.3 | 1.1 | −1 | −1.9 | −1.3 | −1.1 |
| 6 | −1.3 | 1.1 | −1.1 | 1.2 | 1.3 | 1.1 | −1.1 | −1.7 | −1.2 | −1.1 |
| 7 | −1.2 | −1 | −1 | 1.2 | 1.1 | 1 | −1.2 | −1.2 | −1.4 | 1.1 |
| 8 | −1.2 | 1.1 | −1 | 1.2 | 1.3 | 1.1 | −1 | −1.8 | −1.2 | −1 |
| 9 | −1.4 | 1.1 | −1.3 | 1.3 | 1.3 | 1.2 | −1.1 | −1.6 | −1.2 | −1.3 |
| 10 | −1.2 | −1 | 1.1 | 1.3 | 1.3 | 1.1 | −1.1 | −1.8 | −1.4 | −1 |
| 11 | 1+ | −1.1 | −1 | −1.1 | 1.2 | 1.3 | 1.2 | −1.7 | −1.2 | −1.2 |
| 12 | 1+ | 1.1 | −1.2 | −1.1 | 1.3 | 1.1 | −1.1 | −1.2 | 1 | 1.2 |
| 13 | 1+ | −1.1 | 1.1 | −1 | 1.1 | 1.3 | 1.1 | −1.7 | −1.1 | −1.2 |
| 14 | −1.2 | 1 | −1.2 | 1.1 | 1.1 | 1.1 | −1 | −1.3 | −1 | 1.1 |

| Index | TC4A_BDE_DIFF | TC5A_BDE_DIFF | TC6A_BDE_DIFF | TC16A_BDE_DIFF | TC17A_BDE_DIFF | TC16A_BDE_DIFF | TC25A_BDE_DIFF | TC19A_BDE_DIFF | TC20A_BDE_DIFF | TC32A_BDE_DIFF |
|---|---|---|---|---|---|---|---|---|---|---|
| 1 | 1.4 | 1.2 | −1.1 | −1 | −1.5 | −1 | 1.4 | 1.1 | 1.4 | −1.4 |
| 2 | 1 | 1.5 | 1.1 | 1 | 1.3 | 1.5 | 1.5 | 1.1 | 1.3 | −1.2 |
| 3 | −1.3 | 1.3 | −1 | 1.2 | 1.5 | 1.3 | 1.4 | 1.2 | 1.3 | −1.3 |
| 4 | −1.4 | 1.3 | 1.3 | 1.1 | 1.4 | 1.3 | 1.5 | 1.4 | 1.1 | −1.1 |
| 5 | −1.3 | 1.2 | 1 | 1.1 | 1.5 | 1.1 | 1.5 | 1.4 | 1.1 | −1.1 |
| 6 | −1.5 | −1 | −1 | 1 | 1.4 | 1.7 | 1.5 | 1.2 | 1.3 | −1.3 |
| 7 | 1.1 | −1 | −1 | 1 | 1.5 | 1.5 | 1.5 | 1.4 | 1.1 | −1.3 |
| 8 | 1.1 | −1.2 | 1 | 1 | 1.4 | 1.4 | 1.5 | 1.4 | 1.1 | −1.1 |
| 9 | −1.1 | 1.1 | −1.2 | 1.1 | 1.4 | 1.4 | 1.5 | 1.2 | 1.4 | −1.5 |
| 10 | −1.4 | 1.3 | 1.2 | 1.1 | 1.4 | 1.5 | 1.5 | 1.4 | 1.3 | −1.1 |
| 11 | −1.6 | 1.2 | −1 | 1.1 | −1.3 | 1 | 1.3 | 1.3 | 1.2 | −1.5 |

TABLE E-continued

| Index | TC33A_BDE_DIFF | TC41A_BDE_DIFF | TC42A_BDE_DIFF | TC44A_BDE_DIFF | TC31A_BDE_DIFF | TC39A_BDE_DIFF | TC43A_BDE_DIFF | TC40A_BDE_DIFF | TC30A_BDE_DIFF | TC26A_BDE_DIFF |
|---|---|---|---|---|---|---|---|---|---|---|
| 12 | −1.2 | 1 | 1 | 1.4 | 1.2 | 1.3 | 1.5 | 1.2 | 1.2 | −1.3 |
| 13 | −2 | 1.4 | 1.1 | −1.4 | −1.5 | −1.3 | 1.2 | −1 | −1.1 | −1 |
| 14 | −1.2 | −1.1 | −1.1 | −1.2 | 1.2 | 1.4 | 1.3 | 1.4 | 1.1 | −1.2 |
| 1 | −1.1 | −1.1 | −1.3 | −1.3 | −1.1 | −1.2 | −1.3 | −1.3 | −1.3 | 1.2 |
| 2 | 1.1 | 1.1 | 1.1 | 1.2 | −1.3 | −1.1 | −1.4 | −1.2 | 1.1 | −1.1 |
| 3 | −1.2 | 1.2 | −1 | 1.2 | −1.3 | −1.1 | −1.4 | −1.2 | 1.1 | −1.1 |
| 4 | −1 | 1.1 | 1.1 | 1.1 | −1.3 | −1.1 | −1.5 | −1.3 | 1.1 | −1 |
| 5 | −1 | 1.1 | 1 | −1.1 | −1.2 | −1.2 | −1.5 | −1.2 | 1.1 | −1.1 |
| 6 | −1.2 | 1.1 | −1.1 | −1 | −1.3 | −1.2 | −1.4 | −1.4 | 1.1 | −1.3 |
| 7 | −1.3 | 1.1 | −1 | −1 | −1.4 | −1.2 | −1.4 | −1.5 | −1 | −1.1 |
| 8 | 1 | 1.1 | −1 | 1.1 | −1.1 | −1.1 | −1.4 | −1.3 | 1.1 | −1.1 |
| 9 | −1.4 | 1.1 | −1.1 | 1.2 | −1.3 | −1.2 | −1.5 | −1.4 | 1.2 | −1.1 |
| 10 | 1 | 1.2 | 1 | 1.1 | −1.3 | −1.1 | −1.5 | −1.3 | 1 | −1.1 |
| 11 | −1.2 | −1.2 | −1.3 | −1.3 | −1 | −1.4 | −1.5 | −1.4 | −1.5 | 1.1 |
| 12 | −1.2 | −1.1 | −1.4 | −1.2 | −1.2 | −1.8 | −1.4 | −1.3 | −1.3 | −1.1 |
| 13 | −1.1 | 1 | −1.3 | −1.1 | 1.2 | −1.3 | 1 | −1.1 | −1.2 | 1.4 |
| 14 | −1.5 | −1 | −1.2 | −1.3 | −1.3 | 1 | −1.2 | −1 | −1.3 | 1.1 |

| Index | TC29A_BDE_DIFF | TC34A_BDE_DIFF | TC45A_BDE_DIFF |
|---|---|---|---|
| 1 | 1.2 | 1.1 | 1.1 |
| 2 | 1.2 | 1.4 | 1.1 |
| 3 | 1.1 | 1.3 | 1.2 |
| 4 | 1.1 | 1.2 | 1.1 |
| 5 | 1.1 | 1.2 | 1 |
| 6 | −1.1 | 1.1 | 1.1 |
| 7 | −1 | −1.1 | −1 |
| 8 | 1.2 | 1.4 | 1.1 |
| 9 | 1 | 1 | 1.3 |
| 10 | 1.1 | 1.3 | 1 |
| 11 | 1.2 | 1.1 | −1.1 |
| 12 | −1.2 | 1.2 | 1.1 |
| 13 | 1.4 | 1.3 | −1.1 |
| 14 | −1.2 | −1.2 | 1.2 |

TABLE 1

GeneDescription and clone ID

1. *Homo sapiens* keratin 19 (KRT19) gene, complete cd; nt_non_genomic(identity):47_TCC_91B11_M13F.TXT.fa
2. Human 40-kDa keratin intermediate filament precur; nt_non_genomic(identity):20_TCC_60H4_M13F.TXT.fa
3. Human mRNA fragment for mesothelial type II kerat; nt_non_genomic(identity):04_TCC_94G3_M13F.TXT.fa
4. *Homo sapiens* cystatin B (CSTB) gene, promoter reg; nt_non_genomic(identity):30_TCC_76B3_M13F_F04_042 ab1.TXT
5. *Homo sapiens* S100 calcium-binding protein P (S100P; nt_non_genomic(identity):29_TCC_48G1_M13F.TXT.fa
6. *Homo sapiens* syndecan 1 {SDC1} mRNA; nt_non_genomic(identity):26_TCC_75E3_M13F_804_032.ab1.TXT
7. *Homo sapiens* S100 calcium-binding protein A13 {S10; nt_non_genomic(identity):26_TCC_44C1_M13F.TXT.fa
8. *Homo sapiens* mRNA for hepatocyte growth factor ac; nt_non_genomic(identity):35_TCC_21D6_M13F_C05_037.ab1.fa
9. *Homo sapiens* midkine {neurite growth-promoting fac; nt_non_genomic(identity):82_TCC_89G3_M13F_B11_092.ab1.TXT
10. *Homo sapiens* solute carrier family 2 (facilitated; nt_non_genomic(identity):07_TCC_57B3_M13F.TXT
11. *Homo sapiens* S100 calcium-binding protein A11 (cal; nt_non_genomic(identity):31_TCC_65B9_M13F.TXT.fa
12. *Homo sapiens* fatty acid binding protein 5 (psorias; nt_non_genomic(identity):11_TCC_25F2_M13F.TXT
13. *Homo sapiens* Opa-interacting protein OIP3 mRNA, p; nt_non_genomic(identity):38_TCC_56E11_M13F.TXT
14. *Homo sapiens* glutaminyl-tRNA synthetase (QARS), m; nt_non_genomic(identity):46_TCC_78B11_M13F_F06_058.ab1.TXT
15. *Homo sapiens* anterior gradient 2 {Xenepus laevis}; nt_non_genomic(identity):25_TCC_50G5_M13F.TXT
16. *Homo sapiens* myristoylated alanine-rich protein k; nt_non_genomic(identity):10_TCC_53H11_TS
17. *Homo sapiens* leukemia-associated phosphoprotein p1; nt_non_genomic(identity):46_TCC_27H5_M13F_F06_056.ab1.fa
18. *Homo sapiens* type II membrane serine protease (LO; nt_non_genomic(identity):53_TCC_79G2_M13_FE07_054.ab1.TXT
19. *Homo sapiens* putative secreted protein XAG mRNA, c; nt_non_genomic(identity):26_TCC_50G6_M13F.TXT
20. *H. sapiens* {xscad} mRNA, 340bp; nt_non_genomic(identity):40_TCC_13F11_M13F.fa start here

| | Accession | GeneID | T1 TC2A_BDE_DIFF | T1 TC3A_BDE_DIFF | G2/3 T1 TC4A_BDE_DIFF | G2/3 T1 TC5A_BDE_DIFF | G2/3 T1 TC6A_BDE_DIFF | G1/2 T1 |
|---|---|---|---|---|---|---|---|---|
| 1 | gi\|6729680\|gb\|AF202321.1\|AF202321 | TCC-91B_11 | 3.7 | 3 | 5.4 | 1.5 | 3.1 | |
| 2 | gi\|184658\|gb\|J03607.1\|HUMIFP | TCC-60H_4 | 3.7 | 2.7 | 5.9 | 1.5 | 2.9 | |
| 3 | gi\|34067\|emb\|X03212.1\|HSKER7R | TCC-94G_3 | 3.3 | 2.7 | 6.3 | 3.1 | 1.6 | |
| 4 | gi\|7263011\|gb\|AF208234.1\|AF208234 | TCC-76B_3 | 5.7 | 2.2 | 3 | 1.6 | 1.3 | |
| 5 | gi\|5174662\|ref\|NM_005980.1\| | TCC-48G_1 | 2.7 | 4.8 | 8.9 | 1.7 | 1.7 | |

TABLE 1-continued

|   |   |   | | | | | |
|---|---|---|---|---|---|---|---|
| 6 | gi\|4506858\|ref\|NM_002997.1\| | TCC-75E_3 | 1.9 | 2.6 | 2.5 | 1 | 1.6 |
| 7 | gi\|5174658\|ref\|NM_005979.1\| | TCC-44C_1 | 3.1 | 4.8 | 9.3 | 1.6 | 1.6 |
| 8 | gi\|2924619\|dbj\|AB006534.1\|AB006534 | TCC-21D_6 | 1.1 | 1.1 | −2.2 | 2 | 1.8 |
| 9 | gi\|4505134\|ref\|NM_002391.1\| | TCC-89G_3 | 2.2 | 1.7 | 3.7 | −1.5 | 1.9 |
| 10 | gi\|5730050\|ref\|NM_006518.1\| | TCC-57B_3 | 4.8 | 1.2 | 2.2 | 1.2 | 3.2 |
| 11 | gi\|5032056\|ref\|NM_005620.1\| | TCC-65B_9 | 3.5 | 2 | 3.4 | 1.5 | 1.6 |
| 12 | gi\|4557580\|ref\|NM_001444.1\| | TCC-25F_2 | 2.1 | 2.3 | 1.1 | 2.6 | 5 |
| 13 | gi\|2815605\|gb\|AF025439.1\|AF025439 | TCC-56E_11 | 3.4 | 2.1 | 2.4 | 1.1 | 1.6 |
| 14 | gi\|4826959\|ref\|NM_005051.1\| | TCC-78B_11 | 2.2 | 2.6 | 5.3 | 1.6 | 1.6 |
| 15 | gi\|5453540\|ref\|NM_006408.1\| | TCC-50G_5 | 2.4 | 5.6 | 3.4 | −1.2 | 1.2 |
| 16 | gi\|4505082\|ref\|NM_002356.1\| | TCC-53H_11 | 1.6 | 1 | −1.6 | 1.6 | 1.7 |
| 17 | gi\|5031850\|ref\|NM_005563.1\| | TCC-27H_5 | 1.8 | 1.7 | 2 | 2.2 | 1.6 |
| 18 | gi\|7705976\|ref\|NM_016425.1\| | TCC-79G_2 | 5.6 | 2.6 | 7.2 | −1.6 | −1.2 |
| 19 | gi\|6652811\|gb\|AF088867.1\|AF088867 | TCC-50G_6 | 2.3 | 5.7 | 3.6 | −1.1 | 1.3 |
| 20 | gi\|533986\|emb\|Z36852.1\|HSXSCAD | TCC-13F_11 | −1.2 | −1.1 | −2 | 1.8 | 1.6 |

|   | normal TC7A_BDE_DIFF | normal TC8A_BDE_DIFF | normal TC9A_BDE_DIFF | normal TC10A_BDE_DIFF | normal TC11A | G2 T1 TC16A_BDE_DIFF | G2 Ta TC17A_BDE_DIFF | High Ta TC18A_BDE_DIFF | Low T1 TC19A_BDE_DIFF |
|---|---|---|---|---|---|---|---|---|---|
| 1 | 1 | −2.5 | −2 | 1.2 | −1.2 | 2.6 | 2.4 | 2.5 | 2.6 |
| 2 | 1 | −2.6 | −1.9 | 1.3 | −1.1 | 2.4 | 2.6 | 3.6 | 2.9 |
| 3 | 1 | −2.1 | −1.8 | 1.3 | −1.4 | 7.1 | 4.6 | 6.3 | 4.1 |
| 4 | 1 | −2 | −1.8 | −1 | −1.2 | 3.6 | 11 | 6.9 | 2.3 |
| 5 | 1 | −2.6 | −2.5 | 2.1 | 1.6 | 3 | 6.1 | 8.2 | 2.8 |
| 6 | 1 | −1.7 | −1.3 | −1.1 | −1.5 | 5 | 4.6 | 4 | 2.4 |
| 7 | 1 | −2.6 | −2.4 | 1.9 | 1.4 | 2.8 | 4.9 | 6.8 | 2.5 |
| 8 | 1 | −1.6 | −1.2 | 1.1 | −1.5 | 2.7 | 2.6 | 2.6 | 1.7 |
| 9 | 1 | −1.2 | 1.2 | −1.8 | −1.2 | 1.9 | 2.5 | 1.9 | 1.4 |
| 10 | 1 | −2.1 | −1.5 | 1.1 | −1.6 | 2.7 | 1.8 | 2.9 | −1 |
| 11 | 1 | −1.4 | −1.7 | 1.1 | −1.1 | 2.9 | 3.8 | 2.7 | 2.3 |
| 12 | 1 | −1.5 | −1.5 | 2 | 1 | 1.2 | 1.7 | 4.6 | 2.2 |
| 13 | 1 | −1.1 | −1.1 | −1.3 | 1.1 | 2.8 | 3.6 | 4.5 | 2.3 |
| 14 | 1 | −1.1 | −1.3 | 1.1 | 1.1 | 2.7 | 5 | 2.1 | 1.9 |
| 15 | 1 | −2 | −1.9 | 1.5 | 1.2 | 2.8 | 2.8 | 2.9 | 4.9 |
| 16 | 1 | −1.3 | 1.3 | 1.6 | 1.1 | 1.9 | 1.6 | 2.5 | 1.5 |
| 17 | 1 | −1.2 | 1.2 | −1.1 | 1.1 | −1.1 | −1.4 | 1.4 | −1.4 |
| 18 | 1 | −2.2 | −2.1 | 1.1 | −1.2 | 3.8 | 1.4 | 3.6 | 3.9 |
| 19 | 1 | −1.8 | −1.9 | 1.4 | 1.2 | 3.1 | 3.7 | 4.5 | 4.4 |
| 20 | 1 | −1.6 | −1.3 | −1 | −1.5 | 1.8 | 2.1 | 2.2 | 1.2 |

|   | G3 T1 TC20A_BDE_DIFF | normal TC21A_BDE_DIFF | normal TC22A_BDE_DIFF | normal TC23A_BDE_DIFF | normal TC24A_BDE_DIFF | Low T1 TC25A | G3 T1 + TIS TC28A_BDE_DIFF | High T1 TC29A_BDE_DIFF | G3 T1 TC30A_BDE_DIFF |
|---|---|---|---|---|---|---|---|---|---|
| 1 | 1.7 | −1.3 | 1 | 1.3 | −2.1 | 2.6 | 2.4 | 2.2 | 2 |
| 2 | 1.6 | −1.2 | 1 | 1.2 | −1.9 | 2.1 | 2.2 | 2 | 1.8 |
| 3 | 4.3 | −1.6 | 1 | 1.8 | −1.7 | 4 | 1.5 | 3.5 | 3.6 |
| 4 | 3.4 | −1.5 | 1 | 1.7 | −1.8 | 4.4 | −1.3 | 2 | 2.1 |
| 5 | 1.3 | 1.3 | 1 | 1.9 | −1.1 | 4.4 | −1.1 | 3.5 | 3.2 |
| 6 | 4.7 | −1.3 | 1 | 1.4 | −1.1 | 2.7 | 1.6 | 1.2 | 1.3 |
| 7 | 1.1 | −1.1 | 1 | 1.9 | −1.1 | 3.5 | 1.2 | 2.4 | 2 |
| 8 | 2 | 1.2 | 1 | 1.5 | 1.7 | 2.4 | 3.9 | 2.2 | 1.7 |
| 9 | 2.9 | 1.1 | 1 | 1.4 | 1 | 3.7 | 7 | 2 | −1.1 |
| 10 | 1.4 | −1.2 | 1 | 1.2 | −1.2 | 2.4 | −1.1 | 2 | 2.7 |
| 11 | 1.5 | −1.6 | 1 | 1.2 | −2.4 | 3.8 | −1.1 | 2.4 | 1.1 |
| 12 | 1.6 | −2.5 | 1 | 1.1 | 1 | 1.8 | −1.8 | 1 | 5.7 |
| 13 | 1.7 | 1.1 | 1 | 1.4 | −1.2 | 3.1 | −1.3 | 1.2 | 1.1 |
| 14 | 1.8 | −1.6 | 1 | 1.2 | −2 | 2.4 | 1.1 | 1.7 | 1.3 |
| 15 | 1.6 | −1.4 | 1 | 1.2 | 1.4 | 3.1 | −1.3 | 1.6 | 1.2 |
| 16 | 2.2 | −2.1 | 1 | 1.1 | −2.3 | 3.9 | −1.3 | 2.5 | 2 |
| 17 | 1.2 | −1.3 | 1 | 1.1 | 1.6 | −1.3 | 5.7 | 6.7 | 1.9 |
| 18 | −1.2 | 1.3 | 1 | 2.1 | 1.4 | 3.8 | −2.1 | −1.5 | 1.5 |
| 19 | 2.1 | −1.3 | 1 | 1.5 | 1.2 | 3.7 | −1.5 | 1.5 | −1 |
| 20 | 1.8 | −1.3 | 1 | −1.1 | −1.3 | 1.8 | 4.6 | 2.8 | 1.9 |

|   | G1/2 Ta TC31A_BDE_DIFF | G2 Ta/T1 TC32A_BDE_DIFF | G2 Ta TC33A_BDE_DIFF | INV TC34A_BDE_DIFF | normal TC35A_BDE_DIFF | normal TC36A_BDE_DIFF | normal TC37A_BDE_DIFF | normal TC38A_BDE_DIFF | Low Ta TC39A_BDE_DIFF |
|---|---|---|---|---|---|---|---|---|---|
| 1 | 2.1 | 2.3 | 2.4 | −1 | −3.9 | −1.4 | −1.8 | −1.4 | 3.2 |
| 2 | 1.8 | 2 | 1.9 | −1.2 | −4.5 | −1.6 | −2.3 | −1.6 | 2.9 |
| 3 | 4.3 | 3.2 | 2.1 | 1.1 | −3.3 | −1.2 | −1.4 | −1.3 | 3.5 |
| 4 | 1.6 | 4.8 | 2 | 3.3 | −1.4 | −1 | −1.6 | −1 | 4.1 |
| 5 | 3.7 | 5 | 2.6 | 1.8 | −4 | 1 | −1.7 | −1.3 | 3.4 |
| 6 | 4.3 | 3.7 | 2.2 | 1.1 | 1.1 | −1 | −1 | 1 | 2.3 |

TABLE 1-continued

| | | | | | | | | | |
|---|---|---|---|---|---|---|---|---|---|
| 7 | 2.4 | 3.1 | 1.7 | 1.6 | 1.2 | 1 | −1.6 | −1 | 2.4 |
| 8 | 2.5 | 2.6 | 2.7 | 2.1 | 2 | −1.3 | −1.6 | 1 | 1.4 |
| 9 | 2.5 | 1.8 | 2.5 | 1.3 | −1.3 | 1.1 | 1.2 | 1 | 1.8 |
| 10 | 13 | 1.8 | 3.8 | 3 | 1.4 | 1.1 | 1.4 | 1.1 | 3.8 |
| 11 | 2.3 | 2.4 | 1.8 | 2.5 | −1.5 | −1.2 | −1.8 | −1.1 | 2.7 |
| 12 | 3.5 | 1 | 3.9 | −1.1 | −4.1 | −1.5 | −1.9 | −1.1 | 1.1 |
| 13 | 3.1 | 1.6 | 1.8 | −1.1 | 2 | −1.2 | −1.4 | −1 | 2.3 |
| 14 | −1 | 2 | 1.9 | −1.1 | −2.3 | −1.4 | −1.6 | −1.3 | 1.6 |
| 15 | 2.3 | 6.7 | −1.3 | 1.3 | −1.3 | 1.2 | 1.3 | 1.1 | 1.9 |
| 16 | 3.7 | 2.6 | 2.5 | −2.1 | −1.2 | 1.1 | −1.2 | 1.1 | 1.3 |
| 17 | 1.8 | 1 | 1.7 | 3.5 | 1.5 | 1.3 | 1.2 | 1.1 | 1.9 |
| 18 | 5.3 | −1.9 | 3.2 | −1.8 | −1.8 | −1.2 | −1.1 | −1.1 | 2.2 |
| 19 | 2.1 | 6 | −1.5 | 1.1 | −1.3 | −1.1 | 1 | 1 | 1.6 |
| 20 | 3 | 3.1 | 3.1 | 2.5 | 2.4 | −1.1 | −1.7 | 1.2 | 1.7 |

| | G2/3 T1 TC40A_BDE_DIFF | G2 Ta TC41A_BDE_DIFF | G2 Ta TC42A_BDE_DIFF | G2 T1 TC43A_BDE_DIFF | G2 Ta TC44A_BDE_DIFF | INV TC45A_BDE_DIFF | normal TC46A_BDE_DIFF |
|---|---|---|---|---|---|---|---|
| 1 | 3.1 | 2.2 | 2.6 | 1.7 | 3.6 | 1.1 | −1 |
| 2 | 2.5 | 1.8 | 2.4 | 1.6 | 3.6 | 1.1 | −1.1 |
| 3 | −1.9 | 2.4 | 2.5 | 1.8 | 5.6 | 1.3 | −1.1 |
| 4 | 2.3 | 1.7 | 1.5 | 2.2 | 3.3 | 1.2 | 1.1 |
| 5 | 4.5 | 1.3 | 3.3 | 2.3 | 3.4 | −1.6 | −1.2 |
| 6 | 3.4 | 2 | 1.9 | 2.2 | 3.1 | 1.1 | −1 |
| 7 | 2.7 | 1.1 | 2.4 | 1.5 | 2.9 | −1.4 | 1.1 |
| 8 | 1.6 | 2.6 | 1.6 | 2 | 3 | 1.2 | −1.1 |
| 9 | 4 | 1.7 | 2.5 | 1.4 | 2.3 | 1.5 | 1.3 |
| 10 | 3.4 | 3.2 | 1.4 | 2.6 | 3.8 | 2.7 | 1.1 |
| 11 | 1.2 | 2.1 | 1.9 | 1.2 | 3.1 | 1.3 | 1.1 |
| 12 | 2.8 | 2.5 | 2 | 2.2 | 3.9 | 2.1 | 1.1 |
| 13 | 2 | 1.8 | 1.9 | 1.3 | 2.8 | 1.4 | 1 |
| 14 | 2.6 | 1.1 | 1.3 | 1.3 | 1.4 | −1.3 | 1.1 |
| 15 | 1.5 | 1.9 | 2.5 | 1.8 | 2.3 | 1.1 | −1.4 |
| 16 | 1.6 | 2 | 1.4 | 2 | 1.3 | 1.4 | 1.6 |
| 17 | 2.5 | 2.4 | 1.7 | 1.4 | 1 | 2.5 | 1 |
| 18 | 1.5 | 2.3 | 2.8 | 2.8 | 3.1 | 1.1 | −1.2 |
| 19 | 1.2 | 1.9 | 2.3 | 1.9 | 2.9 | 1.1 | −1.3 |
| 20 | 1.9 | 2.9 | 2 | 2.1 | 3.2 | 1.3 | 1 |

| | normal TC47A_BDE_DIFF | normal TC48A_BDE_DIFF | secreted |
|---|---|---|---|
| 1 | 1 | −1.1 | 3.9 |
| 2 | 1 | −1.1 | 3.8 |
| 3 | 1 | −1.2 | 3.8 |
| 4 | 1 | −1.1 | −1.8 |
| 5 | 1 | −1 | −1.2 |
| 6 | 1 | −1.1 | 1 |
| 7 | 1 | −1 | −1.4 |
| 8 | 1 | −1.3 | −2.2 |
| 9 | 1 | 1.1 | −2.6 |
| 10 | 1 | 1 | |
| 11 | 1 | −1.3 | −1.6 |
| 12 | 1 | −1.2 | −1.2 |
| 13 | 1 | −1.2 | 4.9 |
| 14 | 1 | −1.1 | −1.5 |
| 15 | 1 | −1.2 | |
| 16 | 1 | −1.1 | 3.8 |
| 17 | 1 | 1 | 1.9 |
| 18 | 1 | −1.2 | −1.7 |
| 19 | 1 | −1.1 | −1.4 |
| 20 | 1 | −1.2 | −2.2 |

TABLE 2

| | GeneDescription and clone ID | Accession | GeneID | T1 TC2A_BDE_DIFF | G2/3 T1 TC3A_BDE_DIFF | G2/3 T1 TC4A_BDE_DIFF | G2/3 T1 TC5A_BDE_DIFF | G1/2 T1 TC6A_BDE_DIFF |
|---|---|---|---|---|---|---|---|---|
| 1 | *Homo sapiens* full length insert cDNA clone ZC48G12; nt_non_genomic(identity): 03_TCC_57E11_T7.TXT.fa | gi\|3483555\|gb\|AF086210.1\|HUMZC48G12 | TCC-57E_11 | 3.3 | 2.8 | 3.2 | 1.3 | 2.3 |

TABLE 2-continued

| | | | | | | | | |
|---|---|---|---|---|---|---|---|---|
| 2 | xq01h07.x1 Soares_NHCeC_cervical_tumor *Homo sapien*; est(identity):24_TCC_96C7_M13F.TXT | gi\|7154678\|gb\|AW516596.1\|AW516596 | TCC-96C_7 | 2.8 | 4.3 | 5.8 | 5.9 | −1.4 |
| 3 | hh68c04.x1 NCI_CGAP_GU1 *Homo sapiens* cDNA clone IM; est(identity):26_TCC_13H10_M13F_B04_032.ab1.fa | gi\|7318401\|gb\|AW613215.1\|AW613215 | TCC-13H_10 | 2.2 | 1.6 | 2.1 | 1 | 1.2 |
| 4 | none:21_TCC_43E2_M13F.TXT | | TCC-43E_2 | 2.7 | 4.7 | 7.3 | 1.5 | 1.7 |
| 5 | RC3-BN0053-170200-011-e12 BN0053 *Homo sapiens* cDNA; est(identity):28_TCC_16D12_M13F_D04_041.ab1.fa | gi\|8257938\|gb\|AW997704.1\|AW997704 | TCC-16D_12 | 2.7 | 5.3 | 2.4 | 8.8 | −1.4 |
| 6 | none:08_TCC_70E7_M13F_H01_015.ab1.TXT | | TCC-70E_7 | 3.8 | 2.1 | 3.6 | 1.6 | 1.5 |
| 7 | *Homo sapiens* clone RP4-584D14, complete sequence; nt_non_genomic(identity):14_TCC_9B6_M13F_F02_026.ab1.fa | gi\|8468933\|gb\|AC005586.2\|AC005586 | TCC-9B_6 | 11 | −1 | 3.9 | 4.1 | −1.6 |
| 8 | *Homo sapiens* CG1-B1 protein (LOC51108), mRNA; nt_non_genomic(identity):11_TCC_101E11_M13F.TXT.fa | gi\|7705788\|ref\|NM_016025.1\| | TCC-101E_11 | 5.1 | 2.1 | 3.1 | 1.6 | 1.3 |
| 9 | *Homo sapiens* mRNA for KIAA0660 protein, complete; nt_non_genomic(identity):72_TCC_37E11_M13F_H09_079.ab1.fa | gi\|3327133\|dbj\|AB014560.1\|AB014560 | TCC-37E_11 | 8 | −1.5 | 3.1 | 3.1 | −1.3 |
| 10 | *H.sapiens* GaINAc-T1 gene, 3'UTR; nt_non_genomic (identity):54_TCC_30E5_M13F_F07_062.ab1.fa | gi\|2292903\|emb\|Y10343.1\|HSY10343 | TCC-30E_5 | 3.3 | 2.3 | −1.2 | 1.3 | 2 |
| 11 | none:15_TCC_71H8_M13F_G02_019.ab1.TXT | | TCC-71H_8 | 1.7 | 1.4 | −1 | 2.5 | 2 |
| 12 | *Homo sapiens* ETAA16 protein (ETAA16), mRNA; nt_non_genomic(identity):09_TCC_101C11_M13F.TXT.fa | gi\|9506580\|ref\|NM_019002.1\| | TCC-101C_11 | 6.1 | 2.2 | 3.2 | 1.9 | 1.2 |
| 13 | *Homo sapiens* cDNA FLJ10861 fis, clone NT2RP400157; nt_non_genomic(identity):24_TCC_12F3_M13F_H03_031.ab1.fa | gi\|7023162\|dbj\|AK001723.1\|AK001723 | TCC-12F_3 | 1.4 | 2 | 1.1 | −1.3 | 1.6 |
| 14 | hh75c10.x1 NCI_CGAP_GU1 *Homo sapiens* cDNA clone IM; est(identity):59_TCC_34D5_M13F_C08_065.ab1.fa | gi\|7318796\|gb\|AW613610.1\|AW613610 | TCC-34D_5 | 1.6 | 2.5 | 1.9 | 1.1 | 1.4 |
| 15 | none:15_TCC_57C3_M13F.TXT.fa | | TCC-57C_3 | 3.5 | 2.8 | 2.9 | 1.2 | 2.3 |
| 16 | yj81a11.r1 Soares breast 2NbHBs1 *Homo sapiens* cDNA; est(identity):29_TCC_17A5_M13F_E04_034.ab1.fa | gi\|843837\|gb\|R70320.1\|R70320 | TCC-17A_5 | 2.7 | 2.6 | 1.9 | 1.7 | 9.3 |
| 17 | hypothelical protein C50F7.2 - Caenorhabditis eleg; CONTIG_nr(strong):31_TCC_10E8_M13F.fa | gi\|7497781\|pir\|\|T29299 | TCC-10E_8 | 1.1 | 1.4 | 1.6 | 1.5 | −1.1 |
| 18 | none:13_TCC_71E4_M13F_E02_018.ab1.TXT | | TCC-71E_4 | 1.7 | 1.6 | 1.3 | 2.3 | 2.1 |
| 19 | *Homo sapiens* mRNA; cDNA DKFZp434L0310 (from clone; nt_non_genomic(identity):57_TCC_80C9_M13F_A08_056.ab1.TXT | gi\|6808331\|emb\|AL137591.1\|HSM802346 | TCC-80C_9 | 3.7 | 2 | 3.2 | 1.7 | 1.3 |
| 20 | none:44_TCC_70E8_M13F.TXT.fa | | TCC-70E_8 | 4.1 | 2.2 | 3.7 | 1.7 | 1.5 |

| | normal TC7A_BDE_DIFF | normal TC8A_BDE_DIFF | normal TC9A_BDE_DIFF | normal TC10A_BDE_DIFF | normal TC11A | G2 T1 TC16A_BDE_DIFF | G2 Ta TC17A_BDE_DIFF | High Ta TC18A_BDE_DIFF | Low T1 TC19A_BDE_DIFF | G3 T1 TC20A_BDE_DIFF |
|---|---|---|---|---|---|---|---|---|---|---|
| 1 | 1 | −1.3 | −1.5 | 1.2 | −1.2 | 2.2 | 2.6 | 3.7 | 1.9 | 1.5 |
| 2 | 1 | −1.3 | −1 | 2.7 | 1.2 | 4 | 7.5 | 2.2 | 2 | 1.2 |
| 3 | 1 | −1.4 | 1.1 | 1 | −1 | 1.3 | 1.2 | 1.3 | −1.1 | −1.1 |
| 4 | 1 | 2.3 | −2.3 | 2.1 | 1.7 | 1.8 | 5.1 | 6.2 | 2.5 | 1.1 |
| 5 | 1 | 2.7 | 1.3 | 1.3 | −1.2 | 3.6 | 4.4 | −1.1 | 2.3 | −1.3 |
| 6 | 1 | −1.6 | −2.1 | 1.1 | −1.1 | 3.5 | 4.8 | 2.9 | 2.6 | 2.3 |
| 7 | 1 | −1.6 | 1 | −1.2 | −1.4 | 3 | 3.7 | 1.3 | 1.2 | 1 |
| 8 | 1 | −1.5 | −1.4 | 1.1 | 1.2 | 2.8 | 7.2 | 4.4 | 2.1 | 2.1 |
| 9 | 1 | −1 | −1.2 | −1.4 | −1.6 | 1.6 | 2 | −1 | −1.3 | −1.2 |
| 10 | 1 | 1.5 | 1.1 | 1.8 | 2.1 | −1.1 | 1.7 | 1.7 | 1.2 | 1.3 |
| 11 | 1 | −1.5 | −1.2 | 1.1 | −1.3 | 2.1 | 2.6 | 3 | 1.6 | 1.1 |
| 12 | 1 | −2.3 | −1.4 | −1 | 1 | 2.6 | 6.8 | 4.2 | 1.9 | 1.9 |
| 13 | 1 | −1 | 1.1 | 2 | 1.2 | 1.2 | 1.7 | 1.5 | 1.5 | −1 |
| 14 | 1 | 1.1 | 1.1 | 1.9 | 1.4 | −1.7 | −1.2 | −1.1 | −1.5 | −1.4 |
| 15 | 1 | −1.1 | −1.6 | 1.2 | 1.2 | 1.6 | 2.6 | 2.9 | 1.7 | 1.3 |
| 16 | 1 | 1.2 | 1.5 | 1.8 | 1.6 | 1.5 | −1 | 1.4 | −1.2 | −1.1 |
| 17 | 1 | 1.3 | 1.3 | 1 | −1.1 | −1.1 | −1.7 | −1.7 | −1.2 | −1.1 |
| 18 | 1 | −1.4 | −1.3 | 1 | −1.1 | 1.8 | 2.3 | 2.7 | 1.6 | 2.4 |
| 19 | 1 | −1.5 | −1.3 | 1.1 | −1.3 | 1.1 | 1.8 | 1.9 | 2.1 | 1.8 |
| 20 | 1 | 1.3 | −1.7 | 1.1 | −1 | 2.9 | 4.3 | 2.4 | 2 | 2.3 |

TABLE 2-continued

|   | normal TC21A_ BDE_DIFF | normal TC22A_ BDE_DIFF | normal TC23A_ BDE_DIFF | normal TC24A_ BDE_DIFF | Low T1 TC25A | G3 T1 + TIS TC28A_ BDE_DIFF | High T1 TC29A_ BDE_DIFF | G3 T1 TC30A_ BDE_DIFF | G1/2 Ta TC31A_ BDE_DIFF | G2 Ta/T1 TC32A_ BDE_DIFF |
|---|---|---|---|---|---|---|---|---|---|---|
| 1 | 1 | 1 | 1.7 | -1.1 | 2.9 | 2.1 | 2 | 1.9 | 1 | 4.4 |
| 2 | 1.2 | 1 | 1.9 | 1.4 | 2 | 1.3 | -1.1 | 3.2 | 1.1 | 9.1 |
| 3 | -2 | 1 | -1 | -1 | -1.1 | 3.4 | 2.9 | 2.7 | 3.1 | 5.5 |
| 4 | -1.1 | 1 | 1.8 | -1.1 | 3.2 | -1.4 | 2.5 | 2.3 | 2.7 | 3.5 |
| 5 | -1.2 | 1 | 1.1 | 2 | 1.3 | -1 | 2.1 | 3 | 2 | 2 |
| 6 | -1.4 | 1 | 1.5 | -1.8 | 3.8 | -1.2 | 2.2 | 1.1 | 2.2 | 2.3 |
| 7 | 1.6 | 1 | 1.5 | 2.2 | 1.1 | 1.6 | 12 | 3 | 4.2 | 2.5 |
| 8 | -1.4 | 1 | 1.4 | -1.6 | 2.4 | -1.2 | 1.7 | 1.8 | 1.4 | 3.9 |
| 9 | 1.2 | 1 | 1.1 | 1.4 | -1.3 | 1 | 7.1 | 2.3 | 3.2 | 2.4 |
| 10 | 1.3 | 1 | 1.2 | 1.6 | 1.5 | 1.4 | 2.5 | 2.3 | 6.1 | 3.8 |
| 11 | 1 | 1 | 1.2 | -1.1 | 2.2 | 3.5 | 2 | 1.8 | 2.4 | 2.7 |
| 12 | -1.1 | 1 | 1.4 | -1.3 | 2.3 | -1.1 | 1.5 | 1.8 | 1.4 | 3.7 |
| 13 | 1.1 | 1 | 1.2 | 1.2 | 1.9 | 1.6 | 2.8 | 4.1 | 5.5 | 2 |
| 14 | -1.4 | 1 | -1.2 | 1.4 | -1.3 | 2.1 | 1.8 | 2.4 | 2.3 | 3.5 |
| 15 | -1 | 1 | 1.3 | -1.1 | 2.3 | 1.9 | 1.5 | 1.9 | -1.4 | 3.2 |
| 16 | 1.4 | 1 | 1.4 | 1.6 | -1.2 | 1.1 | -1 | 3 | 12 | 2.2 |
| 17 | 1.5 | 1 | -1.2 | 1.5 | -2 | 3.6 | 2.2 | 2.4 | 3.2 | 4.4 |
| 18 | -1.4 | 1 | -1.1 | -1.4 | 1.4 | 3.5 | 1.9 | 1.5 | 2.2 | 2.3 |
| 19 | -1.6 | 1 | 1 | -1.4 | 1.6 | 1.5 | 1.3 | 2.2 | 2.4 | 1.3 |
| 20 | -1.5 | 1 | 1.3 | -1.9 | 3.2 | -1.3 | 1.6 | -1.2 | 1.7 | 1.6 |

|   | G2 Ta TC33A_ BDE_DIFF | INV TC34A_ BDE_DIFF | normal TC35A_ BDE_DIFF | normal TC36A_ BDE_DIFF | normal TC37A_ BDE_DIFF | normal TC38A_ BDE_DIFF | Low Ta TC39A_ BDE_DIFF | G2/3 T1 TC40A_ BDE_DIFF | G2 Ta TC41A_ BDE_DIFF | G2 Ta TC42A_ BDE_DIFF |
|---|---|---|---|---|---|---|---|---|---|---|
| 1 | 2.5 | 2.3 | 2.3 | 1.3 | 1.9 | 1.3 | 2.3 | 1.9 | 1.9 | 2.1 |
| 2 | -1.6 | 1.5 | 1.9 | 1.2 | 1.7 | 1.1 | 3 | 3.7 | 2.4 | 2.2 |
| 3 | 3.7 | 3.2 | 2.3 | 2.5 | 1.8 | 2.9 | 2.8 | 3.7 | 3.7 | 3.3 |
| 4 | 2 | 1.4 | -3.6 | -1.2 | -2.3 | -1.6 | 2.4 | 3.2 | 1.2 | 2.1 |
| 5 | -2.2 | 1.1 | 1.2 | -1.2 | 1.3 | -1.2 | 6.8 | 1.3 | 1 | 2.3 |
| 6 | 1.7 | 2.4 | -1.6 | -1.2 | -2 | -1.1 | 2.6 | 1.1 | 1.9 | 1.9 |
| 7 | -1.5 | 9.8 | 1.1 | 1.2 | 1.2 | -1.1 | 6 | 4.3 | 1.5 | 1.3 |
| 8 | 1.8 | 3 | 1.2 | 1.1 | -1.3 | -1 | 3 | 2.1 | 1.5 | 1.4 |
| 9 | -1.2 | 6.1 | 1.2 | 1.5 | 1.2 | 1.2 | 4.7 | 4.5 | -1.1 | 1.1 |
| 10 | 1.5 | 2.1 | 1.4 | 1.6 | 1.7 | 1.4 | 2.2 | 1.3 | 2.6 | 2.2 |
| 11 | 2.4 | 1.9 | 1.8 | -1.4 | -1.9 | 1 | 1.3 | 1.6 | 2.3 | 1.6 |
| 12 | 1.7 | 2.8 | 1 | 1.1 | -1.1 | -1.1 | 3.1 | 2 | 1.5 | 1.6 |
| 13 | 2.4 | 2.2 | 3.1 | 1.9 | 1.8 | 1.6 | 2.5 | 1.6 | 1.7 | 2.1 |
| 14 | 2 | 1.9 | 1.7 | 1.8 | 1.7 | 1.6 | 3 | 2.9 | 2.6 | 2.1 |
| 15 | 2 | 2 | 1.9 | 1.3 | 1.6 | 1 | 1.7 | 1.6 | 1.4 | 2 |
| 16 | 3.4 | 1.3 | 1.5 | 1.3 | 1.9 | 1.3 | 2.6 | 1.9 | 3.1 | 1.4 |
| 17 | 3.5 | 2.2 | 3.2 | -1.1 | 1 | 1.1 | 1.6 | 2.7 | 3.1 | 2.3 |
| 18 | 2.2 | 1.8 | 1.7 | -1.3 | -1.7 | -1 | 1.4 | 1.6 | 2.1 | 1.6 |
| 19 | 1.4 | 1.6 | 1.8 | 1.3 | 2.3 | 1.2 | 3.3 | 2.8 | 2.5 | 1.9 |
| 20 | 1.2 | 1.9 | -1.7 | -1.4 | -2.1 | -1.4 | 1.9 | -1 | 1.5 | 1.3 |

|   | G2 T1 TC43A_ BDE_DIFF | G2 Ta TC44A_ BDE_DIFF | INV TC45A_ BDE_DIFF | normal TC46A_ BDE_DIFF | normal TC47A_ BDE_DIFF | normal TC48A_ BDE_DIFF | secrtd |
|---|---|---|---|---|---|---|---|
| 1 | 2.3 | 2.3 | 2.4 | 1 | 1 | -1.1 | -1.8 |
| 2 | 4.6 | 3.5 | 1.2 | -1.2 | 1 | -1.1 |  |
| 3 | 3.4 | 3.6 | 3.4 | 1.7 | 1 | 3.6 | 1.1 |
| 4 | 1.9 | 3.2 | -1.8 | -1.4 | 1 | -1.1 | -1.2 |
| 5 | 5 | 2 | 1.1 | -1.2 | 1 | 1.1 |  |
| 6 | 1.2 | 3.2 | 1.3 | 1 | 1 | -1.3 | -1.6 |
| 7 | 7 | 11 | 1.3 | -1 | 1 | 1.1 | 1.3 |
| 8 | 1.7 | 3.1 | 1.2 | -1.1 | 1 | -1.2 | -1.9 |
| 9 | 4.7 | 6.7 | 1.1 | 1.1 | 1 | -1 | 1.9 |
| 10 | 2.7 | 2 | 1.7 | 1 | 1 | 1.1 | -2.2 |
| 11 | 1.9 | 2.8 | 1.2 | -1 | 1 | -1.2 | -2.2 |
| 12 | 1.8 | 2.5 | 1.2 | -1.2 | 1 | -1.3 | -1.6 |
| 13 | 2 | 2.1 | 2 | 1 | 1 | 1.1 | -1.2 |
| 14 | 2.4 | 2.8 | 1.5 | 1.1 | 1 | 1.4 |  |
| 15 | 1.6 | 2 | 2 | -1.1 | 1 | -1.3 | -1.9 |
| 16 | 2.6 | 2.8 | 1.3 | 1 | 1 | -1 |  |
| 17 | 1.6 | 1.4 | 2 | 1 | 1 | 1.1 | 3.6 |
| 18 | 1.8 | 2.9 | 1.2 | -1.1 | 1 | -1.2 | -2.3 |
| 19 | 1.4 | 2.3 | 1.6 | -1.1 | 1 | -1.5 |  |
| 20 | 1 | 2.6 | 1.3 | -1.1 | 1 | -1.3 | -1.8 |

TABLE III

SEQ ID NO. 1
>40_TCC_13F11_M13F.fa TIME: Sun Sep 10 11:42:06 2000
trimming information: raw_sequence:582 (high quality:29-320)
sequence:97-252 [length:156]
TCCGTCTCATTGAGGGTCCTGAGGAAGTTGATCTCATCATTCAGGGCATC

CACCTTGGCCTCCAGCTCCACCTTGCTCATGTAGGCAGCATCCACATCCT

TCTTCAGCACCACAAACTCATTCTCAGCAGCTGTGCGGCGGTTAATTTCA

TCTTCG

SEQ ID NO. 2
>04_TCC_94G3_M13F.TXT.fa ,constant: 15, poly A: yes
AAGGCTTATTCCATCCGGACCGCATCCGCCAGTCGCAGGAGTGCCCGCGACTGAGCCGCC

TCCCACCACTCCACTCCTCCAGCCACCACCCACAATCACAAGAAGATTCCCACCCCTGCC

TCCCATGCCTGGTCCCAAGACAGTGAGACAGTCTGGAAAGTGATGTCAGAATAGCTTCCA

ATAAAGCAGCCTCATTCTGAGGCCTGAGTGAAAAAAAAA

SEQ ID NO. 3
>20_TCC_60H4_M13F.TXT.fa ,constant: -1, poly A: no
CANTATATAACNAATTGGAGCTCAATNGCNCGCGGNCGCGTGTCTTCTGGGTAGAGGGAT

GNGAAGGAAGGGACCCTTACCCCCGGCTCTTCTCCTGACCTGCCAATAAAAATTTATGGT

CCAAGGNAAAANA

SEQ ID NO. 4
>26_TCC_44C1_M13F.TXT.fa ,constant: -1, poly A: no
ACTCATTGAACTTGAGCTCCGANTCCTGATTCNCATCNAAGCTCTNNATCTGCTCATCAN

GAGANCCCACATCCTTGAGCAGATGGNGCANCTGCTGNTTAACCANCTCTNNGAACTCGN

AGANNNTAAGGCTATCCTTCCGGNCCTCCTGCCTTGCAAAGGTGAAGAAAGTGGTGNNCA

CNGTCNCAATGGANTCCTCTAGCTCTGTCAGTGGTTCTGCTGCNATTATGGAACCTGAGG

CCAAAGCTGATGTCCTCAAGGGGCTAGCTGACCTTTGTCAGGGCTGACCTCTCCTCAGCG

GCAGCAGGGCAGAGTGCTGAACCCAGGAACCCACAGATCCTCCCCGNTCCTGTCTCCCGG

TGACAAGGGTCCTGGAACGGGGCGTCTCTGACTCCCTGCTCCAGGACGGGTTTAGT

SEQ ID NO. 5
>29_TCC_48G1_M13F.TXT.fa ,constant: -1, poly A: no
ACTTTGAGAAGGCAGGACTCAAATGATGCCCTGGAGATGTCACAGATTCCTGGCAGAGCC

ATGGTCCCAGGCTTCCCAAAAGTGTTTGTTGGCAATTATTCCCCTAGGCTGAGCCTGCTC

ATGT

SEQ ID NO. 6
>31_TCC_65B9_M13F.TXT.fa ,constant: -1, poly A: yes
GACTAGAACCCACCCCCTTNCCTTCCAGCCTTTCTGTCATCATCTCCACAGNCCANCCAT

CCCCTGAGCACACTAACCATGTCATGCAGGCCCCACCTGCCAATAGTAATAAAGCAATGT

CACTTTGTTAAAACATGAAAAAAAAA

SEQ ID NO. 7
>47_TCC_91B11._M13F.TXT.fa ,constant: -1, poly A: yes
CTAGTATACACTCCNCATAGNATACGTTGCAGCTCAATTGCGCGCGGNCGCGGACGACGA

CCTGCGAGGGTGTCTTCTGGGTAGAGGGATGGGAAGGAAGGGACCCTTACCCCCGGCTCT

TCTCCTGACCTGCCAATAAAAATTTATGGTCCAAGGAAAAAAAAA

SEQ ID NO. 8
>10_TCC_53H11_T3
TTTTTTNNATNTTATTTTGGGTATTGGTGTTNTTTCTTTTTTCCTCTTNCCTTCTTAACT

CAAGACTTGTAGTGTTGTAAACCTGCCTCACAAAATACATGGTAATAACTTNTCTTTAAA

AAAANAAAAAAGACAGNCTTNACACCATTTCTAATNGNANNACTATTTTTGGGCAATGTT

ATGCACCACTTCAATTTCCCCATTGTGACCCCTATCACTTCATTTGATATCCCTTTTNGA

TABLE III-continued

```
CCCANCCATCTCCTTCATATATGGGCATGTCCATAGATTGACAAAGAAAGTTTACACTTT

NGAATAAAGATGCAAAGTATGCAAAAACATTAATACTGATGCNAAAAAAANTANAAAAA

SEQ ID NO. 9
>07_TCC_57B3_M13F.TXT ,constant: -1, poly A: yes
GGTACCGACGGACCTGCGGAGACTCCTGCCCTGTTGTGTATAGATGCAAGATATTTATAT

ATATTTTTGGTTGCAATATTAAATACAGACACTAAGTTATAGTATATCTGGCAAGCCAAC

TTGTAAATCACCACCTCACTCCTGTACTTACCTAAACAGATATAAATGGCTGGTTTTTAA

GAAAAAAAAA

SEQ ID NO. 10
>11_TCC_25F2_M13F.TXT ,constant: -1, poly A: no
ACCCTGGGAGAGAAGTTTGAAGAAACCACAGCTGATGGCAGAAAAACTCAGACTGCTGCA

ACTTTACAGATGGTGCATTGNGTCAGCATAGGAGTGAGATGGGGAAGGAAAGCACANTAA

CAAGAAAATTGANAGATGNTAAATTAGTGNTGGAGTGTGTCATGAACAATGCACCTGT
SEQ ID NO. 11
>25_TCC_50G5_M13F.TXT ,constant: 17, poly A: yes
TAGTGTGGAAGCATAGTGAACACACTGATTAGGTTATGGTTTAATGTTACAACAACTATT

TTTTAAGAAAAACATGTTTTAGAAATTTGGTTTCAAGTGACATGTGTGAAAACAATATCG

ATACTACCATAGTGAGCCATGATTTTCTAAAAAAAAA

SEQ ID NO. 12
>26_TCC_50G6_M13F.TXT ,constant: 17, poly A: yes
TAGTGTGGAAGCATAGTGAACACACTGATTAGGTTATGGTTTAATGTTACAACAACTATT

TTTTAAGAAAAACAAGTTTTAGAAATTTGGTTCAAGTGACATGTGTGAAAACAATATTGT

ATACTACCATAGTGAGCCATGATTTTCTAAAAAAAAA

SEQ ID NO. 13
>26_TCC_75E3_M13F_B04_032.abl.TXT ,constant: 16, poly A: yes
AAAGAGGGCGGCAGGGGCCTGGAGATCCTCCTGCAGACCACGCCCGTCCTGCCTGTGGCG

CCGTCTCCAGGGGCTGCTTCCTCCTGGAAATTGACGAGGGGTGTCTTGGGCAGAGCTGGC

TCTGAGCCGCCCTCCATCCAAGGCCAGGTTCTCCGTTAGCTCCTGTGGCCCCACCCTGGG

CCCTGGGCTGGAATCAGGAATATTTTCCAAAGAGTGATAGTCTTTTTGCTTTTTGGCAAA

ACTCTACTTAATCCAATGGGTTTTTCTCTGTACAGTAGATTTTCCAAATGTAATAAACTT

TAATATAAAGTAAAAAAAAA

SEQ ID NO. 14
>30_TCC_76B3_M13F_F04_042.abl.TXT ,constant: 16, poly A: yes
AAAGTCATCCTCCGTCTACCAGAGCGTGCACTTGTGATCCTAAAATAAGCTTCATCTCCG

GGCTGTGCCCCTTGGGGTGGAAGGGGCAGGATTCTGCAGCTGCTTTTGCATTTCTCTTCC

TAAATTTCATTGTGTTGATTTCTTTCCTTCCCAATAGGTGATCTTAATTACTTTCAGAAT

ATTTTCAAAATAGATATATTTTTAAAATCCTTAAAAAAAAA

SEQ ID NO. 15
>38_TCC_56E11_M13F.TXT ,constant: -1, poly A: yes
CTCTCCAGTTTGCACCTGTCCCCACCCTCCACTCAGCTGTCCTGCAGCAAACACTCCACC

CTCCACCTTCCATTTTCCCCCACTACTGCAGCACCTCCAGGCCTGTTGCTATAGAGCCTA

CCTGATGTCAATAAACAACAGCTGAAGCAAAAAAAAA

SEQ ID NO. 16
>46_TCC_78B11_M13F_F06_058.abl.TXT ,constant: 16, poly A: yes
AGGAAAGGTGNGNGCTGGAAGCACTGAACCTACCTCATCCTCCTGGTGGGTGTGGCTACC

CTCGCCACCCCAAATTCCATGTCATTAAAGAACAGCTAAATTCAAAAAAAAA

SEQ ID NO. 17
>53_TCC_79G2_M13F_E07_054.abl.TXT ,constant: 16, poly A: no
TGTCCGTCTTCACCCATCCCCAAGCCTACTAGAGCAAGAAACCAGTTGTAATATAAAATG
```

TABLE III-continued

CACTGCCCTACTGTTGGTATGACTACCGTTACCTACTGTTGTCATTGTTATTACAGCTAT

GGCCACTATTATTAAAGAGCTGTGTAACATCAAAAAAA

SEQ ID NO. 18
>82_TCC_89G3_M13F_B11_092.abl.TXT ,constant: 16, poly A: yes
CAGGAGACCATCCGCGTCACCAAGCCCTGCACCCCCAAGACCAAAGCAAAGGCCAAAGCC

AAGAAAGGGAAGGGAAAGGACTAGACGCCAAGCCTGGATGCCAAGGAGCCCCTGGTGTCA

CATGGGGCCTGGCCCACGCCCTCCCTCTCCCAGGCCCGAGATGTGACCCACCAGTGCCTT

CTGTCTGCTCGTTAGCTTTAATCAATCATGCCCTGCCTTGTCCCTCTCACTCCCCAGCCC

CACCCCTAAGTGCCCAAAGTGGGGAGGGACAAGGGATTCTGGGAAGCTTGAGCCTCCCCC

AAAGCAATGTGAGTCCCAGAGCCCGCTTTTGTTCTTCCCCACAATTCCATTACTAAGAAA

CACATCAAATAAACTGACTTTTTCCCCCCAAAAAAAAA

SEQ ID NO. 19
>35_TCC_21D6_M13F_C05_037.abl.fa TIME: Wed Aug 9 12:48:31 2000 trimming
information: raw_sequence:889 (high quality:34-340) sequence:95-456
[length: 362]
CTTTGACGTGGAGAGGAACTCCTGCAATAACTTCATCTATGGAGGCTGCC

GGGGCAATAAGAACAGCTACCGCTCTGAGGAGGCCTGCATCCTCCGCTGC

TTCCGCCAGCAGGAGAATCCTCCCCTGCCCCTTGGCTCAAAGGTGGTGCT

TCTGGCGGGGCTGTTCGTGATGGTGTTGATCCTCTTCCTGGGAGCCTCCA

TGGTCTACCTGATCCGGGTGGCACGGAGGAACCAGGAGCGTGCCCTGCGC

ACCGTCTGGAGCTCCGNAGATGACAAGGAGCAGCTGGTGAAGAACACATA

TGTCCTGTGACCGCCCTGTCGCCAAGAGGACTGGNGAAAGGGAGGGGAGA

CTATGTGTGAGC

SEQ ID NO. 20
>46_TCC_27H5_M13F_F06_058.abl.fa TIME: Wed Aug 9 12:48:35 2000 trimming
information: raw_sequence:892 (high quality:169-406) sequence:170-287
[length: 118]
AAAAAGAGTAAAACACTTTCAGTTTCTCCCCTTTAGCCCCTAAAACAACA

TCTTACAGTCTGGATCTGGATCTACCTATACAGTCCTACATTAGCTTCTA

AAATATTTGTCAGGAGGG

TABLE IV

SEQ ID NO.21
>31_TCC_10E8_M13F.fa TIME: Sun Sep 10 11:42:01 2000 trimming
information: raw sequence:549 (high quality:25-3 13) sequence:98-313
[length: 216]
CCCAAATGGAATGTTGCCCCCTTAAACACCATTTTCCCTCCAGGACCACC

TTGGTTTCTAGGCACTGTGGTTCTTGGCAGGGGCTGTCTTAGGTAAAAGG

GTAGTTGTGGAGCTACAGTCTGAAGAACATAGCTTGGGCTCAAGTTCAAA

TGAGCCATCTTTTTCCTTTGCGTTTTTCTTGACTGAAGGTGAGATGTTAT

TTGTGGCATGTGAACT

SEQ ID NO. 22
>09_TCC_101C11_M13F.TXT.fa ,constant: 16, poly A: yes
ACAAAGACTGCTGATAACTATCTGTGATTGATAGGAAATTTTTTTTCTTGATTTCTCTGT

GAGAAATGTAATGCTGACTTTTATAAAGCCTGGACTTCTACTTTATTTAATAAATCAATG

TTTGCAATGGTAAAAAAAAA

SEQ ID NO.23

TABLE IV-continued

>11_TCC_101E11_M13F.TXT.fa ,constant: 15, poly A: yes
GCAATAAAGCTGTCCATTCAATTCCAAATACTGGTTTTAAGNGTATAGCCACTGATATTC

TTTCATGTNTAGAAATTCTTTCTGTTATTATTCAAGAAAATGTTTTTAATCATGCTAATA

AACTTTTTTGGAGATGAAAAAAAAA

SEQ ID NO.24
>15_TCC_57C3_M13F.TXT.fa ,constant: -1, poly A: no
GGNACCACGTACCTGCTGAATGTNTCNNCGNNATGNCGNCAGGCCATGCTGTTGCTGATN

TANTACTNTGAAAATANGGATATCATGATGGGAATGCATGTCATGAGGTCCAGANTCGTT

CTACTGTCNATAANCTGTNTACTNGCGTTGANAANAAANGATGTCAAAGNCCCCCCGTAA

AAANGTA

SEQ ID NO.25
>44_TCC_70E8_M13F.TXT.fa ,constant: 15, poly A: yes
GTCCCAGTCTTCACCAGGTGTCTCTCCTCTTTTACTCAGGAGGACTTTCCCAGGAAAACC

ATGCCACTAGCAAAAAAAAA

SEQ ID NO.26
>03_TCC_57E11_T7.TXT.fa ,constant: 16, poly A: yes
TGAGTGTCTTCAGGCCAACCTGGTGGAAATGTTGTTCTCTGAAGATTAAGATTTTAGGAT

GGCAATCATGTCTTGATGTCCTGATTTGTTCTAGTATCAATAAACTGTATACTTGCTTTG

AATTCATGTTAGCAATAAATGATGTTAAAAAAAAA

SEQ ID NO.27
>08_TCC_70E7_M13F_H01_015.abl.TXT ,constant: -1, poly A: no
GGATCGACGACCTGCTTCCCAGANGCGNNCNNGAGGNCCNCTTGTTNNNGNCNNGNANAC

NNACCCANTTNANTTNNAGCCTTTNTGNAATAAATATACACAGGCCACCCATGCCNTGAG

CACACTAACCACNTGATGCAGGCCCCACCTTGCCAATAGTAATAAAGCANTGGGACGTTT

TTTA

SEQ ID NO. 28
>13_TCC_71E4_M13F_E02_018.abl.TXT ,constant: -1, poly A: no
GGGCCAAAGCCCGNGCATCCAANCCCANGCAAGGNACAAANGANCNNGGAGAGGANNACC

CAAGCANNTNNCAACCATCAAATGGAGGGCANGCCCGGGG

SEQ ID NO.29
>15_TCC_71H8_M13F_G02_019.abl.TXT ,constant: -1, poly A: no
GGGCCAAAGCCCGNGCATCCAANCCCANCGCANGGNANAAANGANGANGGANAGNGATNAC

CCANGCCTNTATTAACCATCAANTGGGANGGCAAGCCCGGGGCATNTATTGATT

SEQ ID NO. 30
>21_TCC_43E2_M13F.TXT ,constant: -1, poly A: no
AGGACCCCTGAANACNACACAGATCTGTGNGAAACAANGGNACNTAGCGTCCCNAAAGTG

CCNGGTTNNNGTANNCNNAGNGNGNGACCNGNGCNCATNT

SEQ ID NO.31
>24_TCC_96C7_M13F.TXT ,canstant: 16, poly A: yes
ATCCAGAGACCATCAATCCTGCTAGAGTGCAGGGTGGCAAGCACCCAAGGGTGGCTGACC

AAGACTGCAGAGTCTCCTCCATCTTCAGGTCCATTCAGCCTCCTGGCATTTAACTACCAG

CATCCAGTGGTCCCCAAGGAATCCCTTCCTAGCCTCCTGACATGAGTCTGCTGGAAAGAG

CATCCAAACAAACAAGTAATAAATAAATAAATAAACTCAAAAAAAAA

SEQ ID NO. 32
>57_TCC_80C9_M13F_A08_56.abl.TXT ,constant: 17, poly A: yes
CTGCAGGAGTCAGCGTTCAATCTTGACCTTGAAGATGGGAAGGATGTTCTTTTTACGTAC

CAATTCTTTTGTCTTTTGATATTAAAAAGAAGTACATGTTCATTGTAGAGAATTTGGAAA

CTGTAGAAGAGAATCAAGAAGAAAAATAAAAATCAGCTGTTGTAATCACCTAGCAAAAAA

AAA

TABLE IV-continued

SEQ ID NO. 33
>14_TCC_9B6_M13F_F02_026.abl.fa TIME: Wed Aug 9 12:48:25 2000 trimming
information: raw sequence: 871 (high quality:73-413) sequence:98-394
[length:297]
CACGCATATGGGGCCAGTTCCACATATTTGGCAACCAGACCAGCATCCAG

GACAACACAAAGTATGTTGTTTGTTGTTAGAGGGCTTGGGACATTTCACT

CTTTGCCAGCCTCAGCTTAATCCAGGAGACAAAGATTATTTTCCTTATTA

TCTCTTCTGCATAGGATCTGCAATCAGAACTATTGAACTTCTCCATTCAG

ACCGCCACTCACACCTATGGGAAAAGGGTAATGTATCATCGGCTTAGCAA

CAGGGAATACTATTCGTATGATGGAAAATGGGGACAAAGGCTTTGG

SEQ ID NO. 34
>24_TCC_12F3_M13F_H03_031.abl.fa TIME: Wed Aug 9 12:48:28 2000 trimming
information: raw_sequence:842 (high quality:82-340) sequence:98-476
[length:379]
CTATGAATAGCTTCTTGCTTTATGACTTTAGGATTAACTTGTAAAAAACA

TATCCTGAACTAAGATATGCAAAATACTCATTTTCAAGTTATGGAAATGT

GTTTGTGGCATATAGGACTGTGGGGTCTGTGTGTGTAGTGAGAGTGTGTA

TCCACTATTATAACTGGAATTTAATTTACATTCATAAACTACTATATTTC

CCATCTTGCAAATCATTTTATGTCTCATCTGTTTTTCCTTTCGGNTATAT

CTTTGGNTTTGAATACCAACATTTAAAATGATGGNATTTTATCTTTTAAA

CTTAAAAATTATTTAATACAGCTATATGGACCTTATAAAATTGATTTCTT

ATTTATTATTAGACATTACTACTAAAAGG

SEQ ID NO. 35
>26_TCC_13H10_M13F_B04_032.abl.fa TIME: Wed Aug 9 12:48:29 2000 trimming
information: raw_sequence:874 (high quality:67-356) sequence:99-261
[length: 163]
CTAACCCACGATTCTGAGCCCTGAGTATGCCTGGACATTGATGCTAACAT

GACCATGCTTGGGATGTCTCTAGCTGGTCTGGGGATAGCTGGAGCACTTA

CTCAGGTGGCTGGTGAAATGACACCTACGAAGGAATGAGTGCTATAGAGA

GGAGAGAGGAGTG

SEQ ID NO. 36
>28_TCC_16D12_M13F_D04_041.abl.fa TIME: Wed Aug 9 12:48:29 2000 trimming
information: raw_sequence:866 (high quality:71-41 1) sequence:95-602
[length:508]
CAGCTGATGTCATGTGGTGCTGAGAAGAAAGCAGATCACACTTCATCACA

GAAAGAATGCCTTGTGATTATCTTCTCCACATCTGAAATTCCTTTTGACA

CCTGCATTGGGCCGACTGCCATTCCCATGACTGCTGCACCTGCGTTTTTA

GAGAATGCCTCATAACCCACTGATTCTCATTCACAGAGAATGGGAATACG

GAATGAAGAAAGATTCCAGCAGCTTATAGAAGGATAGCAATATTTTGGGA

CAGGGAAAATCCTGTCATACCTCACCTCTTCCTCAGGAGGAGTTCTGAGC

TGGTCCTGCTTTTCATAGNTGTTTCTTTTCTTCCACTTAAGAACTCATAG

ATTTTTCTTACTGTCCTAAGGAACTGGTTACCTCTGAGGTATCTCCTCAA

TGAATACTGTTTTCAAGGCTGAAATAGTTCATTATGTTAATAACCTTCTT

TATGTTCTCAGGGAAATGCTTAGGTGGTGTCACAAAAAGGGCCTTTTCTT

TNCTTTNC

SEQ ID NO. 37
>29_TCC_17A5_M13F_E04_034.abl.fa TIME: Wed Aug 9 12:48:30 2000 trimming
information: raw_sequence:861 (high quality:83-477) sequence:99-187
[length:89]
CTTCAAAAAGTGTATTGTCAAACATACCTAACTTTCTTGCAATAAATGCA TABLE IV-continued

AAAGAAACTGGAACTTGACAATTATAAATAGTAATAGTG

SEQ ID NO. 38
>54_TCC_30E5_M13F_F07_062.abl.fa TIME: Wed Aug 9 12:48:37 2000 trimming
information: raw_sequence:836 (high quality:65-394) sequence:90-235
[length: 146]
CAATTTGTTATAGTATAGTATCAAATTTCTATATAGATTTTATACCTCAG

TGGGGAAAAATAACTGATTCCAATGACATTCATTTTGTTTTCATCTGTGA

TAGTCATGGATGCTTTTATTTTCCTTGGGGTGCTGAAAATTGAGCTG

SEQ ID NO. 39
>59_TCC_34D5_M13F_C08_065.abl.fa TIME: Wed Aug 9 12:48:39 2000 trimming
information: raw_sequence:875 (high quality:63-434) sequence:96-244
[length: 149]
CCTGCCAAAATCCTACCACAGGATAACATTACAAGCAAAAAATTTACATG

TTCCAAAGTCTACCACACTCAAGAAGTTACTAAGAACTCTTGCAGAATAA

AAGTCACCATTTTAGAAATGCAAACCCACTTCCAACCTTTGCACAGTCC

SEQ ID NO.40
>72_TCC_37E11_M13F_H09_079.abl.fa TIME: Wed Aug 9 12:48:43 2000 trimming
information: raw_sequence:899 (high quality:35-432) sequence:97-444
[length:348]
CATTTTTAGTGACATTTTAAAAGCAGTCAGATTCTATAAATGGCAAGTAA

GCCTGAAGTGAGGATACTGCAATTTTCGGAGAAAAGAACAGCAGCTCTTT

AAGTGTTTGCATTTTCTATTTGGGGGGCAGGGAACTGTCATTCATTTTGC

ACAATTCTTGAACTGATGTCAGCACCCGAGTGGCTCCTGAATTTAAGTCT

GGGACGACATCTTTTATTTTTACATGAATCTTTAAACAATTCTGTGAGCA

AAGTTTGTAGCTGCTGGATTATTGTCTGTCTTTATAGCAAGTTCCAGTAA

ACCACAAGTATGGCAAAGCTTATCCAATTTTATGCTTGNAGCAGTCAG

TABLE 5

Subset of 22 genes identified as potential TCC markers

| Gene ID | GENE DESCRIPTION | 2$^{nd}$ary Gene Description | Accession Number | A |
|---|---|---|---|---|
| TCC-75E3 | Sequence 202 from Patent WO9947669: nt_non_genomic(identity):contig_TCC_75E3_RF.fa | *H. sapiens* syncecan-1 gene (exons 2–5) | gi\|10042244\|emo\|AX017423.1\|AX017423 | x |
| TCC-71E4 | Sequence 102 from Patent WO9953040: nt_non_genomic(identity):contig_TCC_71E4_RF.fa | *Homo sapiens* mRNA for hepatocyte growth factor activator inhibitor type 2. complete cds | gi\|10041170\|emo\|AX014903.1\|AX014903 | x |
| TCC-94G3 | Human mRNA fragment for mesotheilial type II kerat; nt_non_genomic(identity):contig_TCC_94G3_RF.fa | | gi\|34067\|emo\|X03212.1\|HSKER7R | x |
| TCC-70E7 | none:17_TCC_70E7_1_M13F.fa none:17_TCC_70E7_1_M13R.fa | | | x |
| TCC-21G7 | *Homo sapiens* clone PP722 unknown mRNA; CONTIG_nt_non_genomic(identity): contig_TCC_21G7_RF.fa | | gi\|10441985\|gb\|AF218028.1\|AF21802B | |
| TCC-93G5 | *Homo sapiens* cystatin B (CSTB) gene, promoter reg; nt_non_genomic(identity):contig_TCC_93G5_RF.fa | | gi\|7263011\|gb\|AF208234.1\|AF208234 | x |
| TCC-36B5 | Sequence 5 from Patent WO9954447; nt_non_genomic(identity):contig_TCC_36B5_RF.fa | *Homo sapiens* hypothetical protein (LOC51323), mRNA | gi\|10040588\|emb\|AX014141.1\|AX014141 | |
| TCC-54C11 | *Homo sapiens* actin, gamma 1 (ACTG1) mRNA; nt_non_genomic(identity):contig_TCC_54C11_RF.fa | | gi\|4501886\|ref\|NM_001614.1\| | |
| TCC-34A5 | *Homo sapiens* S100 calcium-binding protein P (S100P; nt_non_genomic(identity):contig_TCC_34A5_RF.fa | | gi\|5174662\|ref\|NM_005980.1\| | x |
| TCC-70E8 | none:contig_TCC_70EB_RF.fa | | | x |
| TCC-78B11 | Sequence 56 from Patent WO995453; nt_non_genomic(identity):contig_TCC_78B11_RF.fa | Human growth factor-inducible 2A9 gene, complete cds | | |
| TCC-101E11 | *Homo sapiens* CGI-81 protein (LOC51108), mRNA; nt_non_genomic(identity):contig_TCC_101E11_RF.fa | | gi\|7705788\|ref\|NM_016025.1\| | x |

TABLE 5-continued

Subset of 22 genes identified as potential TCC markers

| Gene ID | GENE DESCRIPTION | 2<sup>nd</sup>ary Gene Description | Accession Number | A |
|---|---|---|---|---|
| TCC-102C5 | MR1-CT0058-021199-001-c10 CT0058 *Homo sapiens* cDNA; est(identity):contig_TCC_102C5_RF.fa | | gi|6879340|gb|AW374686.1|AW374686 | |
| TCC-58A3 | *Homo sapiens* keratin 17 (KRT17) mRNA; nt_non_genomic(identity):contig_TCC_58A3_RF.fa | | gi|30378|emb|Z19574.1|HSCYTOK17 | |
| TCC-57B3 | *Homo sapiens* solute carrier family 2 (facilitated; nt_non_genomic(identity):contig_TCC_57B3_RF.fa | | gi|5730050|ref|NM_006516.1| | x |
| TCC-42G5 | *Homo sapiens* caspase 4, apoptosis-related cystein; nt_non_genomic(identity):contig_TCC_42G5_RF.fa | | gi|4502576|ref|NM_001225.1| | |
| TCC-99G12 | *Homo sapiens* keratin 8 (KRT8) mRNA; nt_non_genomic(identity):contig_TCC_99G12_RF.fa | | gi|4504918|ref|NM_002273.1| | |
| TCC-92D7 | *Homo sapiens* hypothetical protein PRO2987 (PRO298); nt_non_genomic(identity):contig_TCC_92D7_RF.fa | | gi|8924228|ref|NM_018636.1| | |
| TCC-89G3 | Sequence 82 from Patent WO9951727; nt_non_genomic(identity):contig_TCC_89G3_RF.fa | *Homo sapiens* midkine (neurite growth-promoting factor 2) (MDK) mRNA | gi|10041391|emb|AX015411.1|AX015411 | x |
| TCC-56E11 | *Homo sapiens* Opa-interacting protein OIP3 mRNA, p: nt_non_genomic(identity):contig_TCC_56E11_RF.fa | | gi|2815605|gb|AF025439.1|AF025439 | |
| TCC-25F2 | Sequence 89 from Patent WO9953040; nt_non_genomic(identity):contig_TCC_25F2_RF.fa | *Homo sapiens* fatty acid binding protein 5 (psoriasis-associated) (FABP5), mRNA | gi|10041157|amb|AX014890.1|AX014890 | x |
| TCC-44C1 | *Homo sapiens* S100 calcium-binding protein A13 (S10: nt_non_genomic(identity):contig_TCC_44C1_RF.fa | | gi|5174658|ref|NM_005979.1| | x |

Notes to Table 5
1) In column A, "x" indicates that the sequence also appears in Table 1 or 2.
2) Table 5 includes known genes whose function in bladder cancer was heretofore unknown and which were now found to upregulated in bladder cancer (identified by Accession Number) and also includes sequences of novel genes which have no identity to known proteins or genes in the gene databases

TABLE 6

Polynucleotides corresponding to the Genes described in Table 5

SEQ ID NO. 41
>17_TCC_70E7_1_M13F.fa
GGTAGACGTACCTGCGTCCCAGACTTGACCAGGTGGATCTCCTGTTTTAC

TCACGAGGACTTTCCCAGGAAAACCATGCCACTAGCAAAATAATATAAAC

AAAGGA

SEQ ID NO. 42
>17_TCC_70E7_1_MI3R.fa
TTTTTTTTTTTTTTTTGGCTAGAGGCATGGATATCCTGGGAAAGCTCTCC

TGAGTAAAAGACGAGAGACACCTGGTGAAGACTGGAACGCATGTACGTCT

ACC

SEQ ID NO. 43
>contig_TCC_101E11_RF.fa
GGTCGACGTACCTGCGCAATAAAGCTGTCCATTCAATTCCAAATACTGGT

TTTAAGGTATAGCCACTGATATTCTTTCATGTTTAGAAATTCTTTCTGTT

ATTATTCAAGAAAATGTTTTTAATCATGCTAATAAACTTTTTTGGAGATG

AAAAAAAAAAAAAAAAAA

SEQ ID NO. 44
>contig_TCC_102C5_RF.fa
GCTGGTTGGGGGAATTGGAGGCTTCTAGGAGGTGGCACGGTGCACGCCAA

GATGGCTGTGTCCACAGAGGAGCTGGAGGCCACGGTTCAGGAAGTCCTGG

GGAGACTGAAGAGCCACCAGTTTTTCCAGTCCACATGGGACACTGTTGCC

TTCATTGTTTTCCTCACCTTCATGGGCACCGTGCTGCTCCTGCTGCTGCT

GGTCGTCGCCCACTGCTGCTGCTGCAGCTCCCCCGGGCCCCGCAGGGAAA

GCCCCAGGAAGGAAAGACCCAAGGGAGTGGATAACTTGGCCCTGGAACCC

TGACCCTGTGTCTCCTGCCCGGTGGCAGTAACAAAGCCTTCTGTCTGCCC

AGAAAAAAAAAAAAAAAAA

SEQ ID NO. 45
>contig_TCC_21G7_RF.fa
CTAAATCTAGGTATTCTGGCTGAGTGTATCTGGGTGGGCCAGCTAAAAAT

AAACCTCATTGAACTCCAGCCCCAACCCAGAGAAACATCCAGAAGAGCCT

TGAATTAGTGATCCAAAACCCAGGGGGAAAGGCGACATTCTCACCCCCAG

CACCCCCTTCACCTCACCTCAACTCCTACTCTCTCGGTCTATAATCACTG

CTCTCTCTCTCCCCAACACCACTATTGAACAGGAGCCCTTGTCACCAGGT

CCAAGCAATTCCCTAAGGTATCACAAACAATGGTGGATGCAATTTTACCT

TACTCAGTAACCACGAGGCTCACATCCCTAATTTCAGACTCTACCAGCTC

TCAGGTGCCCTCCCAAGGGGCTGCCTGCATGAAGATGCCTTGGAAGTAGC

CCCTTTCACAATCACAGGAATTAACCCCCTGGTGTTGGAGGGGCCTCACT

TTAAGCAATCCCAGTAGTAAACATTGGATAAATCTAAAGGCTTTCTTTAA

TTTTTTTTTTCTCTTCGTAAAGGATTCAAAGCAGGCACAGTGGTG

SEQ ID NO. 46
>contig_TCC_25F2_RF.fa
CCCTGGGAGAGAAGTTTGAAGAAACCACAGCTGATGGCAGAAAAACTCAG TABLE 6-continued Polynucleotides corresponding to the Genes described in Table 5

ACTGTCTGCAACTTTACAGATGGTGCATTGGTTCAGCATCAGGAGTGGGA

TGGGAAGGAAAGCACAATAACAAGAAAATTGAAAGATGGGAAATTAGTGG

TGGAGTGTGTCATGAACAATGTCACCTG

SEQ ID NO. 47
>contig_TCC_34A5_RF.fa
CATGAGCAGGCTCAGCCTAGGGGAATAATTGCCAACAAACACTTTTGGGA

AGCCTGGGACCATGGCTCTGCCAGGAATCTGTGACATCTCCAGGGCATCA

TTTGAGTCCTGCCTTCTCAAAG

SEQ ID NO. 48
>contig_TCC_36B5_RF.fa
CTCTTCTTATGCTAATATGCTCTGGGCTGGAGAAATGAAATCCTCAAGCC

ATCAGGATTTGCTATTTAAGTGGCTTGACAACTGGGCCACCAAAGAACTT

GAACTTCACCTTTTAGGATTTGAGCTGTTCTGGAACACATTGCTGCACTT

TGGAAAGTCAAAATCAAGTGCCAGTGGCGCCCTTTCCATAGAGAATTTGC

CCAGCTTTGCTTTAAAAGATGTCTTGTTTTTTATATACACATAATCAATA

GGTCCAATCTGCTCTCAAGGCCTTGGTCCTGGTGGGATTCCTTCACCAAT

TACTTTAATTAAAAATGGCTGCAACTGTAAGAACCCTTGTCTGATATATT

TGCAACTATGCTCCCATTTACAAATG

SEQ ID NO. 49
>contig_TCC_42G5_RF.fa
CCTTCCGAAATACTTCCTCCAGGTGGCAGCACCAAGAATATTTCTGGAAG

CATGTGATGAGTTGTGTGATGAAGATAGAGCCCATTGTGCTGTCTCTCCA

GGACACGTTGTGTGGCGTTGAAGAGCAGAAAGCAATGAAGTCCTTCTCCA

CGTGGGTCTTGTAAACAGCATCTTCCTCCAGGTTCTCAGATGACTGTGAA

GAGGCCACTTCCAAGGATGCTGGAGAGTCTCTGACCCACAGTTCCCCACG

GTTTGCACCTCTGCAGGCCTGGACAATGATGACCTTGGGTTTGTCCTTCA

GACTGAGGCAGTTGCGGTTGTTGAATATCTGGAAGATGGTGTCATAAAGC

AGCACATCTGGTTTTTTCTCATCATGCACAGTTCCGCAGATTCCCTCCAG

GATGCCATGAGACATGGG

SEQ ID NO. 50
>contig_TCC_44C1_RF.fa
CTCATTGAACTTGAGCTCCGAGTCCTGATTCACATCCAAGCTCTTCATCT

TCTCATCAAGAGAGCCCACATCCTTGAGCAGATGGGCAACTGCTGGGTA

ACCAGCTCTTTGAACTCGTTGACGCTGAGGCTATCCTTCCGGCCCTCCTG

CCTTGCAAAGGTGAAGAAGGTGGTGACCACGGTCTCAATGGACTCCTCTA

GCTCTGTCAGTGGTTCTGCTGCCATTAGGACCCTGAGGCCAAAGCTGATG

TCCTCAAGGGGCTAGCTGACCTTTGTCAGGGCTGACCTCTCCTCAGCGGC

AGCAGGGCAGAGTGCTGAACCCAGGACCCCACAGATCCTCCCCGCTCCTG

TCTCCCGGTGACAAGGGTCCTGGAACGGGGCGTCTCTGACTCCCTGCTCC

AGGACGGGTTTAG

SEQ ID NO. 51
>contig_TCC_54C11_RF.fa
TTTTTTTTTTTTTTTTTGGTTACGGCAGCACTTTTATTTTTCCTTACACA

ATGACGTGTTGCTGGGGCCTAATGTTCTCACATAACAGTAGAAAACCAAA

ATTTGTTGTCATCTCTTCAAAGAATCGAGAATTGCGTACAAAAAAAAAAA

AAAAAAA

SEQ ID NO. 52
>contig_TCC_56E11_RF.fa
CTCTCCAGTTTGCACCTGTCCCCACCCTCCACTCAGCTGTCCTGCAGCAA

ACACTCCACCCTCCACCTTCCATTTTCCCCCACTACTGCAGCACCTCCAG

GCCTGTTGCTATAGAGCCTACCTGTATGTCAATAAACAACAGCTGAAGCA

AAAAAAAAAAAAAA

SEQ ID NO. 53
>contig_TCC_57B3_RF.fa
GGTACGACGGACCTGCGGAGACTCCTGCCCTGTTGTGTATAGATGCAAGA

TATTTATATATATTTTTGGTTGTCAATATTAAATACAGACACTAAGTTAT

AGTATATCTGGACAAGCCAACTTGTAAATACACCACCTCACTCCTGTTAC

TTACCTAAACAGATATAAATGGCTGGTTTTTAGAAAAAAAAAAAAAAAAA

A

SEQ ID NO. 54
>contig_TCC_58A3_RF.fa
GGCTGGAGCAGGAGATTGCCACCTACCGCCGCCTGCTGGAGGGAGAGGAT

GCCCACCTGACTCAGTACAAGAAAGAACCGGTGACCACCCGTCAGGTGCG

TACCATTGTGGAAGAGGTCCAGGATGGCAAGGTCATCTCCTCCCGCGAGC

AGGTCCACCAGACCACCCGCTGAGGACTCAGCTACCCCGGCCGGCCACCC

AGGAGGCAGGGAGGCAGCCGCCCCATCTGCCCCACAGTCTCCGGCCTCTC

CAGCCTCAGCCCCCTGCTTCAGTCCCTTCCCCATGCTTCCTTGCCTGATG

ACAATAAAGCTTGTTGACTCAGCTAAAAAAAAAAAAAAAAAA

SEQ ID NO. 55
>contig_TCC_70E8_RF.fa
TTTTTTTTTTTTTTTTTGCTAGTGGCATGGTTTTCCTGGGAAAGTCCTCC

TGAGTAAAAGAGGAGAGACACCTGGTGAAGACTGGGACGCAGGTACGTCT

ACC

SEQ ID NO. 56
>contig_TCC_71E4_RF.fa
CTCCAGCGATATGTTCAACTATGAAGAATACTGCACCGCCAACGCAGTCA

CTGGGCCTTGCCGTGCATCCTTCCCACGCTGGTACTTTGACGTGGAGAGG

AACTCCTGCAATAACTTCATCTATGGAGGCTGCCGGGGCAATAAGAACAG

CTACCGCTCTGAGGAGGCCTGCATGCTCCGCTGCTTCCGCCAGCAGGAGA

ATCCTCCCCTGCCCCTTGGCTCAAAGGTGGTGGTTCTGGCGGGGCTGTTC

GTGATGGTGTTGATCCTCTTCCTGGGAGCCTCCATGGTCTACCTGATCCG

GGTGGCACGGAGGAACCAGGAGCGTGCCCTGCGCACCGTCTGGAGCTCCG

GAGATGACAAGGAGCAGCTGGTGAAGAACACATATGTCCTGTGACCGCCC

TGTCGCCAAGAGGACTGGGAAGGGAGGGGAGACTATGTGTGAGCTTTTTT

TAAATAGAGGGATTGACTCGGATTTGAGTGATCATTAGGGCTGAGGTCTG

TTTCTCTGGGAGGTAGGACGGCTGCTTCCTGGTCTGGCAGGGATGGGTTT

TABLE 6-continued

Polynucleotides corresponding to the Genes described in Table 5

GCTTTGGAAATCCTCTAGGAGGCTCCTCCTCGCATGGCCTGCAGTCTGGC

AGCAGCCCCGAGTTGTTTCCTCGCTGATCGATTTCTTTCCTCCAGGTAGA

GTTTTCTTTGCTTATGTTGAATTCCATTGCCTCTTTTCTCATCACAGAAG

TGATGTTGGAATCGTTTCTTTTGTTTGTCTGATTTATGGTTTTTTTAAGT

ATAAACAAAAGTTTTTTATTAGCATTCTGAAAGAAGGAAAGTAAAATGTA

CAAGTTTAATAAAAAGGGGCCTTCCCCTTTAGAATAAATTTCAGCATGTG

CTTTCAAAAAAAAAAAAAAAAAA

SEQ ID NO. 57
>contig_TCC_75E3_RF.fa
AAAGAGGGCGGCAGGGGCCTGGAGATCCTCCTGCAGACCACGCCCGTCCT

GCCTGTGGCGCCGTCTCCAGGGGCTGCTTCCTCCTGGAAATTGACGAGGG

GTGTCTTGGGCAGAGCTGGCTCTGAGCGCCTCCATCCAAGGCCAGGTTCT

CCGTTAGCTCCTGTGGCCCCACCCTGGGCCCTGGGCTGGAATCAGGAATA

TTTTCCAAAGAGTGATAGTCTTTTGCTTTTGGCAAAACTCTACTTAATCC

AATGGGTTTTTCTCTGTACAGTAGATTTTCCAAATGTAATAAACTTTAAT

ATAAAGTAAAAAAAAAAAAAAAAAA

SEQ ID NO. 58
>contig_TCC_78B11_RF.fa
GGACCGGAACAAGGACCAGGAGGTGAACTTCCAGGAGTATGTCACCTTCC

TGGGGGCCTTGGCTTTGATCTACAATGAAGCCCTCAAGGGCTGAAAATAA

ATAGGGAAGATGGAGACACCCTCTGGGGGTCCTCTCTGAGTCAAATCCAG

TGGTGGGTAATTGTACAATAAATTTTTTTGGTCAAATTTAAAAAAAAAA

AAAAAAA

SEQ ID NO. 59
>contig_TCC_89G3_RF.fa
CAGGAGACCATCCGCGTCACCAAGCCCTGCACCCCCAAGACCAAAGCAAA

GGCCAAAGCCAAGAAAGGGAAGGGAAAGGACTAGACGCCAAGCCTGGATG

CCAAGGAGCCCCTGGTGTCACATGGGCCTGGCCCACGCCCTCCCTCTCC

CAGGCCCGAGATGTGACCCACCAGTGCCTTCTGTCTGCTCGTTAGCTTTA

ATCAATCATGCCCTGCCTTGTCCCTCTCACTCCCCAGCCCCACCCCTAAG

TGCCCAAAGTGGGGAGGGACAAGGGATTCTGGGAAGCTTGAGCCTCCCC

AAAGCAATGTGAGTCCCAGAGCCCGCTTTTGTTCTTCCCCACAATTCCAT

TACTAAGAAACACATCAAATAAACTGACTTTTTCCCCCAAAAAAAAAAA

AAAAA

SEQ ID NO. 60
>contig_TCC_92D7_RF.fa
TTTTTTTTTTTTTTTGAAGACAACTTTTAGAAACTGATGTTTATTTTCCA

TCAACCATTTTTCCATGCTGCTTAAGAGCCTATGCAAGAACAGCTTAAGA

CCAGTCAGTGGTTGAAGTC

SEQ ID NO. 61
>contig_TCC_93G5_RF.fa
GACTACCAGACCAACAAAGCCAAGCATGATGAGCTGACCTATTTCTGATC

CTGACTTTGGACAAGGCCCTTCAGCCAGAAGACTGACAAAGTCATCCTCC

TABLE 6-continued

Polynucleotides corresponding to the Genes described in Table 5

GTCTACCAGAGCGTGCACTTGTGATCCTAAAATAAGCTTCATCTCCGGGC

TGTGCCCCTTGGGGTGGAAGGGGCAGGATTCTGCAGCTGCTTTTGCATTT

CTCTTCCTAAATTTCATTGTGTTGATTTCTTTCCTTCCCAATAGGTGATC

TTAATTACTTTCAGAATATTTTCAAAATAGATATATTTTTAAAATCCTTA

CAAAAAAAAAAAAAAA

SEQ ID NO. 62
>contig_TCC_94G3_RP.fa
AAGGCTTATTCCATCCGGACCGCATCCGCCAGTCGCAGGAGTGCCCGCGA

CTGAGCCGCCTCCCACCACTCCACTCCTCCAGCCACCACCCACAATCACA

AGAAGATTCCCACCCCTGCCTCCCATGCCTGGTCCCAAGACAGTGAGACA

GTCTGGAAAGTGATGTCAGAATAGCTTCCAATAAAGCAGCCTCATTCTGA

GGCCTGAGTGAAAAAAAAAAAAAAAAAA

SEQ ID NO. 63
>contig_TCC_99G12_RF.fa
AGCGGCTATGCAGGTGGTCTGAGCTCGGCCTATGGGGGCCTCACAAGCCC

CGGCCTCAGCTACAGCCTGGGCTCCAGCTTTGGCTCTGGCGCGGGCTCCA

GCTCCTTCAGCCGCACCAGCTCCTCCAGGGCCGTGGTTGTGAAGAAGATC

GAGACACGTGATGGGAAGCTGGTGTCTGAGTCCTCTGACGTCCTGCCCAA

GTGAACAGCTGCGGCAGCCCCTCCCAGCCTACCCCTCCTGCGCTGCCCCA

GAGCCTGGGAAGGAGGCCGCTATGCAGGGTAGCACTGGGAACAGGAGACC

CACCTGAGGCTCAGCCCTAGCCCTCAGCCCACCTGGGGAGTTTACTACCT

GGGGACCCCCCTTGCCCATGCCTCCAGCTACAAAACAATTCAATTGCTTT

TTTTTTTTTGGTCCAAAATAAAACCTCAGCTAGCTCTGCCAATGTCAAAA

AAAAAAAAAAAAAAA

References

AMERICAN CANCER SOCIETY, Estimating new cancer cases and deaths by sex for all sites, Cancer Facts and Figures, pg. 4 (1998)

Burke and Olson, "Preparation of Clone Libraries in Yeast Artificial-Chromosome Vectors" in *Methods in Enzymology*, Vol. 194, "Guide to Yeast Genetics and Molecular Biology", eds. C. Guthrie and G. Fink, Academic Press, Inc., Chap. 17, pp. 251–270 (1991).

Capecchi, "Altering the genome by homologous recombination" *Science* 244:1288–1292 (1989).

Cregg J M, Vedvick T S, Raschke W C: Recent Advances in the Expression of Foreign Genes in *Pichia pastoris*, Bio/Technology 11:905–910, 1993

Culver, 1998. Site-Directed recombination for repair of mutations in the human ADA gene. (Abstract) Antisense DNA & RNA based therapeutics, February, 1998, Coronado, CA.

Davies et al., "Targeted alterations in yeast artificial chromosomes for inter-species gene transfer", *Nucleic Acids Research*, Vol. 20, No. 11, pp. 2693–2698 (1992).

Diatchenko et al., "Suppression subtractive hybridization: A method for generating differentially regulated or tissue-specific cDNA probes and libraries" Proc. Nat Acad. Sci., Vol. 93, pp. 60256030 (1996).

Dickinson et al., "High frequency gene targeting using insertional vectors", Human Molecular Genetics, Vol. 2, No. 8, pp. 1299–1302 (1993).

Duff and Lincoln, "Insertion of a pathogenic mutation into a yeast artificial chromosome containing the human APP gene and expression in ES cells", Research Advances in Alzheimer's Disease and Related Disorders, 1995.

Gilboa, E, Eglitis, M A, Kantoff, P W, Anderson, W F: Transfer and expression of cloned genes using retroviral vectors. BioTechniques 4(6):504–512, 1986.

GROSSMAN, H B, Semin. Urol. Oncol., 16(1):17–22 (1998)

HUDSON M A, and HERR H W, Carcinoma in situ of the bladder, J. Urol., 153(3, Part 1):564–572 (1995)

HUDSON, M A and HERR H W, Carcinoma in situ of the bladder, J. Urol., 153(3) Part 1):564–572 (1995)

Huston et al, 1991 "Protein engineering of single-chain Fv analogs and fusion proteins" in Methods in Enzymology (JJ Langone, ed.; Academic Press, New York, N.Y.) 203:46–88.

Huxley et al., "The human HPRT gene on a yeast artificial chromosome is functional when transferred to mouse cells by cell fusion", Genomics, 9:742–750 (1991).

Jakobovits et al., "Germ-line transmission and expression of a human-derived yeast artificial chromosome", Nature, Vol. 362, pp. 255–261 (1993).

Johnson and Bird, 1991 "Construction of single-chain Fvb derivatives of monoclonal antibodies and their production in Escherichia coli in Methods in Enzymology (JJ Langone, ed.; Academic Press, New York, N.Y.) 203:88–99.

LACOMBE L et al., Overexpression of p53 protein in a high-risk population of patients with superficial bladder cancer before and after bacillus Calmette-Guerin therapy; correlation to clinical outcome, J. Urol., 153(3, Part 1):564–572 (1995)

Lamb et al., "Introduction and expression of the 400 kilobase precursor amyloid protein gene in transgenic mice", Nature Genetics, Vol. 5, pp. 22–29 (1993).

Mernaugh and Mernaugh, 1995 "An overview of phage-displayed recombinant antibodies" in Molecular Methods In Plant Pathology (RP Singh and US Singh, eds.; CRC Press Inc., Boca Raton, Fla.) pp. 359–365.

OZEN H., Curr. Opin. Oncol., 10(3):273–8 (1998)

Pearson and Choi, Expression of the human β-amyloid precursor protein gene from a heast artificial chromosome in transgenic mice. Proc. Natl. Scad. Sci. USA, 1993. 90:10578–82.

Rothstein, "Targeting, disruption, replacement, and allele rescue: integrative DNA transformation in yeast" in Methods in Enzymology, Vol. 194, "Guide to Yeast Genetics and Molecular Biology", eds. C. Guthrie and G. Fink, Academic Press, Inc., Chap. 19, pp. 281–301 (1991).

Schedl et al., "A yeast artificial chromosome covering the tyrosinase gene confers copy number-dependent expression in transgenic mice", Nature, Vol. 362, pp 258–261 (1993).

Strauss et al., "Germ line transmission of a yeast artificial chromosome spanning the murine $\alpha_1$ (I) collagen locus", Science, Vol. 259, pp. 1904–1907 (1993).

TORTI F M and LURN B L, The biology and treatment of superficial bladder cancer, J. Clin. Oncol., 2(5):505–531 (1984).

What is claimed is:

1. A method of diagnosing bladder cancer in a human subject which comprises the step of:

determining, in a sample from the human subject, the level of expression of at least two polynucleotides, wherein a higher level of expression of the polynucleotides compared to the level of expression of the polynucleotides in a human subject free of bladder cancer is indicative of bladder cancer, and wherein the polynucleotides are selected from the group consisting of polynucleotides having SEQ ID NOS: 57, 56, and 41.

2. The method according to claim 1, wherein the determining step includes using mRNA from an expressed gene to hybridize to at least two polynucleotides selected from the group consisting of the polynucleotides having SEQ ID NOS: 57, 56, and 41.

3. The method according to claim 1, wherein the determining step includes a step of using RT-PCR technology.

4. The method according to claim 1, wherein the determining step comprises using a specific antibody to detect the presence of a polypeptide encoded by one of said polynucleotides.

5. The method according to claim 1, wherein the bladder cancer is transitional cell carcinoma.

6. The method of claim 1 wherein the level of expression of at least three polynucleotides is determined.

7. The method of claim 1 wherein the polynucleotide having SEQ ID NO:57 is a Homo sapiens syndecan-1 polynucleotide wherein the polynucleotide having SEQ ID NO:56 is a Homo sapiens hepatocyte growth factor activator inhibitor type 2 polynucleotide.

* * * * *